United States Patent
Addleman et al.

(10) Patent No.: US 10,254,248 B2
(45) Date of Patent: Apr. 9, 2019

(54) COLLECTION, RELEASE, AND DETECTION OF ANALYTES WITH POLYMER COMPOSITE SAMPLING MATERIALS

(71) Applicant: BATTELLE MEMORIAL INSTITUTE, Richland, WA (US)

(72) Inventors: Raymond S Addleman, Benton City, WA (US); Xiaohong Shari Li, Richland, WA (US); Wilaiwan Chouyyok, West Richland, WA (US); David A Atkinson, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 14/692,460

(22) Filed: Apr. 21, 2015

(65) Prior Publication Data

US 2016/0313218 A1    Oct. 27, 2016

(51) Int. Cl.
*G01N 1/18* (2006.01)
*G01N 1/22* (2006.01)
(Continued)

(52) U.S. Cl.
CPC .......... *G01N 27/622* (2013.01); *G01N 1/02* (2013.01); *G01N 1/405* (2013.01);
(Continued)

(58) Field of Classification Search
CPC ............ G01N 1/18; G01N 15/06; G01N 7/00; G01N 1/22
(Continued)

(56) References Cited

U.S. PATENT DOCUMENTS

| | | |
|---|---|---|
| 3,034,851 A | 5/1962 | Dustman, Jr. |
| 4,003,257 A | 1/1977 | Flecther et al. |

(Continued)

FOREIGN PATENT DOCUMENTS

| | | |
|---|---|---|
| WO | 2012071605 A1 | 6/2012 |
| WO | 20140165634 A2 | 10/2014 |

(Continued)

OTHER PUBLICATIONS

Lee Young, "International Search Report and the Written Opinion of the International Searching Authority (ISA)" for Battelle Memorial Institute, International Patent Application No. PCT/US2016/00037, dated Jul. 21, 2016, all pages.

(Continued)

*Primary Examiner* — Brian J. Sines
(74) *Attorney, Agent, or Firm* — Wells St. John P.S.

(57) ABSTRACT

A unique fiber core sampler composition, related systems, and techniques for designing, making, and using the same are described. The sampler is used to interface with existing field instrumentation, such as Ion Mobility Spectrometer (IMS) equipment. Desired sampler characteristics include its: stiffness/flexibility; thermal mass and conductivity; specific heat; trace substance collection/release dependability, sensitivity and repeatability; thickness; reusability; durability; stability for thermal cleaning; and the like. In one form the sampler has a glass fiber core with a thickness less than 0.3 millimeter that is coated with a polymer including one or more of: polymeric organofluorine, polyimide, polyamide, PolyBenzlmidazole (PBI), PolyDiMethylSiloxane (PDMS), sulfonated tetrafluoroethylene (PFSA) and Poly(2,6-diphenyl-p-phenylene Oxide) (PPPO). Multiple polymer coatings with the same or different polymer types may be included, core/substrate surface functionalization utilized, and/or the (Continued)

core/substrate may be at partially filled with thermally conductive particles.

10 Claims, 24 Drawing Sheets

(51) Int. Cl.
  *G01N 15/06* (2006.01)
  *G01N 7/00* (2006.01)
  *G01N 27/62* (2006.01)
  *G01N 1/02* (2006.01)
  *G01N 1/40* (2006.01)

(52) U.S. Cl.
  CPC . *G01N 2001/024* (2013.01); *G01N 2001/027* (2013.01); *G01N 2001/028* (2013.01); *G01N 2001/4061* (2013.01)

(58) Field of Classification Search
  USPC ......... 422/50, 68.1, 83, 88, 69; 436/43, 178, 436/181
  See application file for complete search history.

(56) References Cited

U.S. PATENT DOCUMENTS

| | | | |
|---|---|---|---|
| 5,147,967 A | 9/1992 | Stern et al. | |
| 5,200,614 A | 4/1993 | Jenkins | |
| 5,279,742 A | 1/1994 | Markell et al. | |
| 5,468,842 A | 11/1995 | Howard, Jr. | |
| 5,491,337 A | 2/1996 | Jenkins et al. | |
| 5,616,407 A | 4/1997 | Fritz et al. | |
| 5,763,360 A | 6/1998 | Gundel et al. | |
| 5,768,334 A | 6/1998 | Maitrejean et al. | |
| 5,777,126 A | 7/1998 | Pastor et al. | |
| 6,642,513 B1 | 11/2003 | Jenkins et al. | |
| 6,690,005 B2 | 2/2004 | Jenkins et al. | |
| 6,765,198 B2 | 7/2004 | Jenkins et al. | |
| 6,815,670 B2 | 11/2004 | Jenkins et al. | |
| 7,663,099 B2 | 2/2010 | Reda | |
| 7,856,898 B2 | 12/2010 | Carey | |
| 7,892,630 B1 | 2/2011 | McKnight et al. | |
| 8,367,314 B2 | 2/2013 | Chilkoti | |
| 8,388,907 B2 | 3/2013 | Gold et al. | |
| 8,414,846 B2 | 4/2013 | Gold et al. | |
| 8,506,911 B2 | 8/2013 | Soderquist et al. | |
| 8,590,791 B2 | 11/2013 | Hass et al. | |
| 8,636,966 B2 | 1/2014 | Soderquist et al. | |
| 8,772,045 B1 | 7/2014 | Haas | |
| 8,943,910 B2 | 2/2015 | Addleman | |
| 2001/0045000 A1 | 11/2001 | Gundel et al. | |
| 2006/0086173 A1 | 4/2006 | St. Germain | |
| 2007/0231923 A1* | 10/2007 | Cumberland | G01N 33/558 436/514 |
| 2007/0251822 A1 | 11/2007 | Hoagland et al. | |
| 2008/0260581 A1* | 10/2008 | Rosman | B01L 3/5029 422/68.1 |
| 2009/0197283 A1* | 8/2009 | Gold | B01L 3/5029 435/7.9 |
| 2010/0099192 A1 | 4/2010 | Brenneman et al. | |
| 2011/0089051 A1 | 4/2011 | Wang et al. | |
| 2011/0092377 A1 | 4/2011 | Agrawal et al. | |
| 2011/0186436 A1 | 8/2011 | Novosselov et al. | |
| 2012/0107949 A1 | 5/2012 | Haas et al. | |
| 2013/0276555 A1* | 10/2013 | Addleman | B01L 3/502707 73/864.71 |
| 2014/0069184 A1* | 3/2014 | McAlary | E21B 49/081 73/152.28 |
| 2014/0227796 A1 | 8/2014 | Gold et al. | |
| 2014/0264002 A1 | 9/2014 | Goedecke | |
| 2015/0330879 A1 | 11/2015 | Mai | |
| 2016/0027846 A1 | 1/2016 | Lieber et al. | |

FOREIGN PATENT DOCUMENTS

| | | |
|---|---|---|
| WO | WO PCT/US16/00037 | 10/2017 |
| WO | WO PCT/US16/00038 | 10/2017 |

OTHER PUBLICATIONS

Anonymous Authorship, "Search History" for the foregoing International Search Report and the Written Opinion of the International Searching Authority (ISA) for Battelle Memorial Institute, International Patent Application No. PCT/US2016/00037, dated Jul. 21, 2016, all pages.

Lee Young, "International Search Report and the Written Opinion of the International Searching Authority (ISA)" for Battelle Memorial Institute, International Patent Application No. PCT/US16/00038, dated Sep. 30, 2016, all pages.

Anonymous Authorship, "Search History" for the foregoing International Search Report and the Written Opinion of the International Searching Authority (ISA) for Battelle Memorial Institute, International Patent Application No. PCT/US16/00038, dated Sep. 30, 2016, all pages.

(Author Unknown) "Woven Fabric Style Guide" online article, dated Jan. 1, 2012, ACP Composites.

(Author Unknown) "Support throughout Your Product Lifecycle from the Plastic and Rubber Experts" online article, dated at least as early as Aug. 30, 2014, Smither Rapa.

(Author Unknown) "Modulus of Elasticity—Youngs Modulus for Some Common Materials" online article, dated at least as early as Sep. 13, 2014, The Engineering Toolbox.

(Author Unknown) "Phenolic" online article, dated at least as early as Oct. 1, 2014, San Diego Plastics, Inc.

(Author Unknown) "Flexural Strength Testing of Plastics" online article, dated at least as early as Apr. 1, 2014, MatWeb.

(Author Unknown) "Teflon" online article, dated at least as early as Apr. 1, 2014, WS Hampshire Inc.

(Author Unknown) "Itemiser 3 Enhanced" online article, Safran Morpho, dated at least as early as 2010.

(Author Unknown) "Cross-Product Consumables" online article, dated at least as early as 2013, Safran Morpho.

(Author Unknown) "Technical Data Sheet [for Recycled PVC Card Stock]" online article, dated at least as early as Apr. 6, 2014, Earthworks Systems.

(Author Unknown) "Fabric Selection/Design Performance" online article, dated at least as early as Oct. 7, 2014, BGF Industries.

(Author Unknown) "Woven Fabrics" online article purportedly published by netcomposites, dated at least as early as Oct. 9, 2014.

Frederick T. Wallenberger et al. "Glass Fibers" ASM Handbook, Composites, Constituent Materials, dated the year 2001, pp. 27-34, vol. 21, published by ASM International.

(Author Unknown) " . . . Test Methods for Flexural Properties of . . . Plastics . . . [partial title to fit form]" ASTM Handbook D 790-02, ASTM Int'l, dated at least by Apr. 10, 2002.

(Author Unknown) " . . . Test Methods for Flexural Properties of . . . Plastics . . . [partial title to fit form]" ASTM Handbook D 790-02, ASTM Int'l, dated at least by.

F Mujika, "On the Difference Between Flexural Moduli obtained by Three-Point and Four-Point Bending Tests" online article via acedemia. edu, dated Sep. 12, 2005, Elsevier Ltd.

Sinval Adalberto Rodrigues Jr. et al. "Flexural Strength and Modulus of Elasticity of Different Types of Resin-Based Composites" Braz Oral Res, Aug. 2, 2006, pp. 16-21, vol. 21(1).

Lawrence C. Bank "Flexural and Shear Moduli of Full-Section Fiber Reinforced Plastic (FRP) Pultruded Beams" Journal of Testing and Evaluation, Jan. 1, 1989, pp. 40-45, vol. 17.

Sina Ebnesajjad "Introduction to Fluoropolymers" Applied Plastics Engineering Handbook, 2011, pp. 49-60, Elsevier Inc.

C. Riul et al. "Processing . . . Evaluation of Glass Fiber-Reinforced PTFE Laminates" Composites Science and Technology, Jun. 1, 2012, pp. 1451-1458, vol. 72, Elsevier Ltd.

(56) References Cited

OTHER PUBLICATIONS

Alena Paule Nova "Dissolution of Uranim Dioxide Microspheres in Carbonate and Hydrogen Peroxide Solutions" Masters Thesis, Aug. 15, 2013, pp. 1-77, Oregon State University.
C. Kweto et al. "Kenetic Study of Uranium Residue Dissolution in Ammonium Carbonate Media" J. Radioanal Nucl Chem, Aug. 24, 2014, Springerlink.com made available online.

* cited by examiner

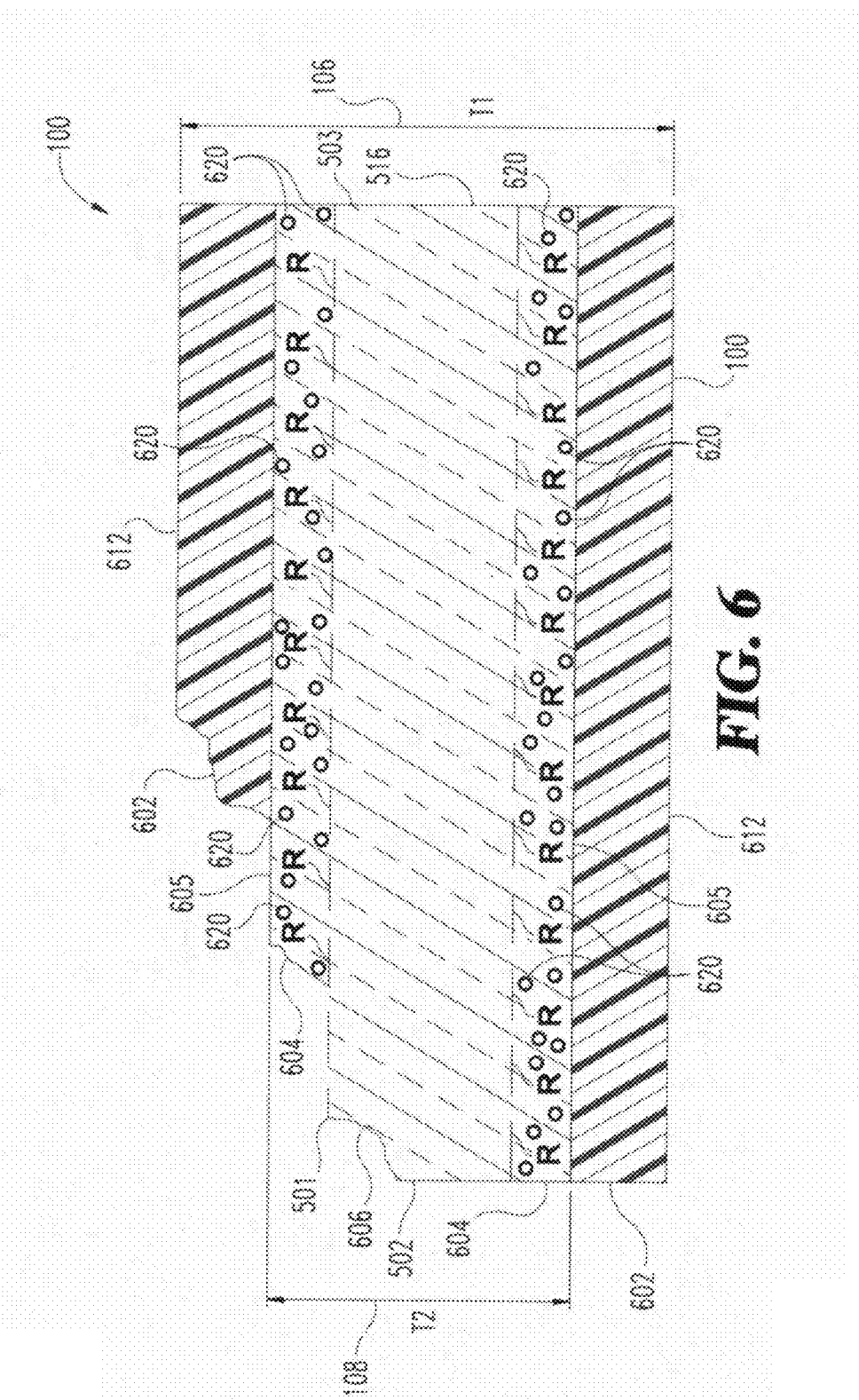

COLLECTION, RELEASE, AND DETECTION OF ANALYTES WITH POLYMER COMPOSITE SAMPLING MATERIALS

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

CROSS-REFERENCE TO RELATED APPLICATIONS

The present application is related to commonly owned U.S. patent application Ser. No. 13/450,343 to Addleman et al. filed 18 Apr. 2012 and issued 3 Feb. 2015 as U.S. Pat. No. 8,943,910 B2, which is hereby incorporated by reference as if set forth herein in its entirety (alternatively designated the '910 patent); however, to the extent there is any conflict between the present application and the '910 patent, the present application prevails.

BACKGROUND

The present application relates generally to unique techniques, systems, methods, and devices for the collection, release, extraction and/or detection of analytes; and more particularly, but not exclusively, relates to the composition, and other features of analyte sampling devices; methods of designing, making, and using analyte samplers; analyte sampler kitting; and related systems.

State-of-the-art detection of explosives, illegal pharmaceuticals, poisons, radioactive materials, heavy metals, and other chemically/biologically active substances, often involves trace analyte collection by physically wiping/swiping a test article surface with a swipe sampler that is submitted to on-site or remote instrumentation for analysis. Still other arrangements, such as walk-through portals, may generate/direct certain airstreams to facilitate analyte collection. Even so, such alternatives still often rely on a sampling device that is the same or at least similar to a swiping sampler to ultimately hold the collected analyte(s) until transfer/release for instrumentation processing can take place.

Accordingly, the proper collection, retention, release, handling, transfer, extraction and processing of contraband or undesirable substance traces with sampling devices is often of paramount concern. When used for transportation security screening, the sampling device should accommodate articles common to travel, which exhibit wide variation in terms of internal and external surface compositions and shapes desired to be sampled—posing significant challenges particularly to swipe sampler designers.

Current trace detection samplers are often made of a cotton material, like muslin, and submit the trace agent(s) to Ion Mobility Spectrometer/Spectroscopy (IMS) field equipment for analysis. Typically, IMS enables rapid analysis, has low detection limits for many analytes of interest, has a low operating cost, and requires little or no sample preparation. Consequently, IMS is one of the most widely used analytical methods for explosives detection throughout the world. However, IMS can produce erroneous results due to its lack of selectivity, susceptibility to interference, environmental humidity sensitivity, as well as nonlinear behaviors including, e.g., sample reproducibility issues, and human error.

Muslin cotton swipe material is often used to obtain samples for evaluation by a number of analytical instruments, such as Mass Spectroscopy (MS), thermal desorption Gas Chromatography (TD-GC), X-Ray Fluorescence (XRF), Inductively Coupled Plasma Mass Spectrometry (ICP-MS), and extracted uranium detection techniques. For IMS applications, recovery of the analyte from cotton/muslin sampling media can be accomplished by rinsing with solvents; however, it is less complicated to heat the sampling media to introduce the analyte into the IMS for subsequent assay. Unfortunately, heat-based release from cellulosic fibers, like cotton, is often constrained because these fibers have a limited thermal stability—decomposing at the relatively low temperature of about 150° C. Furthermore, unprocessed cotton sampling swabs contain non-cellulosic compounds found in the native fibers (i.e. waxes, natural oils and starches) as well as sizing agents and lubricants added for textile processing. Typically, processes used to remove these impurities in industry include mechanical scouring, chemical scouring agents, and enzymatic methods that can weaken the cellulosic fibers and make them unsuitable for repetitious use. Moreover, natural sampling materials can have variable backgrounds and variable chemical reactivity because of differences in natural growing processes and material sourcing from different geographic areas. In contrast, synthetic sampling materials, like certain polymeric coatings, can be produced under controlled conditions—minimizing background influence and variation from other sources using process control techniques. Various coatings can also improve uniformity. The decomposition of unstable swab material can release contaminants into a detection instrument and therefore interfere with the sample analysis and negatively impact the detection process. Also, high specific heat (>1.3 J/g ° C.), low thermal conductivity (~0.24 W/m-K), and surface chemical heterogeneity of cellulosic fiber materials can adversely impact the release of analytes from the surface—concomitantly limiting detection performance.

U.S. Pat. No. 6,642,513 B1 to Jenkins et al. (the "'513 patent"), issued on 4 Nov. 2003, offers several different alternatives to muslin sampling in the form of variously configured "traps," and is hereby incorporated by reference as if set forth in its entirety herein except to the extent the '513 patent conflicts with the present application, in which case the present application prevails. In the '513 patent, one trap type for walk-through portal applications uses directed airflow to move analytes from the subject to the trap. For this application, trap composition is stainless steel—apparently without any coating or other surface treatment. While Stainless steel was selected because of good analyte collection properties it was thought to be too abrasive for contact/swipe type applications (See the '513 patent col. 3, lines 48-63; and col. 5, line 46-col. 6, line 2). The '513 patent also specifies a polyamide fiber felt—apparently without any type of coating or other surface treatment. The '513 patent also specifies a trap having an open weave glass fiber coated by PolyTetraFluoroEthylene (PTFE). Furthermore, the coating is systematically roughened with an abrasive to cut through it and break/expose glass fibers. A scrubbing material results from the broken fibers that acts in substantially the same manner as a brush—believed to be better for analyte collection (See the '513 patent FIG. 2 and accompanying text). Moreover, coating is sparsely applied so that open spaces remain in the glass fiber web as defined by the open weave. See, for example, the '513 patent FIGS. 2 and 3 and accompanying text; and col. 2, lines 37-58.

Unfortunately, the '513 patent fails to specify or consider various salient characteristics of samplers, leaving to the imagination many aspects significant to performance. Among its shortcomings, the '513 patent proposes to improve collection by exposing glass fibers and leaving unclosed holes in the glass fiber web—potentially exposing bordering glass fibers. To the contrary, untreated glass fibers have been found to hamper the desired release of certain analyte(s) because they bind too strongly as empirically established in the description set forth hereinafter. The '513 patent is also silent as to desired thermal properties regarding analyte release by thermal desorption, glass type, and the like.

Generally, existing sampling swipes, including more rigid types, are relatively expensive and have poor thermal conductivity—typically having a relatively thick polymer (like PTFE) coating. Such configurations can impede analyte release by thermal desorption or otherwise diminish desired signal level. Current sampling techniques also fail to readily accommodate testing for certain nonstandard analytes of interest such as those associated with monitoring nuclear compliance programs and/or verifying compliance with heavy metal safety exposure standards applicable to mining and other industries. Conventionally, the sampling material needs to be digested and its chemical signature excluded from the analysis for the target analyte(s)—costing precious time and limiting the ability to obtain consistent results. Consequently, it would be desirable to have a sampling device that does not require such lengthy treatment to release analyte(s) of interest.

Improving sample collection and analyte transfer to instrumentation would likely improve sensitivity, stability, and potentially selectivity—addressing many fundamental problems presently plaguing field-deployed instruments expected to consistently detect trace analytes using conventional swipes. Indeed, existing schemes often can be cumbersome to use, and/or make it difficult to readily and consistently obtain a satisfactory result in certain instances. Accordingly, there remains an ongoing demand for further contributions in these technical arenas.

By way of transition from this background to other sections of the present application, one or more specific definitions, and any sub-definitions thereof, are set forth below and supplemented by example or further explanation where deemed appropriate. Among other things, these definitions are provided to: (a) resolve meaning sometimes subject to ambiguity and/or dispute in the applicable technical field(s) and/or (b) exercise the lexicographic discretion of any named inventor(s), as applicable:

1. "Percentage" or "percent" (%) as used herein defaults to percentage by weight of the referenced item relative to the whole (also designated by "% wt") unless a different basis is expressly indicated.

2. "Nanoparticle" means any particle having a maximum dimension in the range of about 1 nanometer through about 1000 nanometers (nm).

3. "Fabric" broadly refers to both nonwoven and woven types. Nonwoven types include, but are not limited to: felts, knitting, braiding, plaiting, Chopped Strand Mat (CSM), velour, combinations of these, and any other nonwoven fabric type known to those skilled in the art at the time of the present application filing. Woven fabric types encompass both closed weave and open weave varieties and include, but are not limited to: plain weaves, satin weaves (including, but not limited to Harness Satin (HS) weaves and crow(s) foot weave), twilled weaves, heddle weaves, herringbone weaves, houndstooth weaves, Dutch plain weaves, Dutch twilled weaves, reverse Dutch weaves, basket weaves, Leno weaves, mock Leno weaves, gauze weaves, cross weaves, tablet weaves, DURAWEAVEs, hybrid weaves, weft-faced weaves, warp-faced weaves (backstrap weaves), gauze weaves, oxford weaves, pinpoint weaves, poplin weaves, pile weaves, knotted weaves, real weight weaves, combinations of these various weaves, and other weaves as are known to those skilled in the art. Weave patterns are typically described in terms of warp and weft, which refer to relative position of the fibers used to create the weave pattern. Typically, warp fibers refer to lengthwise fibers held in a loom while the weft fibers interlace at right angles with warp fibers. The weft fibers typically are carried with a shuttle during loom operation. The weft also may be referred to as filling, woof, and pick.

4. "Closed weave" means any weave other than an "open weave" including that referenced in the '513 patent; and/or means a weave that lacks a pre-defined pattern of one or more openings through the fabric, where each such opening is wider than any fiber element bordering the same and the weave is arranged so two adjacent fiber elements are held apart from each other to provide opening formation under nominal conditions.

5. As is known to those skilled in the art, "fiber glass" or "fiberglass" sometimes refers to Glass-Reinforced Plastic (GRP), which often includes a pultrusion of roves or other configuration of a glass in combination with an amount of organic polymer, binder, and/or resin effective to prepare a corresponding composite combination thereof. However, "fiber glass/fiberglass" is also sometimes used to refer to glass fibers without organic polymer/binder/resin constituent(s) and/or before combination with the same. This distinction occasionally relies on context—often resulting in some degree of ambiguity. In contrast, "glass fiber" is more commonly accepted to refer to fibers of glass absent/ before combination with organic polymer/binder/resin constituent(s) (if ever to be so combined); and such terminology shall be used to mean the same. If the term "fiber glass" or "fiberglass" is used herein, it shall have the same meaning as "glass fiber" set forth above. Any reference to an organic polymer, binder, and/or resin in combination with "glass fiber" and/or "fiberglass/fiber glass" is expressly stated herein and/or by utilizing the "glass-reinforced plastic" (GRP) terminology.

6. "High Strength Glass" (HSG) means any non-crystalline solid composition (equivalently designated "glass" or "amorphous" composition) conforming to the following "HSG formula": 50% wt to 100% wt of any combination of aluminosilicate, aluminum silicate, and/or alumina/silica constituents (such as, for example, $Al_2O_3.SiO_2$), 0% wt to 25% wt of any combination of calcium oxide (CaO) and/or magnesium oxide (MgO), and 0% wt to 5% wt Boron oxide (such as, for example, $B_2O_3$), with any balance consisting of other constituents and/or any minor impurities. This definition includes any glass complying with the HSG formula before or after any processing, including, but not limited to: furnace heating, floating on molten material to form sheet glass, ion implantation, molten salt bath exposure, annealing, coating, or the like. This definition also means any R-glass and/or S-glass as these terms are commonly understood by those of ordinary skill in the art at the time of filing of the present application—even if not conforming to the HSG formula.

7. "Flexural modulus" is a measure of stiffness/rigidity/ resistance to bending, and is defined as the result (in units of pressure) from testing in accordance with American Society for Testing and Materials (ASTM) Standard D790 of any released version in effect on or before the filing of the present application. The flexural modulus is sometimes called the "bending modulus" or the "elastic modulus;" however, these last two terms tend to be applied inconsistently to other types of moduli, test procedures, and/or contexts, so they are not used herein. Flexural modulus corresponds to an intrinsic material property subject to certain constraints/limitations—being the ratio of stress to strain in flexural deformation as obtained by a three-point test per ASTM D790. This test applies force to a beam of the material under test as it rests on two supports. The test force is applied on the opposite side from the support contacts and at is positioned therebetween. The test beam has a specified span (length) to depth ratio and is believed to reduce or eliminate the influence of extrinsic factors (such as shapes that might impart different degrees of stiffness) during otherwise uniform the test results. For the purpose of the present application, to the extent the material under test includes reinforcing fibers that extend a greater distance (on average) along a specified direction, the beam shall be prepared so that such direction coincides with the beam span—applying the test force approximately perpendicular to and across these fibers. To the extent the fibers extend approximately the same distance in multiple directions (as with a generally planar fabric), any of these directions may be oriented to coincide with the beam span for testing purposes. Flexural modulus is similar to Young's modulus in some respects and the two sometimes have values that are well within an order of magnitude or for the same material (both in units of pressure); however, flexural modulus has become a common industry alternative to Young's modulus for synthetic organic polymers and composites because these types of materials tend to have certain properties for which Young's modulus may not prove as readily obtainable, informative, or applicable. To provide a few examples of flexural modulus, consider the following approximations: (a) PTFE<0.5 GigaPascal (GPa); (b) 25% wt glass-filled PTFE≈1.3 GPa; (c) cardstock>2.7 GPa; (d) Polyvinylchloride (PVC)≈3.3 GPa; (e) Gold<4.5 GPa; and (f) 20% wt glass-filled polycarbonate≈5.5 GPa as based on a literature search (citations omitted).

8. "Metal" means any elemental metal, with or without any minor impurities therein, and any metal alloy (defined below).

9. "Metalloid" refers to any of the following elements: aluminum, antimony, arsenic, astatine, boron, carbon (as further defined hereinafter), germanium, polonium, selenium, silicon, tellurium, or combination thereof, with or without minor impurities therein. A carbon metalloid includes any allotrope of carbon, but excludes any carbon atom to the extent it is an atomic constituent in an organic compound recognized as such in any International Union of Pure and Applied Chemistry (IUPAC) reference to organic nomenclature in effect on or before the filing of the present application. To dispel any doubt, aluminum is considered both a metal and a metalloid for the purposes of the present application.

10. "Metal alloy" means a compound comprised of a combination of two or more different metals, a combination of at least one metal and at least one metalloid, or any combination thereof, either with or without minor impurities.

11. "Inorganic metallic material" means: (1) any inorganic substance with at least a majority of the following properties: malleability; ductility; electrical conductivity; thermal conductivity; ability to melt and/or fuse two or more portions of such substance together; shiny appearance/metallic luster to the extent not covered with a coating, compound, oxide, or other constituent altering visual appearance of the same; and/or (2) any inorganic substance with one or more metals and/or metalloids alone or as an atomic constituent of a salt, compound, molecule, complex, adduct, composite, anion, cation, or other combination with a non-metal and/or a non-metalloid atomic constituent. Accordingly, inorganic metallic material includes, but is not limited to: any metal, metalloid, or metal oxide, and any glass, ceramic, or glass-ceramic having a metal or metalloid atomic constituent. To dispel any doubt, inorganic metallic material does not include any organometallic substance.

12. "Heavy metal" means certain metals and metalloids that have the potential to seriously impact the environment (including flora and fauna, among other things) and/or the safety of humans including: arsenic, cadmium, mercury, lead, chromium, copper, zinc, nickel, selenium, silver, antimony, thallium, beryllium, and cobalt in any elemental form with or without minor impurities; and/or any combination or metal alloy thereof.

13. "Contraband or undesirable substance" means any potential nefarious, illegal, dangerous, or threat agent listed in the '910 patent (in its text and/or accompanying figures), and/or any substance that belongs in one or more of the following categories: (a) explosives; (b) illegally trafficked drugs; (c) chemical or biological warfare agents; (d) nerve agents; (e) pesticides; (f) pharmaceutical process contaminants; (g) environmental toxins; (h) heavy metals; (i) actinides; (j) radioisotopes of any element with the potential to seriously impact the environment (including flora and fauna, among other things) and/or human safety; and/or (k) a salt, compound, molecule, complex, metal alloy, combination, analogue, homologue, isomer, equivalent, adduct, derivative, hydrate, composite, and/or stimulant of any substance listed in the '910 patent (in accompanying text and/or figures), and/or belonging to any of categories (a)-(j).

14. "Ammonium" broadly means any substance that includes: (a) an ammonium cation (referring to the general structure $NH_4^+$, for example); (b) like-charged amine including any such amine with primary, secondary, tertiary, or quaternary substituents; and/or (c) any salt, combination, compound, molecule, complex, equivalent, analogue, homologue, adduct, and/or, composite of any of the substances of the foregoing listings (a) and (b). In contrast, any reference to the chemical formula $NH_4^+$ for the cation alone or as part of another formula, such as $(NH_4)_2CO_3$, shall be limited to the meaning of such formula and equivalents thereto as understood by those of ordinary skill in the art at the time of filing of the present application.

15. "Onium" broadly means any substance comprising: (a) ammonium; (b) a cation formed by protonation (hydron addition) of a mononuclear parent hydride of: the nitrogen family (periodic table group 15), the oxygen family (periodic table group 16), or the halogen family (periodic table group 17); (c) derivatives formed by substitution of any cation of the above-listed parent substances of (a) & (b) by univalent groups, (the number of substituted hydrogen may be indicated by the adjectives primary, secondary, tertiary or quaternary); (d) derivatives formed by substitution of any cation of the above-listed parent substances of (a)-(c) by groups having at least two free valencies on the same atom; (e) independent of the meanings conveyed under the foregoing listings (a)-(d), onium cations shall also encompass any meaning conveyed by the onium nomenclature that follows in this listing, where such nomenclature has the meaning that would be understood by those of ordinary skill in the art at the time of filing of the present application unless expressly stated to the contrary: alkanium, alkenium, alkynium, alkonium, alkenonium, alkynonium, arenium, amidium, (including carboxamidium, for example) oxonium (refers to any oxygen cation with three bonds, including, but not limited to: hydronium, oxocarbenium, alkoxonium, triethyloxonium, methyloxonium, trimethyloxonium, trialkoxonium, oxatriquinane, and oxatriquinacene, for example), nitrenium (refers to $NH_2^+$ or more generally $R_2N^+$, for example), nitrilium (refers to any cation formed by protonation of a nitrile as represented by $R—C\equiv N^+H$ or $R—C^+=NH$, where "R" is a functional group, or alkylation of a nitrile $[RCNR']^+$, where "R" and "R'" are functional groups, for example), nitronium (refers to $NO_2^+$ formed by protonation of nitric acid or removal of an electron from the nitrogen dioxide molecule, for example), nitrosonium (refers to $NO^+$ and organic derivatives thereof, for example), iminium (refers to a protonated or substituted imine cation of the general structure $[R^1R^2C=NR^3R^4]^+$, where $R^1$, $R^2$, $R^3$ and $R^4$ are functional groups, for example), iminyhum (refers to the general structure $R_2C=N^+$, where R is a functional group, for example), nitrylium, carbonium (refers to any cation that has a pentavalent carbon atom or a carbon atom of greater valency/coordination number, including but not limited to: methanium ($CH_5^+$), ethanium ($C_2H_7^+$), alkanium, and any organic derivative thereof, for example), carbenium (refers to a molecule with a trivalent carbon atom or three-coordinate carbon atom that bears a +1 charge, and any organic derivative thereof, for example), carbynium (refers to the radical $H_2C.^+$ and any organic derivative thereof, for example), arsonium, stibonium, halonium, selenonium, fluoronium, chloronium, bromonium, borenium, telluronium, iodonium, bismuthonium, germonium, stannonium, plumbonium, boronium, silanium, hydrogenonium (refers to trihydrogen cation or protonated diatomic/molecular hydrogen, for example), hydrohelium, kryptonium, xeonium, phosphonium, sulfonium, aminodiazonium, hydrocyanonium, diazonium, pyridinium, pyrylium, hydrazinium, diazenium, silylium, and mercuronium; (f) any substance with multiple "onium" cation groups, such as a double onium ion, a triple onium ion, and greater onium ion multiples (+2, +3, and greater charge, respectively) where "onium" complies with any meaning of the foregoing listings (a)-(e); and/or (g) any salt, complex, compound, molecule, combination, adduct, hydrate, equivalent, analogue, and/or homologue of any of the substances of the foregoing listings (a)-(f). From a theoretical standpoint, onium compounds/cations are counterparts to "ate" complexes/anions—such anions often being polyatomic. Further, onium cations and ate anions can combine to form a wide range of commonly available/known salts.

16. "Carbonate" broadly means: (a) any salt or ester of carbonic acid or carbamic acid; (b) a carbonate anion ($CO_3^{2-}$), bicarbonate anion ($HCO_3^-$), polyvalent percarbonate anion species including both a carbonate anion moiety and an oxide anion moiety, divalent peroxocarbonate anion ($CO_4^{2-}$), divalent peroxodicarbonate anion ($C_2O_6^{2-}$), monovalent hydrogenperoxocarbonate anion (H—O—O—$CO_2^-$), or carbamate anion ($CH_2NO_2^-$), where it is understood that two or more of the carbonate, bicarbonate, and carbamate anion species may coexist at equilibrium in solution under certain circumstances; (c) a carbonate, bicarbonate, subcarbonate, percarbonate, peroxocarbonate, peroxodicarbonate, or sesquicarbonate anion constituent; and/or (d) any salt, complex, compound, molecule, combination, adduct, hydrate, equivalent, analogue, and/or homologue of any of the substances of the foregoing listings (a)-(c). In contrast, any reference to the chemical formula $CO_3^{2-}$ for the anion alone or as part of another formula, such as $(NH_4)_2CO_3$, shall be limited to the meaning of such formula and equivalents thereto as understood by those of ordinary skill in the art at the time of filing of the present application.

17. "Thickness" refers to the smallest dimension of an object unless expressly indicated to the contrary herein. By way of example, thickness refers to the distance between opposing sides of a generally planar sampler, where such opposing sides have a length and width much greater than such distance (thickness). To the extent thickness is quantitatively specified herein, it is determined as the average of ten (10) measurements taken at ten (10) different locations along the object using a measurement device having a rated accuracy of +/−0.01 millimeter (mm) or better. As used herein, 'thin" means at least a portion of an object under measurement has a thickness of less than or equal to 0.3 mm determined in accordance with such measurements. As a corollary, to the extent used herein an object is "thick" if it is not "thin" such that its thickness dimension is determined to be >0.3 mm as determined by measurements according to the procedure listed above. These definitions of thin and thick supersede any definition of like terms set forth in the '910 patent and/or the '513 patent.

18. To "calcine" (also calcined/calcining/calcination and the like) generally refers to heating a subject material in an enclosure at a selected temperature to remove a volatile fraction, desiccate, reduce, oxidize, and/or otherwise selectively change the subject material, and may be performed with or without control of air, oxygen, or other gas content in the enclosure in its broader form. By way of nonlimiting example, for a composite subject material, heating temperature may be selected above the melting point of a polymer constituent (but not exceeding its decomposition temperature) while remaining below the melting point of a glass fiber fabric constituent to which the polymer is applied. The selected temperature completely or partially melts the polymer constituent, changing its morphology to promote the formation of longer polymeric molecules or "chains" and/or interconnection between the same under certain circumstances, while the glass fabric is only negligibly impacted if at all (but note polymer coverage of the fabric and the polymer-glass interface may be subject to change by in this calcination example). At the same time, calcining may at least partially remove any volatile fraction present after certain liquid-based application of the polymer to the fabric (even with pre-calcination evaporation), and/or desiccate all of the constituents as a function of constituent composition, heating temperature selected, and/or heating duration. Because calcination and roasting in a metallurgical/material science context are sometimes compared, it should be appreciated that roasting is generally performed at a considerably higher temperature than calcination for a given material—where roasting typically heats an ore to promote one or more gas-solid reactions that improve metal component purity of/from the ore.

The above listing of one or more definitions/sub-definitions apply to any reference to the corresponding subject terminology herein unless explicitly set forth to the contrary. Any acronym, abbreviation, or terminology defined in parentheses, quotation marks, or the like shall have the corresponding meaning imparted thereby through the present application unless expressly stated otherwise herein.

SUMMARY

Among the embodiments of the present application are unique analyte sampler compositions/configurations and related systems, apparatus, methods, kits, processes, and devices. Other embodiments include unique techniques to design, make, use, reuse, clean, and/or extract analyte from an analyte sampler.

For some unique embodiments, it has been found a relatively stiff/rigid sampling swipe with suitable mechanical stability facilitates replicate use and desired detector interfacing. It has also been unexpectedly discovered that sampler stiffness/rigidity can be controlled within certain limits through the manner of application, concentration, and composition of polymer(s) applied to a sampler fiber core and the thermal treatment of the polymer(s) after initial deposition on the sampler fiber core. Additionally or alternatively, in other unique embodiments certain thermal characteristics/properties of a sampler are provided that are conducive to thermal release of sampler-collected analyte(s) for analysis with existing instrumentation and/or facilitate at least partial thermal cleaning of such sampler with the same. As a further alternative or additional aspect, it has been discovered that a sampler with low surface energy/hydrophobic properties enables more effective release of certain sampler-collected analyte(s). Yet other unique embodiments have been discovered conducive to extraction of heavy metals and actinides (especially uranium). In still other unique embodiments, a fabric sampler core is utilized with controlled thermal sintering, particulate addition, minimal polymer concentration, and/or chemical core treatment to enhance particle collection efficiency, polymer deposition/application, sampler thermal conductivity, and/or the release of sampler analyte(s).

In another embodiment, a sampler includes a fabric core comprised of one or more of: HSG, polymeric thermoplastic, polymeric thermoset, metal, metalloid, inorganic oxide, ceramic, and/or glass-ceramic; and a polymer applied to the fabric core that includes at least one of the group of: polymeric organofluorine, polyamide, polyimide, PolyBenzlmidazole (PBI), PolyDiMethylSiloxane (PDMS), sulfonated tetrafluoroethylene (PFSA), and Poly(2,6-diPhenyl-p-Phenylene Oxide) (PPPO). It should be appreciated that PPPO is also known by the trademark TENAX TA, and a PPPO/graphitized carbon combination (also known by the trademark TENAX GR) is encompassed by this listing given PPPO is a member of the polymer listing and the TENAX GR combination. In one more particular form, the fabric core is comprised of one or more of: HSG, metal, metalloid, metal oxide, ceramic, and glass-ceramic. In still a more particular form, the fabric core is comprised of one or more of: HSG, carbon, metal, metal oxide, ceramic, and glass-ceramic. In yet a more specific form, the fabric core includes a metal oxide coated glass (such glass may be HSG, but is not limited to such type) and/or metal oxide coated metal as further described elsewhere herein. In still an even more specific form, the fabric core is comprised of HSG. The fabric core is comprised of S-glass in an even more particular form. In other forms, the composition of the polymer applied to any of the previously described fabric core forms may be selected from any of the successively more specific listings (a)-(e) as follows: (a) perfluorocarbon, perfluoroether, Ethylene-TetraFluoroEthylene copolymer (ETFE), Ethylene ChloroTriFluoroEthylene copolymer (ECTFE), poly(tetrafluoroethylene-hexafluoropropylene-vinylidene fluoride) (THV) copolymer, PolyVinylidene diFluoride (PVdF), Fluorinated Ethylene-propylene (FEP), PolyChloroTriFluoroEthylene (PCTFE), PolyVinyl Fluoride (PVF), PolyTRiFluoroEthylene (PTRFE), poly(vinylidene-tetrafluoroethylene) copolymer, poly(vinylidene-trifluroethylene) copolymer, PPBI, PDMS, and PPPO; (b) perfluorocarbon, perfluoroether, ETFE, FEP, THV copolymer, PVdF, and PPPO; (c) perfluorocarbon, PerFluoroAlkoxy (PFA), ETFE, PVdF, and FEP (where "pefluoroether" is inclusive of PFA); (d) PFA, ETFE, FEP, and PTFE; and (e) PTFE.

Yet another embodiment is directed to a method of making a contraband or undesirable substance sampler, comprising: preparing the sampler with a fabric core formed of fibers including one or more of: glass, metalloid, metal, inorganic oxide, ceramic, and glass-ceramic; heating the fabric core to a first predefined temperature for a first predefined duration; applying a polymer to the fabric core to further prepare the sampler, the polymer being one or more of: polymeric organofluorine, polyamide, polyimide, PBI, PFSA, PDMS, and PPPO; controlling stiffness of the contraband or undesirable substance sampler by: selecting a predefined amount of the polymer for application to the fabric core, and regulating a heat treatment of the sampler at a second predefined temperature for a second predefined duration; and after the heat treatment, providing the sampler for application with detection instrumentation. Certain more specific forms include: applying the polymer by depositing it on the fabric core from a liquid particulate dispersion of such polymer, at least partially filling the fabric core with nanoparticles selected to provide a desired thermal performance before applying the polymer, functionalizing at least a portion of the surface of the fabric core with silane ligands before applying the polymer, and/or applying a further polymer layer on the polymer applied to the fabric core, where the further polymer layer has a different composition than the polymer applied to the fabric core in at least one particular embodiment. In one more particular form, the fabric core composition may be selected from any of the successively more specific listings (a)-(c): (a) HSG, metal, metalloid, inorganic oxide, ceramic, and glass-ceramic; (b) HSG, metalloid, metal, and metal oxide; and (c) HSG, carbon, metal, and metal oxide. In another specific form, the fabric core includes a metal oxide coated glass (such glass may be HSG or a non-HSG type) and/or metal oxide coated metal. In still an even more specific form, the fabric core is comprised of HSG. In yet an even more particular form, the fabric core is comprised of S-glass. Other variations result by selecting the polymer applied to any of the previously described fabric core forms may be selected from any of the successively more specific listings (a)-(e) as presented in the immediately preceding paragraph. For the previously described forms that include at least partial filling of the fabric core, the nanoparticle composition may be selected from any of the successively more specific listings (a)-(e): (a) inorganic metallic material; (b) one or more of metal, metal oxide, carbon, ceramic, and glass-ceramic; (c) one or more of metal, metal oxide, and carbon; (d) one or both of a nanotube or graphene allotrope of carbon; and (e) alumina.

Still a further embodiment detects a contraband or undesirable substance, comprising: collecting the contraband or undesirable substance with a sampler, including a woven fabric with a closed weave and a first polymer layer deposited thereon to at least partially cover the fabric, the fabric having a thickness of less than or equal to about 0.3 mm and being comprised of one or more of: glass, metalloid, metal, inorganic oxide, ceramic, and glass-ceramic, and the first polymer layer being comprised of one or more of: polymeric organofluorine, polyamide, polyimide, PBI, PDMS, PFSA, and PPPO with a calcined content of less than or equal to 40%; transferring the contraband or undesirable substance from the sampler to detection instrumentation; and detecting the contraband or undesirable substance with the instrumentation. Other forms include, preparing the sampler by at least partially filling the fabric with nanoparticles selected to provide desired thermal performance; applying a second polymer layer on the first polymer layer, which has a different composition than the first polymer layer in certain forms; and/or functionalizing at least a portion of the surface of the fabric by silanizing at least a portion of the fabric and the nanoparticles (if nanoparticles are present). In addition or as an alternative to the previously described forms, still other embodiments of the samplers have a thickness of less than or equal to 0.5 mm inclusive of all polymer layers applied to the fabric, and/or the sampler has a flexural modulus selected from among the following ranges (a)-(c): (a) from about 0.75 GPa through about 10 GPa, (b) from about 1 GPa through about 8 GPa, or (c) from about 2 GPa through about 6 GPa.

Another embodiment is directed to a kit to test for presence of one or more contraband or undesirable substances, comprising: several samplers each structured to collect the one or more contraband or undesirable substances and release the one or more contraband or undesirable substances for analysis, the samplers each including a woven fabric and a polymer applied thereto, the fabric having a thickness of less than or equal to about 0.3 mm and being comprised of one or more of: HSG, carbon, metal, ceramic, glass-ceramic, and metal oxide, and the polymer being comprised of one or more of: polymeric organofluorine, polyamide, polyimide, PBI, PDMS, PFSA, and PPPO; and a container with at least one or more of the samplers enclosed therein.

A further embodiment is directed to substance detection that includes: collecting the substance with a three-dimensional collection framework, the framework including a support structure, the support structure comprising one or more of: polymeric thermoplastic, polymeric thermoset, metal, metalloid, inorganic oxide, ceramic, and glass-ceramic; the framework including several recesses each defining an external opening facing away from the framework, a polymer applied to at least partially coat the support structure, the polymer being comprised of one or more of: polymeric organofluorine, polyamide, polyimide, PBI, PDMS, PFSA, and PPPO; transferring the substance from the collection framework to detection instrumentation; and detecting the substance with the instrumentation.

Other features, aspects, forms, embodiments, applications, implementations, techniques, objects, benefits, advantages, options, methods, processes, apparatus, configurations, arrangements, components, systems, compositions, substitutions, and variations shall become apparent from the description and figures provided herewith.

BRIEF DESCRIPTION OF THE DRAWING(S)

Figure 5:
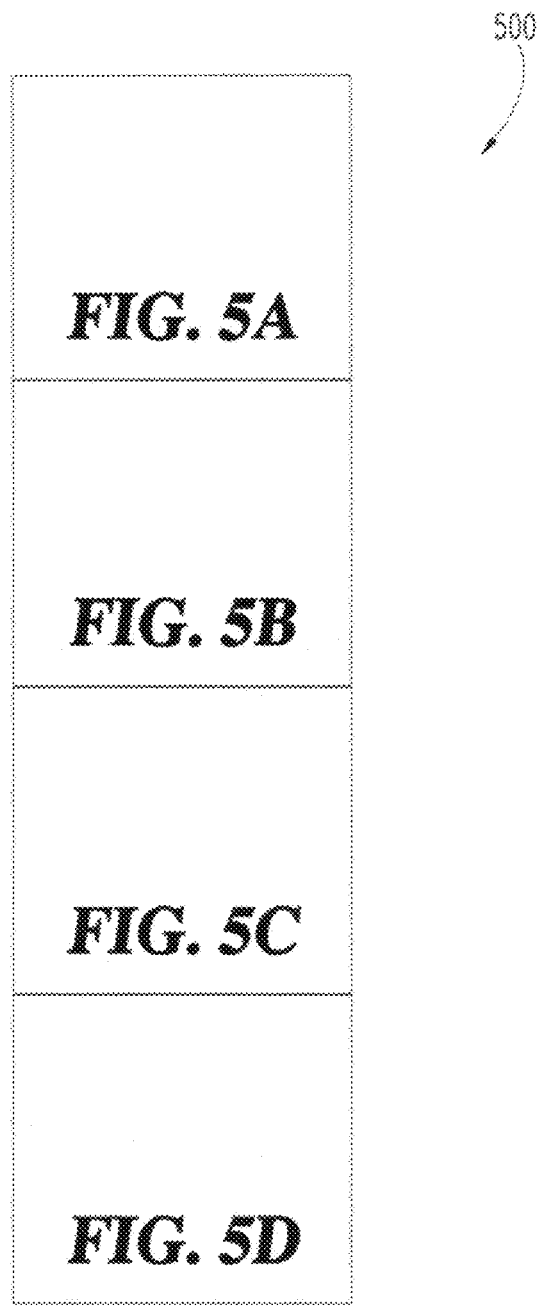
Figure 5A:
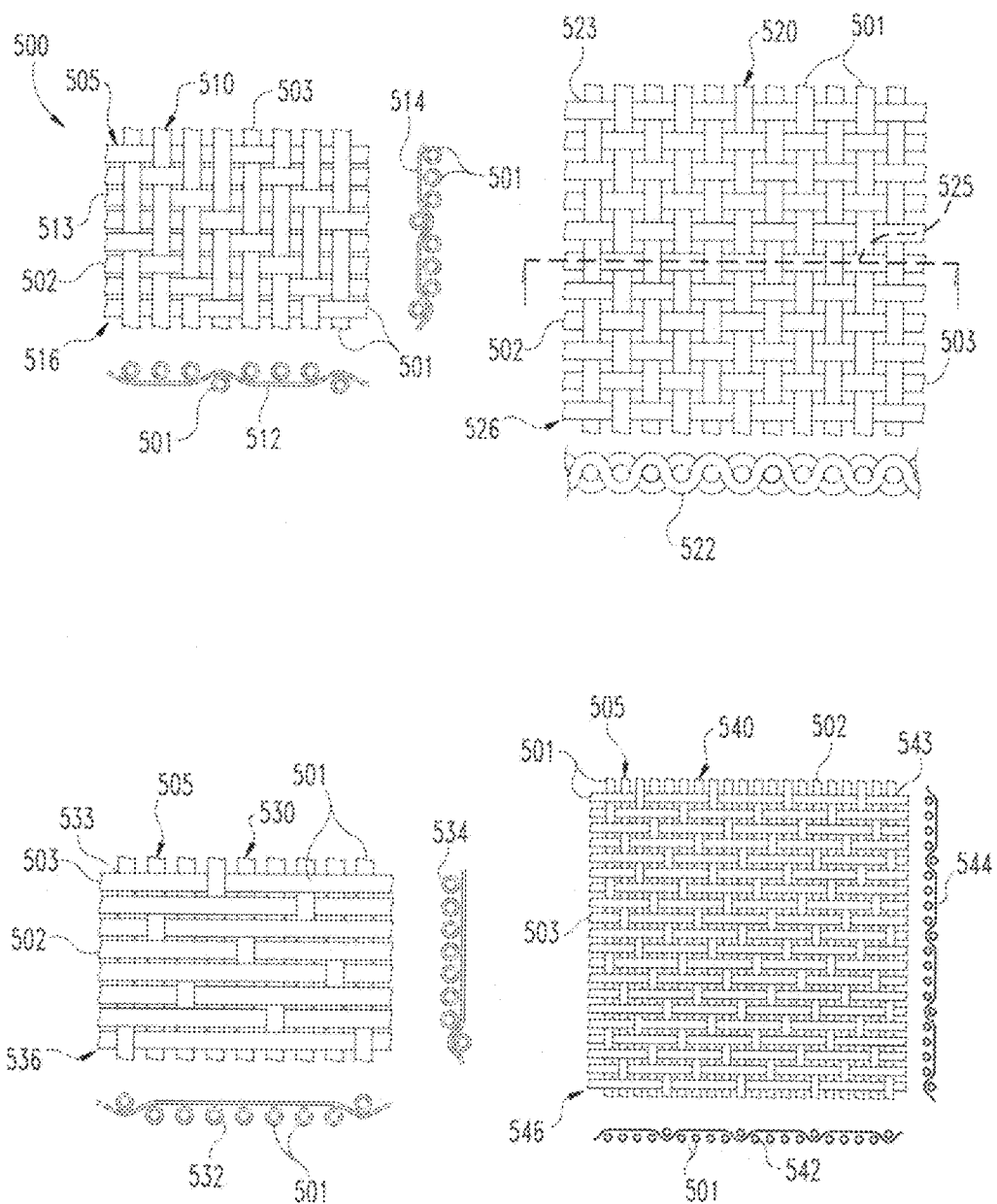
Figure 5B:
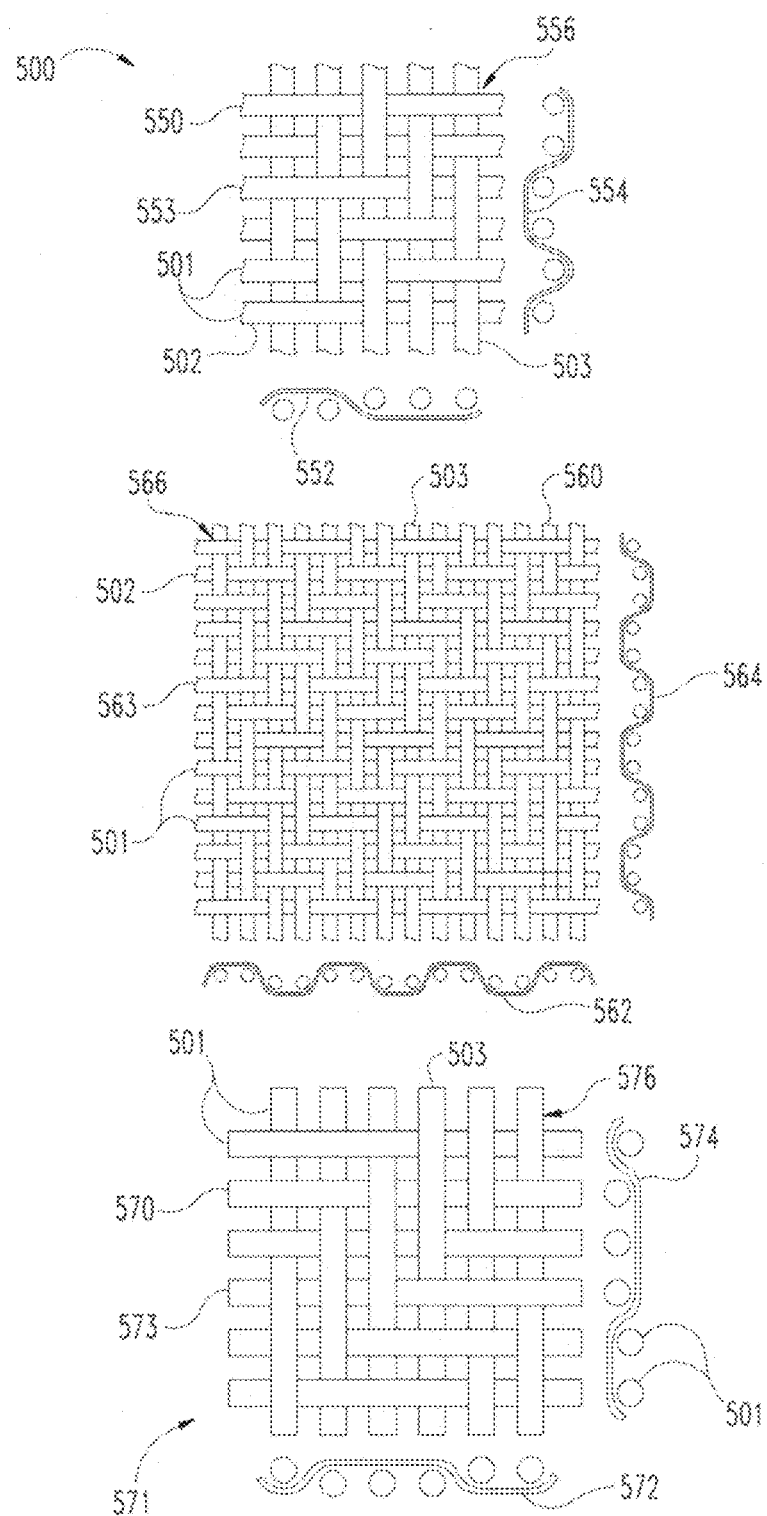
Figure 5C:
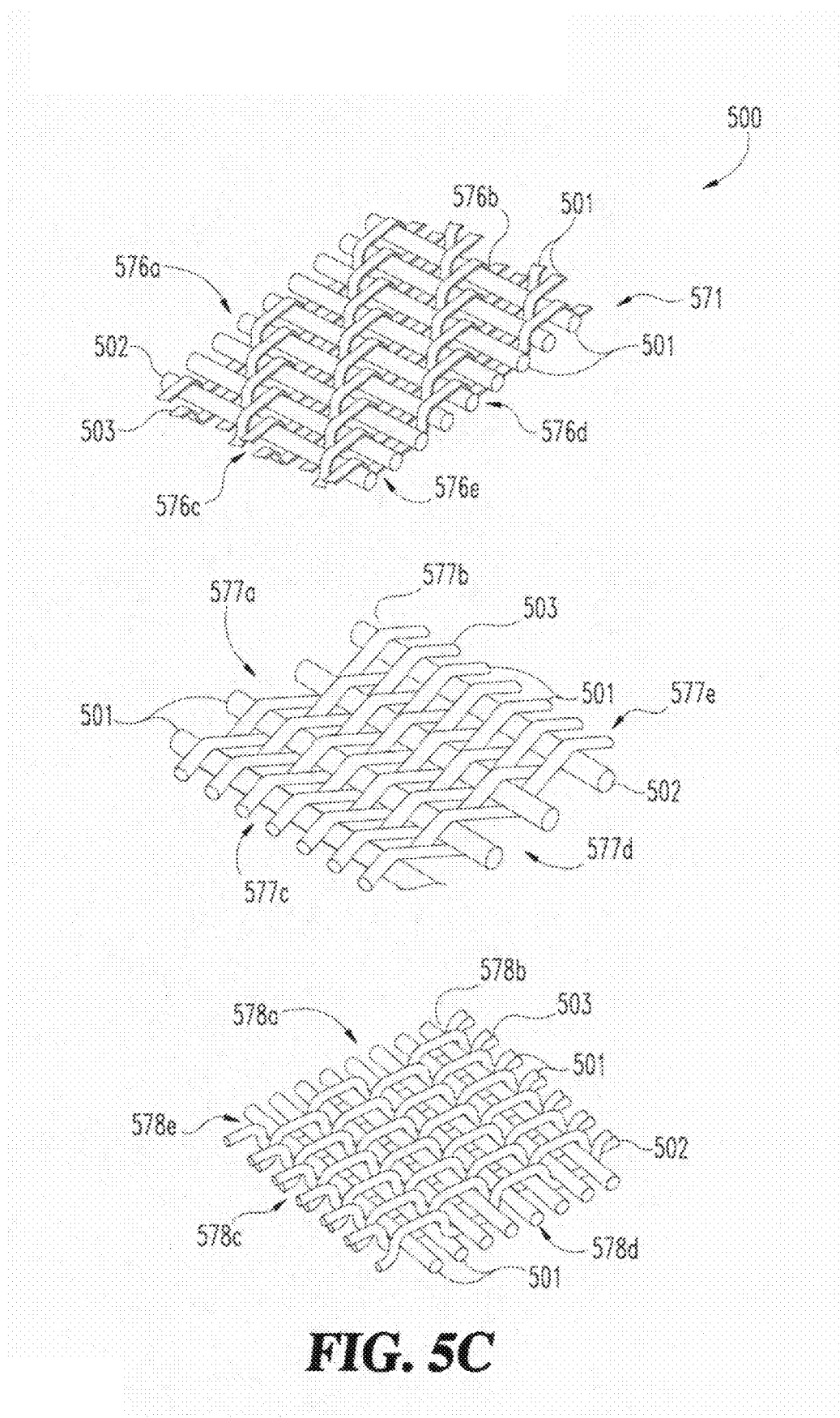
Figure 5D:
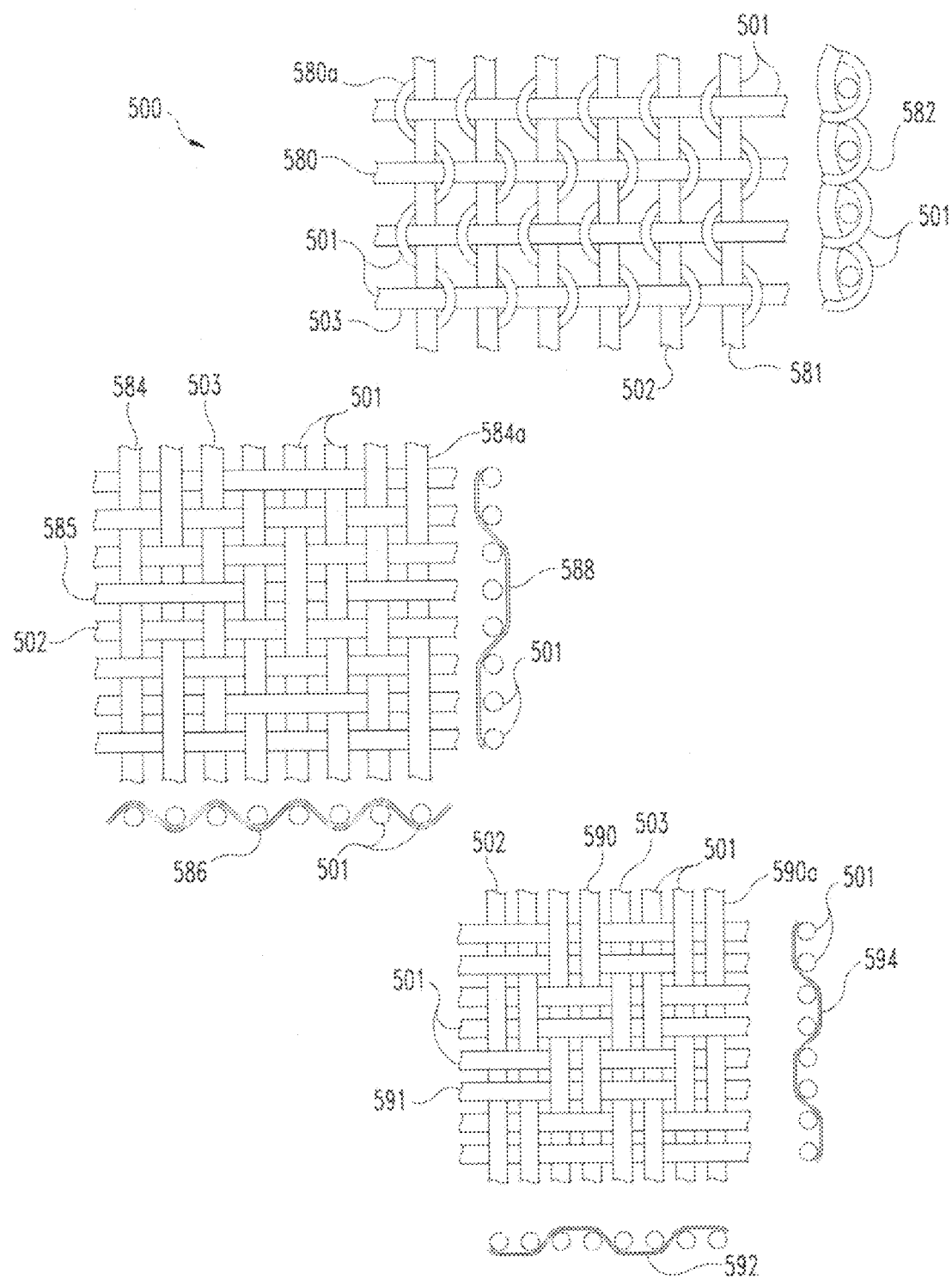

FIGS. 5 & 5A-5D schematically represent a comparison of different weave patterns with FIGS. 5A-5D in partial view form. FIG. 5 schematically depicts all the partial views of FIGS. 5A-5D to indicate relative orientation among them. FIG. 5A provides a partial, schematic view of a plain weave in the upper right corner and three different Harness Satin (HS) weaves: 4 HS weave (or "crowfoot" weave) in the upper left corner, a 5 HS weave in the lower right corner, and an 8 HS weave in the lower left corner; FIG. 5B provides a partial, schematic view of Five-Heddle (FHD) weave (upper), Herringbone weave (middle), and 3/3 twilled weave (lower); FIG. 5C provides a partial, schematic view of 2/2 twilled weave (upper), Dutch plain weave (middle), and Dutch twilled weave (lower); and FIG. 5D provides a partial, schematic view of Leno weave (upper) (more specifically a form of gauze weave), mock Leno weave (middle), and basket (panama) weave (lower). The weaves are depicted in FIGS. 5A-5D with disproportionate, exaggerated spacing between warp/weft constituents to enhance clarity. The partial views of FIGS. 5A, 5B, and 5D each depict a planar weave swatch and at least one representation of a sectional/edge perpendicular to the swatch plane. FIG. 5C is a view of weave patterns in perspective that conveys the same information as the swatch and sectional/edge representations of FIGS. 5A, 5B, and 5D.

Figure 1:
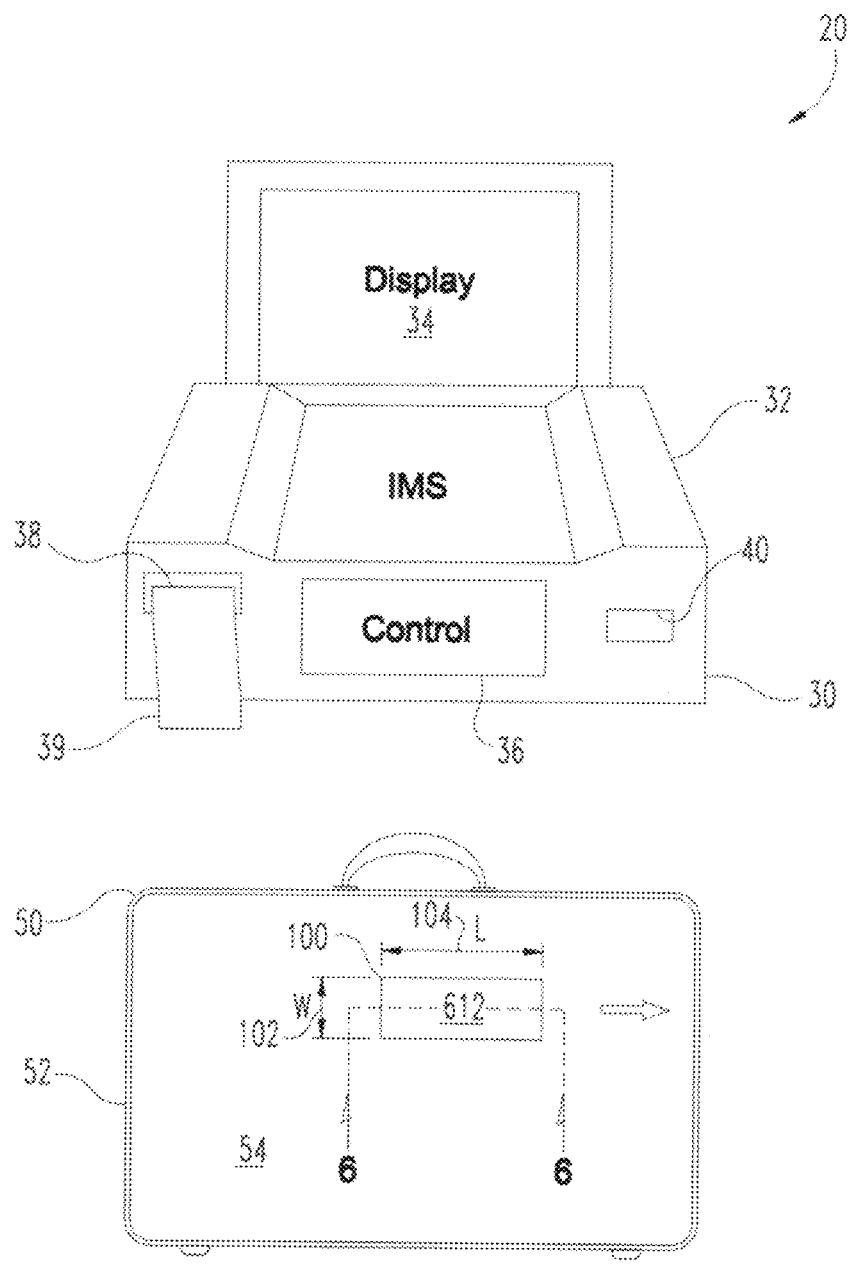
FIG. 1 depicts a partially diagrammatic view showing a sampler-based analyte processing system of one embodiment of the present application.

FIG. 6 is a partially diagrammatic, cross-sectional view of the sampler of FIG. 1 that corresponds to the section line 6-6 of FIG. 1, it further includes a partial cutaway that stair-steps down from the top toward the left side.

Figure 7:
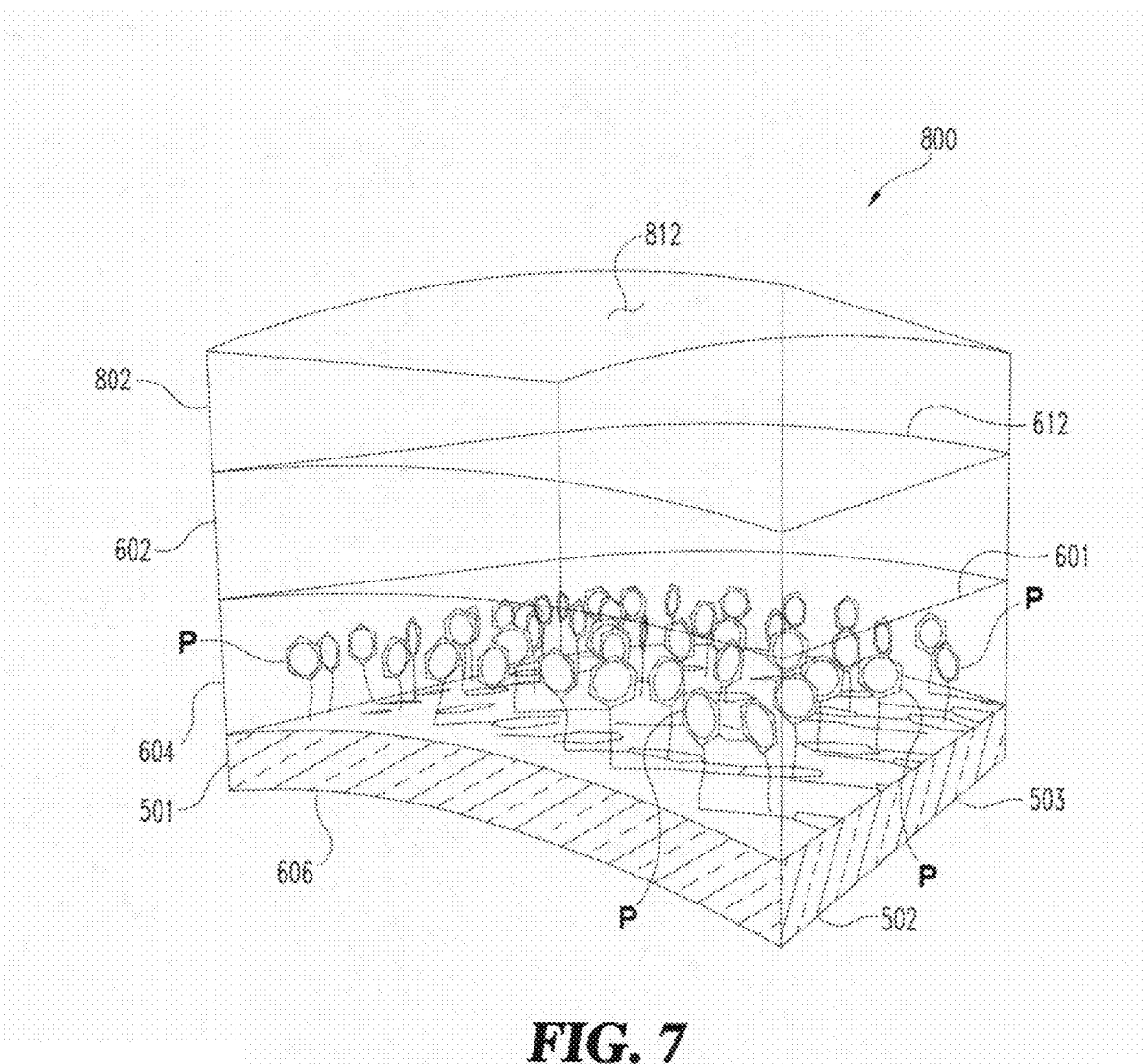

FIG. 7 is a schematic, perspective view of an alternative sampler depicting phenyl terminal groups in a functionalization sub-layer of the block-represented core fabric that is covered by multiple polymer layers.

Figure 8:
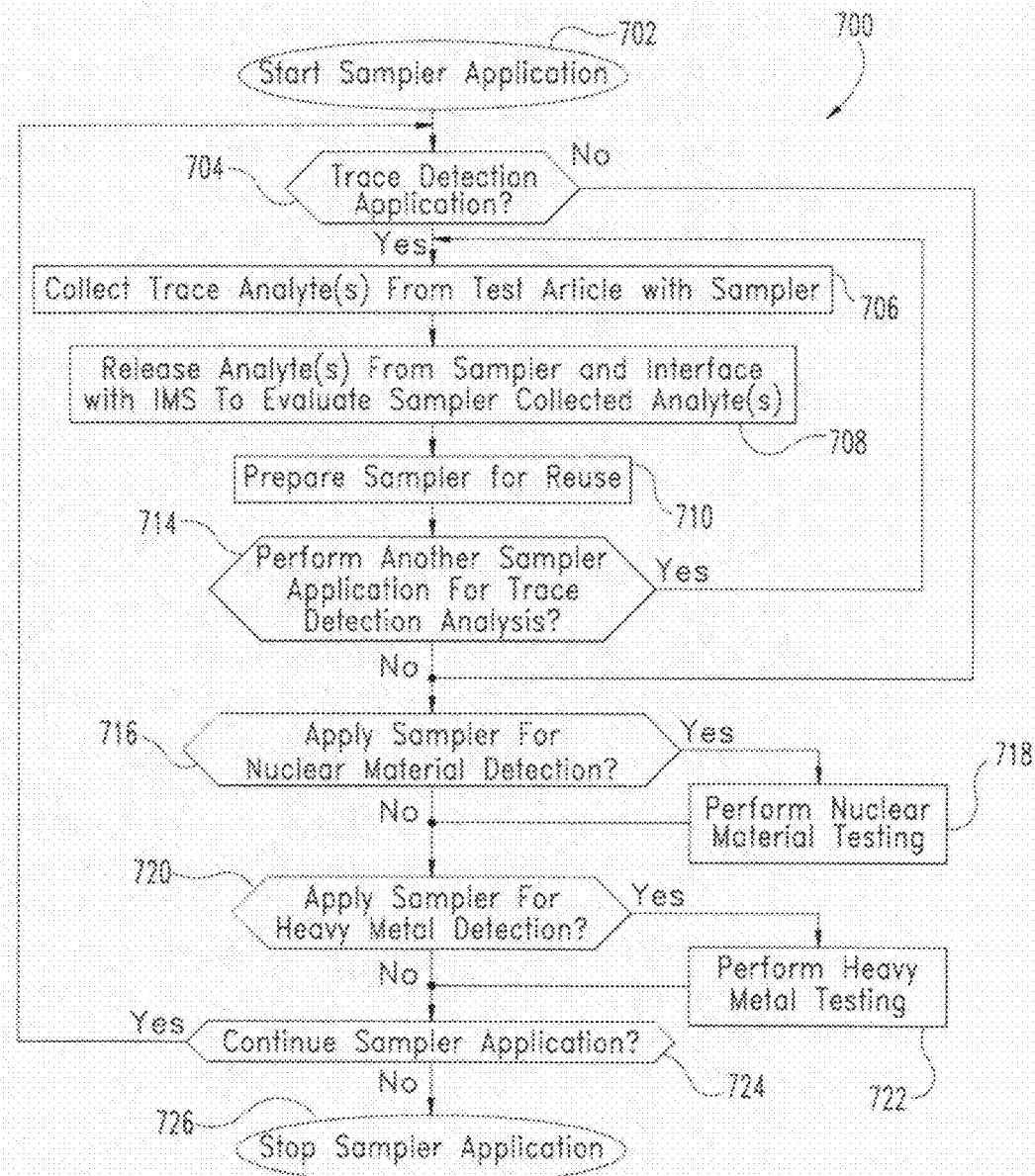

FIG. 8 is a flowchart representing one process for using a sampler according to the present application.

Figure 9:
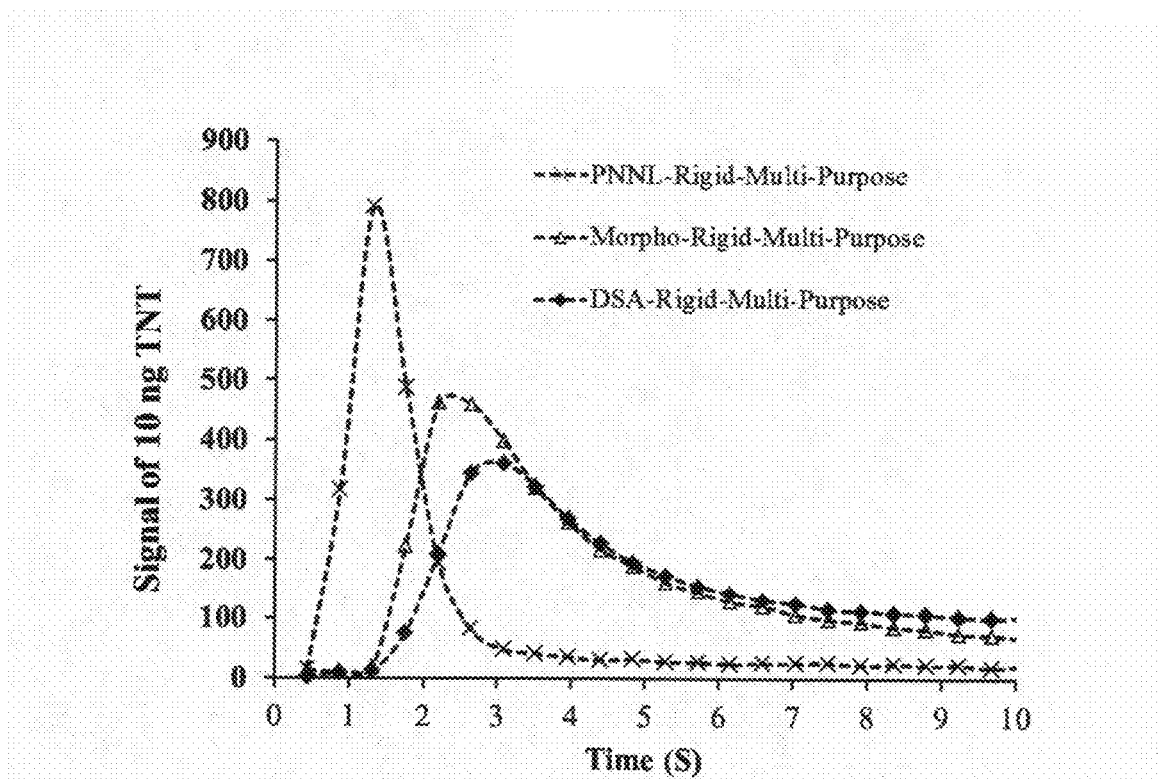

FIG. 9 is a comparative graph of magnitude versus time of three differently-sourced samplers each in response to a 10 nanogram (ng) TNT sample. In top-to-bottom order of the inset legend: the "X" data point plot represents the response of a sampler embodiment of the present application—it has the highest peak, the "hollow triangle" (Δ) data point plot represents the response of a SAFRAN MORPHO brand of sampler with an intermediate peak, and the "filled diamond" (♦) data point plot represents the response of a DSA DETECTION brand of sampler with the lowest peak.

Figure 10:
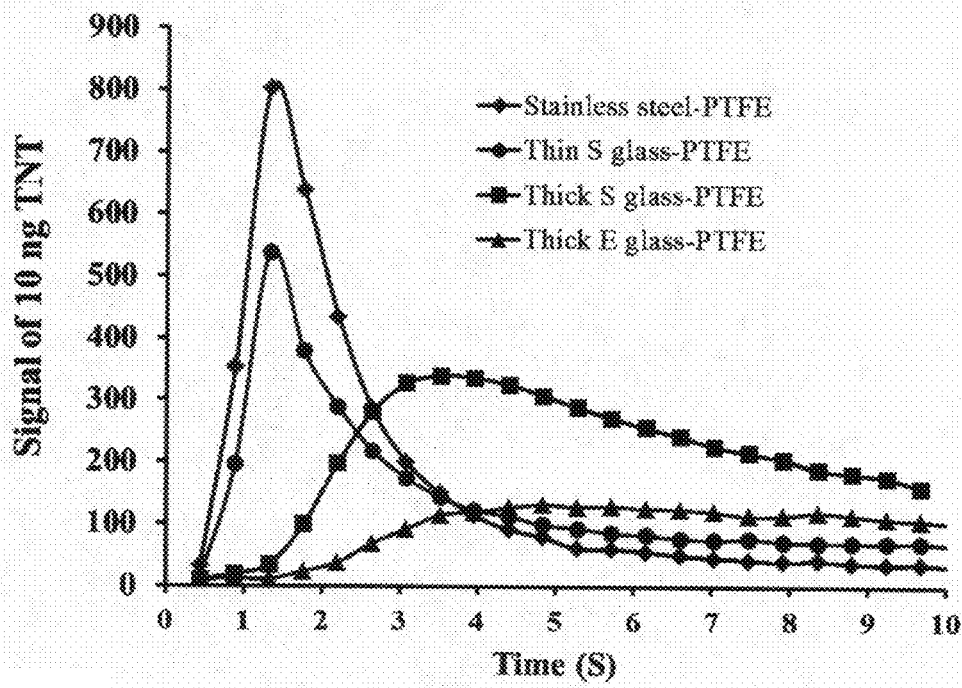

FIG. 10 is a comparative graph of magnitude versus time responses of four PTFE-coated samplers with different cores each to a 10 ng TNT sample. In top-to-bottom order of the inset legend: the "filled diamond" (♦) data point plot represents the response of a stainless steel core with the highest peak, the "filled circle" (●) data point plot represents the response of a thin S-glass core with the second highest peak, the "filled square" (■) data point plot represents the response of a thick S-glass core with the third highest peak, and the "filled triangle" (▲) data point plot represents the response of thick E-glass—it is the least responsive.

Figure 11:
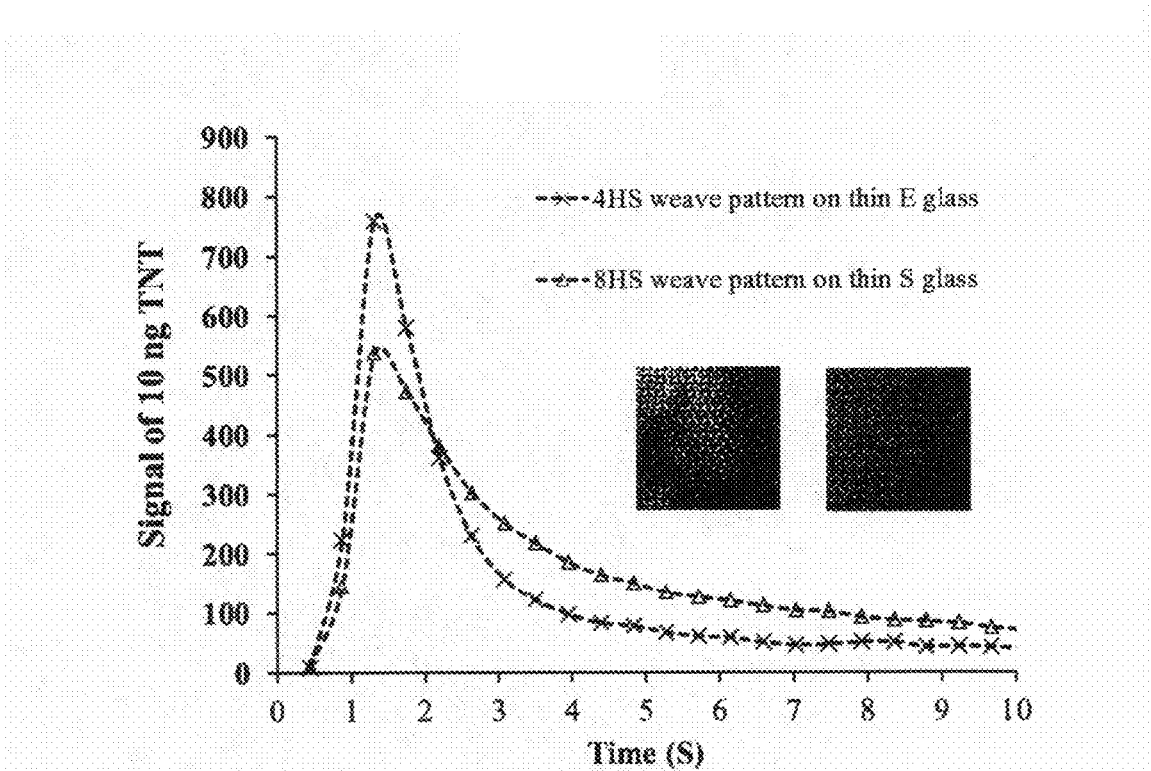

FIG. 11 is a comparative graph of magnitude versus time responses of two samplers with different fabric core weaves to a 10 ng TNT sample. In top-to-bottom order of the FIG. 11 inset legend: the "X" data point plot represents the response of a 4 HS weave pattern of thin E-glass with the highest peak, and the "hollow triangle" (Δ) data point plot represents the response of an 8 HS weave pattern of S-glass, which peaks at a slightly lower value. FIG. 11 includes inset computer-generated images of the 4 HS and 8 HS fabric weaves with like labeling.

Figure 12:
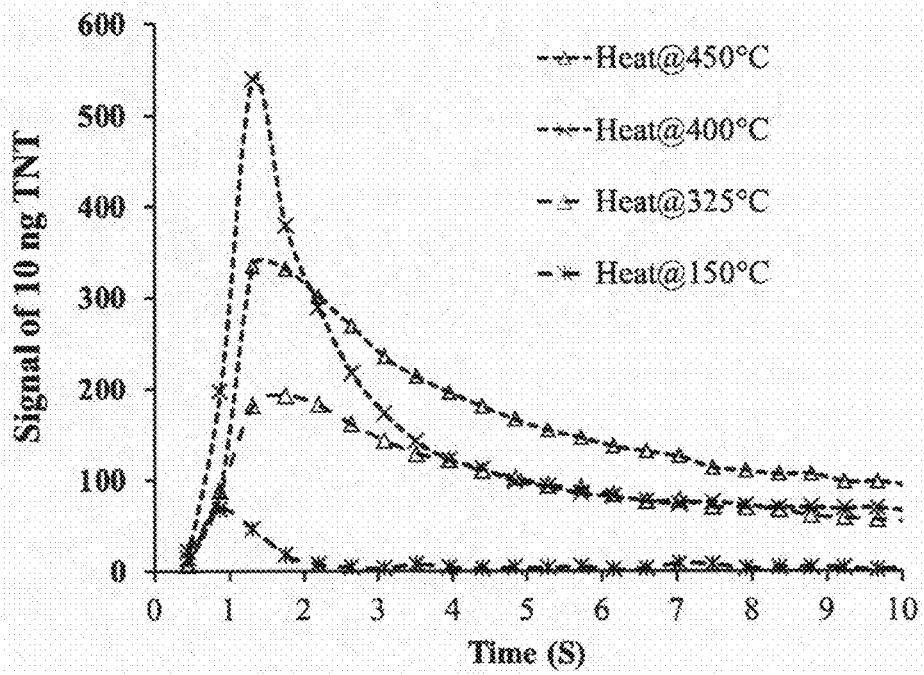

FIG. 12 is a comparative graph illustrating magnitude versus time responses of four samplers with different heat treatments each to a 10 ng TNT sample. In top-to-bottom order of the inset legend: the "hollow triangle" (Δ) data point plot represents the response to about a 450° C. heat treatment, with the second highest peak; the "X" data point plot represents the response to about a 400° C. heat treatment, with the highest peak; the "filled triangle" (▲) data point plot represents the response to about a 325° C. heat treatment, with the third highest peak; and the symbol of an "X" with a vertical line intersecting the "X" cross-point (similar to "*") provides a data point plot of the response to about a 150° C. heat treatment, with the lowest peak.

Figure 13:
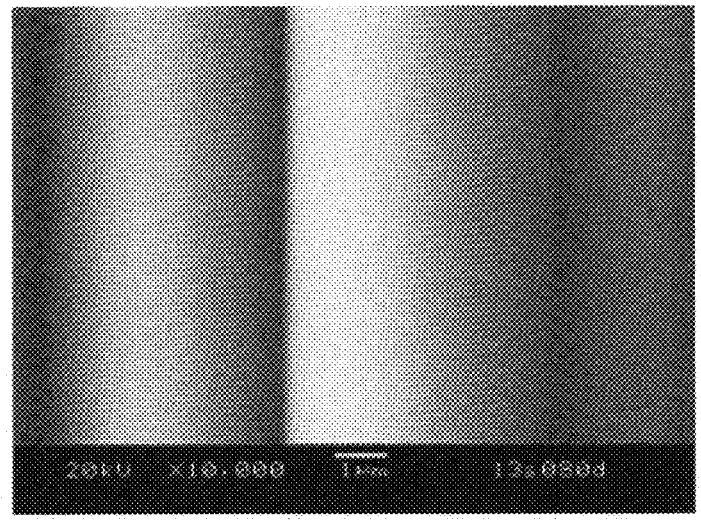

FIG. 13 is a computer-generated Scanning Electron Microscope (SEM) image of a PTFE-coated sampler with S-type fiberglass core after heat treatment at about a 150° C.

Figure 14:
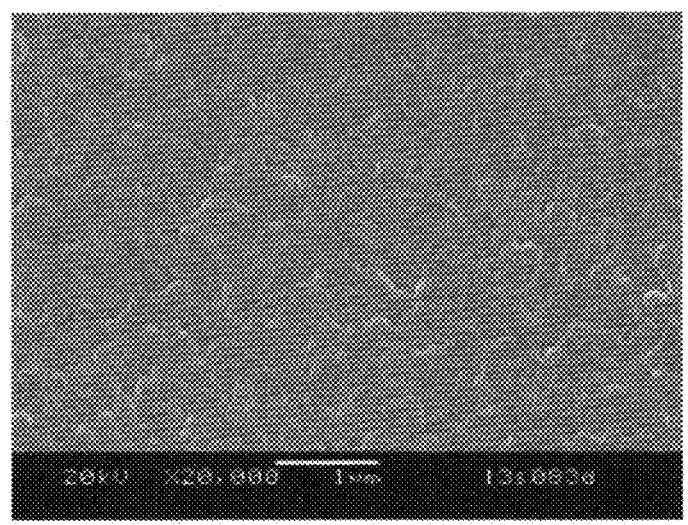

FIG. 14 is a computer-generated SEM image of a PTFE-coated silicon wafer after heat treatment at about 150° C. for comparison to FIG. 13.

Figure 15:
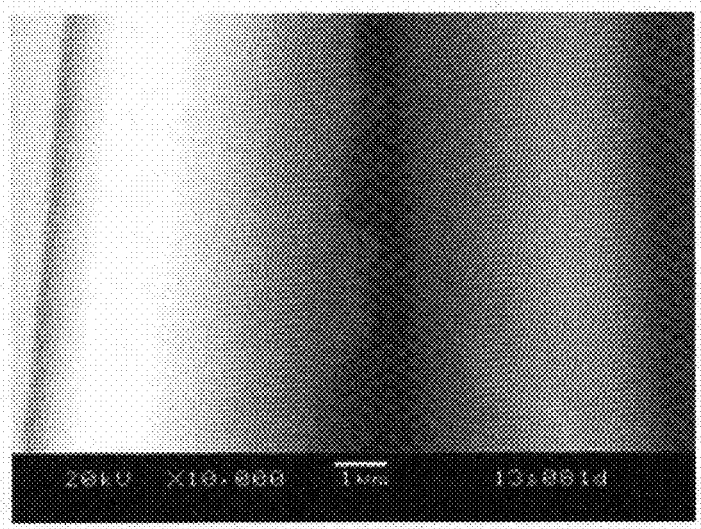

FIG. 15 is a computer-generated SEM image of a PTFE-coated fabric sampler with an S-type fiberglass core after heat treatment at about 325° C.

Figure 16:
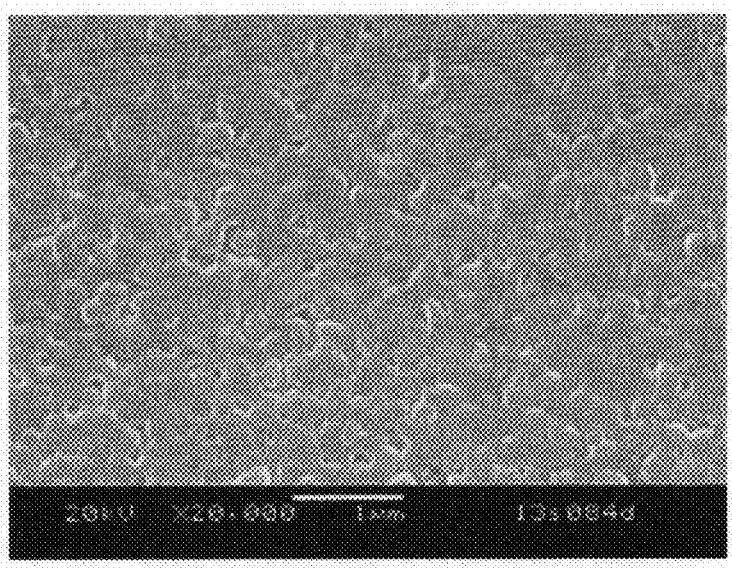

FIG. 16 is a computer-generated SEM image of a PTFE-coated silicon wafer after heat treatment at about 325° C. for comparison to FIG. 15.

Figure 17:
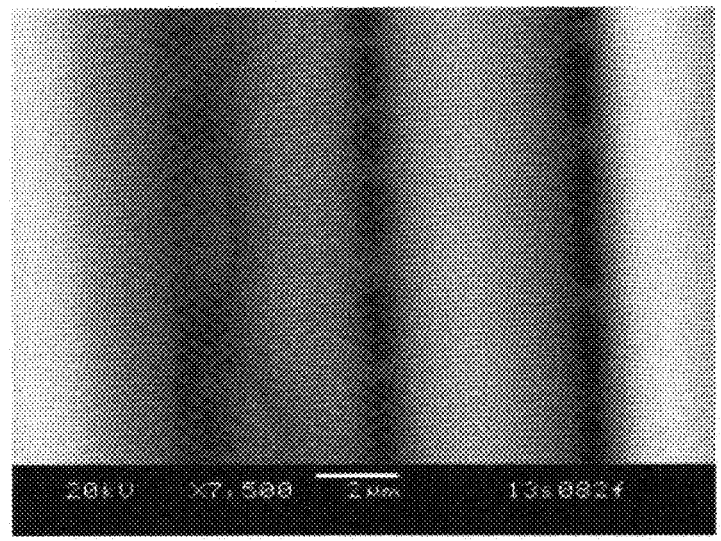

FIG. 17 is a computer-generated SEM image of a PTFE-coated fabric sampler with an S-type fiberglass core after heat treatment at about 400° C.

Figure 18:
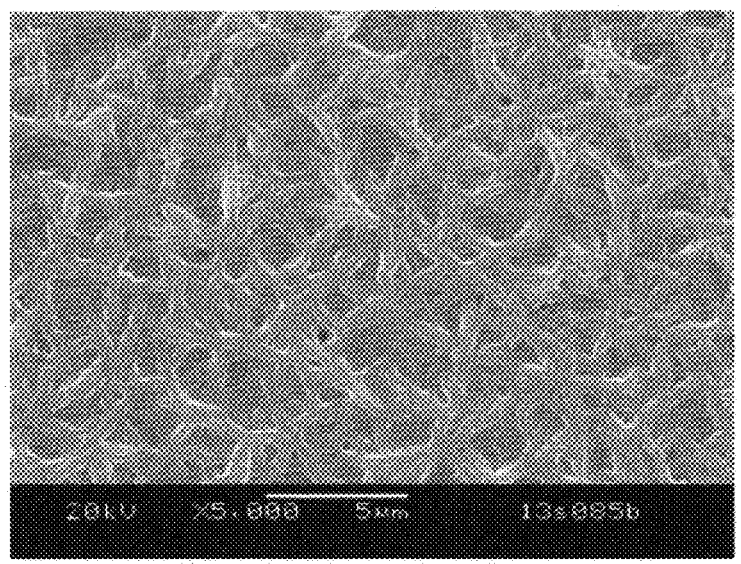

FIG. 18 is a computer-generated SEM image of a PTFE-coated silicon wafer after heat treatment at about 400° C. for comparison to FIG. 17.

Figure 19:
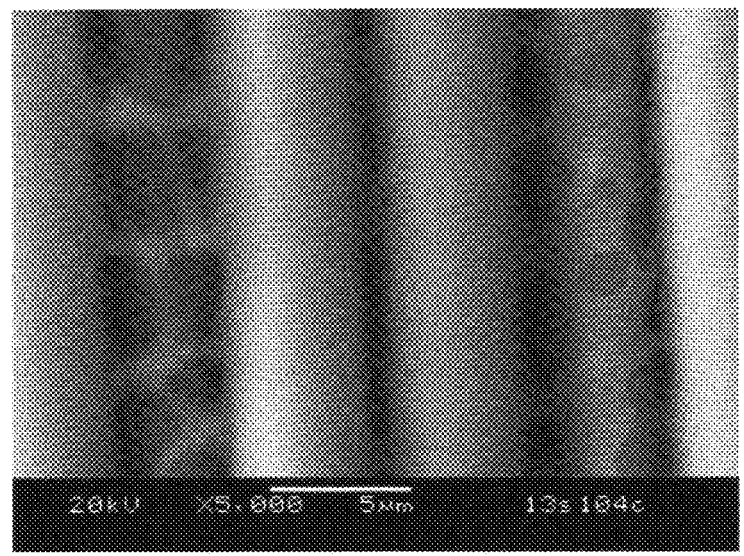

FIG. 19 is a computer-generated SEM image of a PTFE-coated fabric sampler with an S-type fiberglass core after heat treatment at about 450° C.

Figure 20:
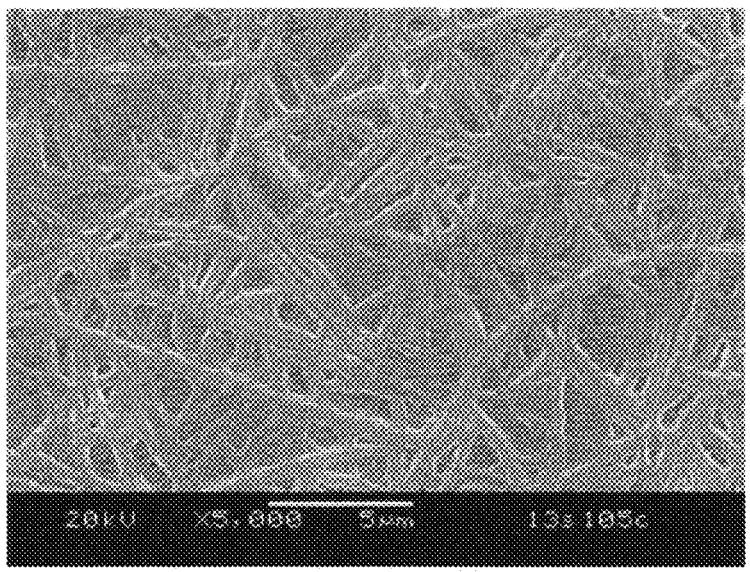

FIG. 20 is a computer-generated SEM image of a PTFE-coated silicon wafer after heat treatment at about 450° C. for comparison to FIG. 19.

Figure 21:
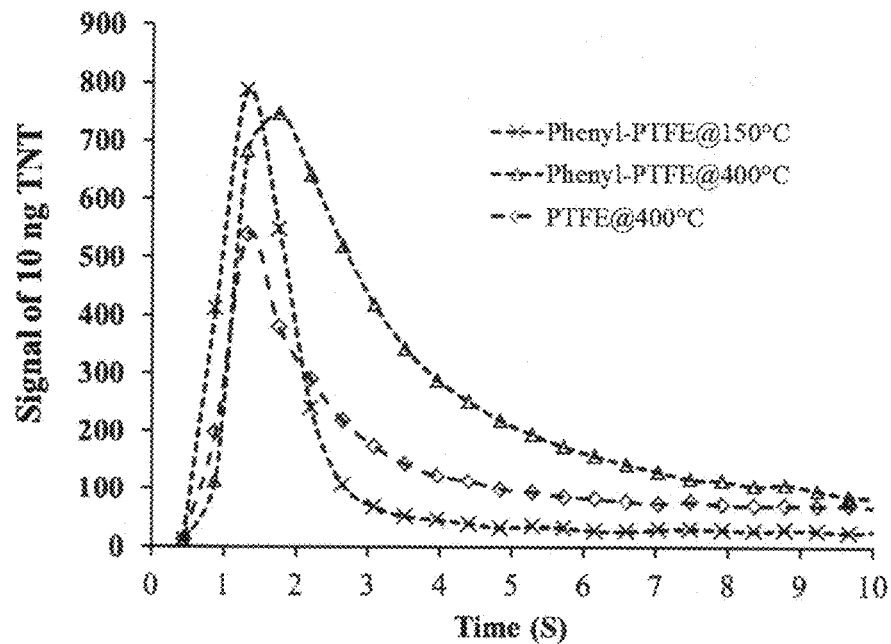

FIG. 21 is a comparative graph of magnitude versus time responses of each of three different PTFE-coated, S-type fiberglass core samplers, with and without phenyl surface functionalization, to a 10 ng TNT sample. In top-to-bottom order of the inset legend: the "X" data point plot represents the response of a Phenyl-PTFE sampler heat-treated at about 150° C.—it has the highest peak, the "hollow triangle" (Δ) data point plot represents the response of a Phenyl-PTFE sampler heat-treated at about 400° C.—it has an intermediate peak, and the "hollow diamond" (◊) data point plot represents the response of a PTFE sampler (no phenyl or other functionalization type) heat-treated at about 400° C.—it has the lowest peak.

Figure 22:
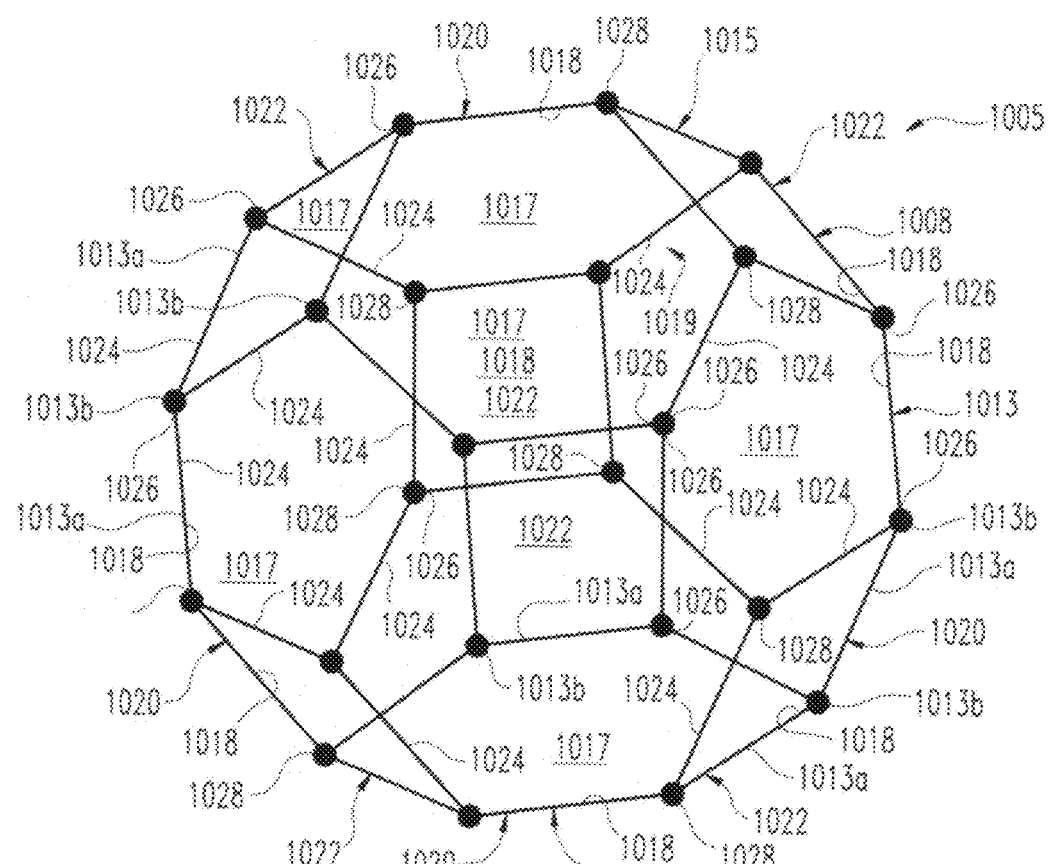
Figure 24:
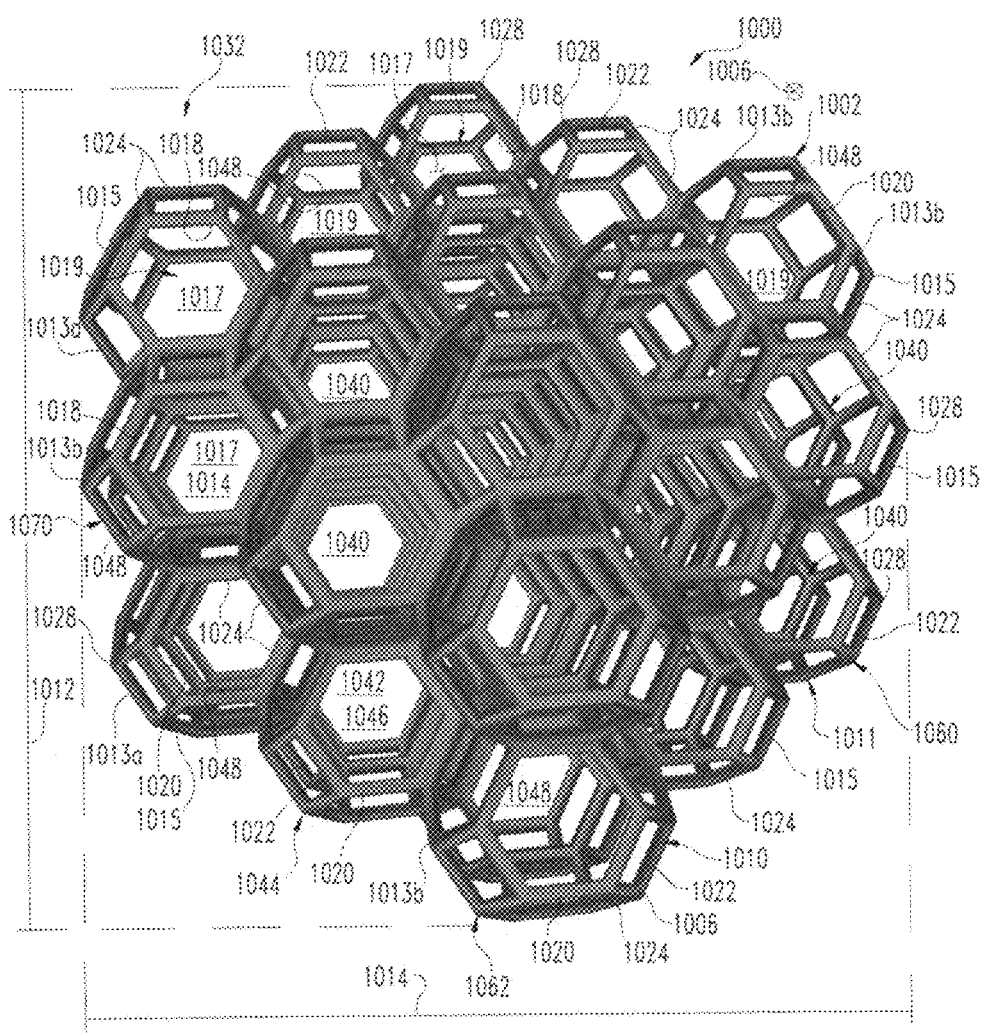
Figure 25:
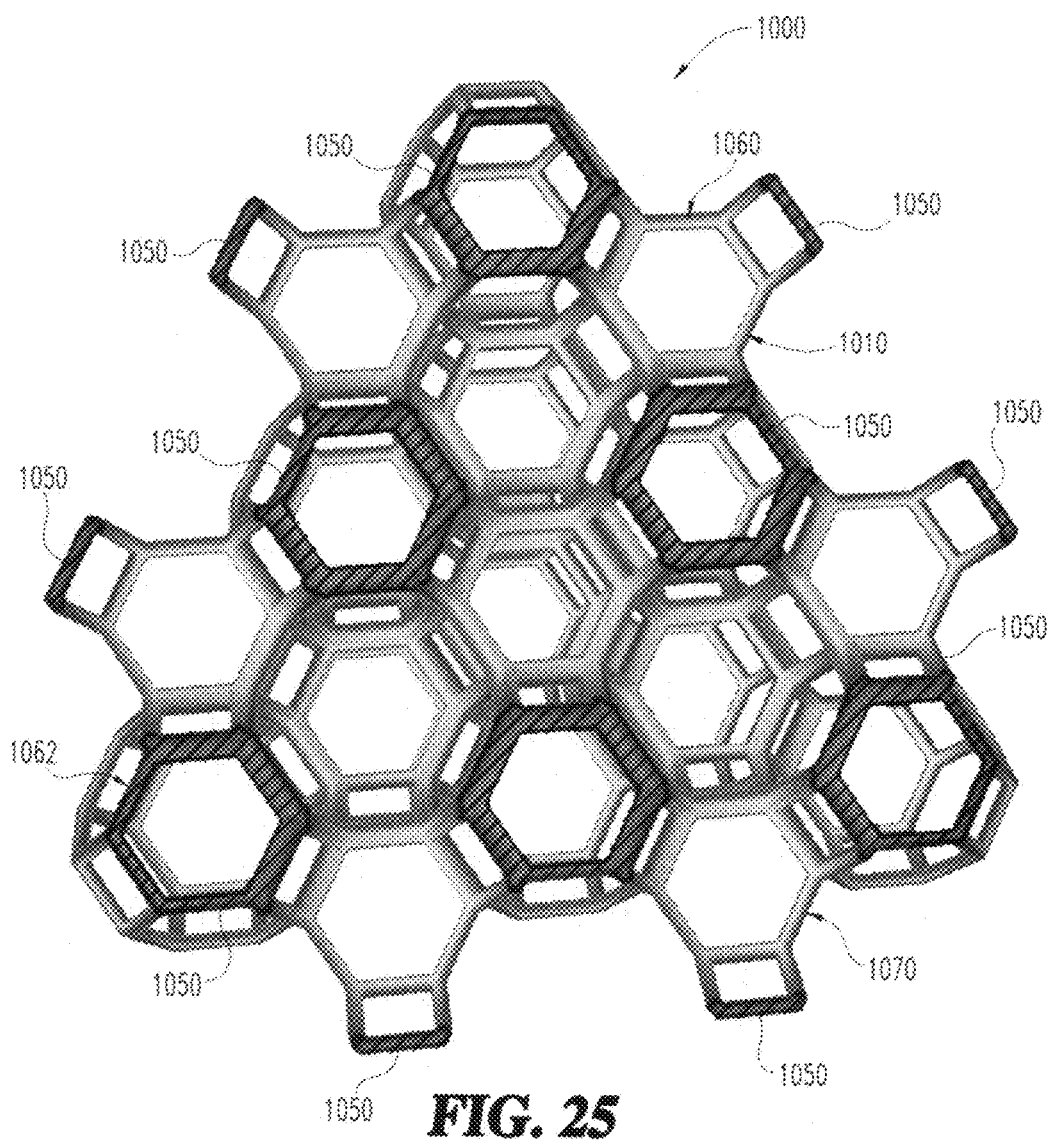

FIG. 22 is a diagrammatic, perspective view of a framework structure outlining the shape of a truncated octahedron and corresponding to an introductory, conceptual constituent of a substance collection framework of a 3-D (three-dimensional) sampler further shown in FIGS. 24 & 25.

Figure 23:
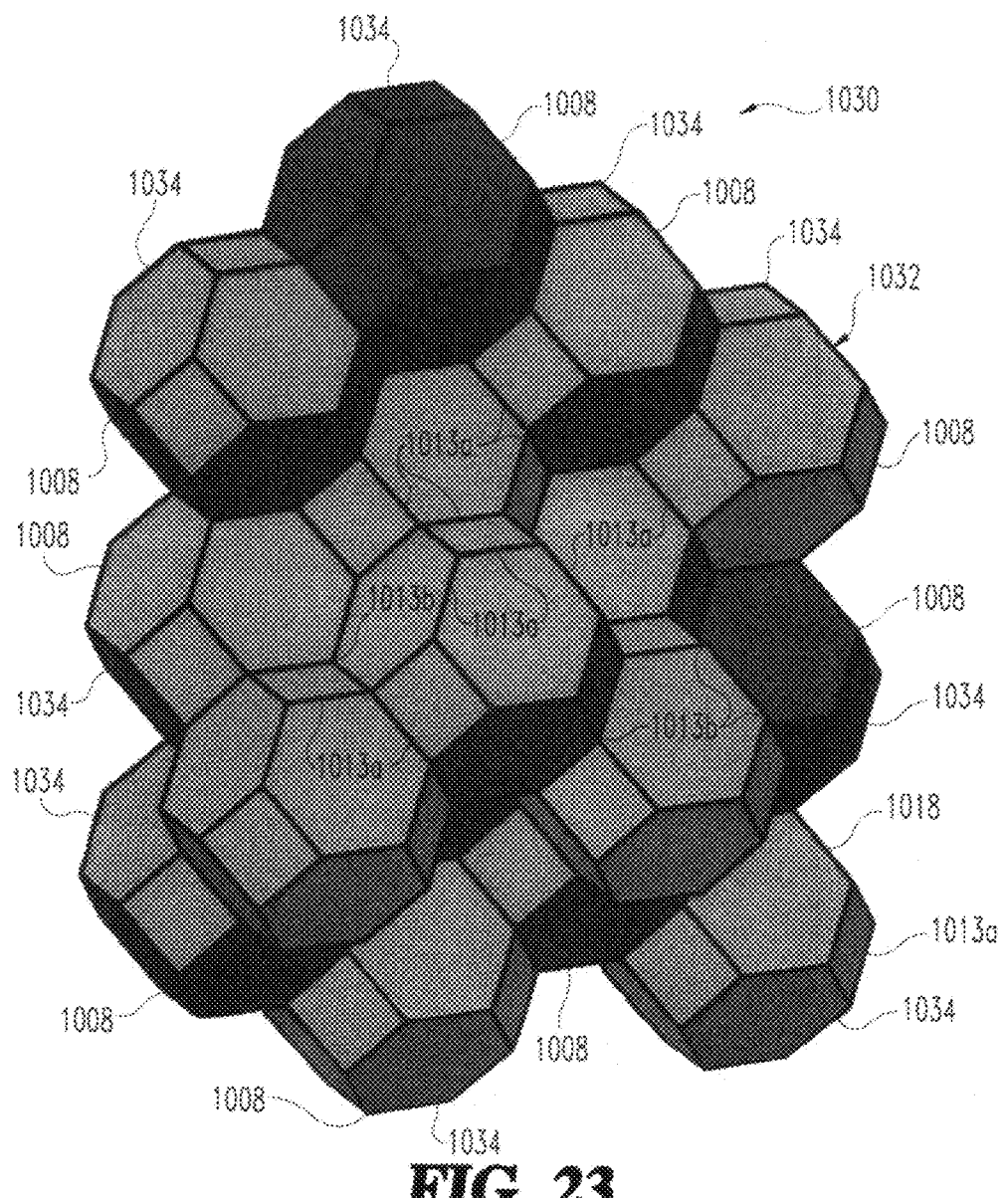

FIG. 23 is a diagrammatic, perspective view of a solid geometry representation of a bitruncated cubic honeycomb form of tessellation. FIG. 23 serves as a conceptual bridge from the framework structure of FIG. 22 to the collection framework of FIGS. 24 & 25. The bitruncated cubic honeycomb of FIG. 23 may be described as an arrangement of a number of coincident, solid truncated octahedral blocks. Each of these blocks correspond to the truncated octahedral shape outlined by the framework structure shown in FIG. 22. These truncated octahedral blocks are geometrically coincident and arranged so they merge along coincident pairs of edges and vertices where brought together to correspond to the honeycomb. As is common in the art, this figure is provided with grayscale shading to enhance clarity of three-dimensional aspects thereof.

FIG. 24 is a diagrammatic, perspective view of an openwork, 3-D, lattice/cage-like substance collection sampler with a collection framework that corresponds to an open form of a bitruncated cubic honeycomb arrangement conceptually introduced in FIGS. 22 & 23. This FIG. 24 arrangement is of the same general type shown in FIG. 23; however, the number of coincident truncated octahedral-shaped constituents and the overall shape differ. As is common in the art, this figure is provided with grayscale shading to enhance clarity of three-dimensional aspects thereof.

FIG. 25 is a diagrammatic, perspective view of a cross-sectioned portion of the three-dimensional sampler framework shown in FIG. 24—the cross-section being taken along a sectional plane approximately parallel to the view plane of FIG. 24. As is common in the art, this figure is provided with grayscale shading to enhance clarity of three-dimensional aspects thereof.

Figure 26:
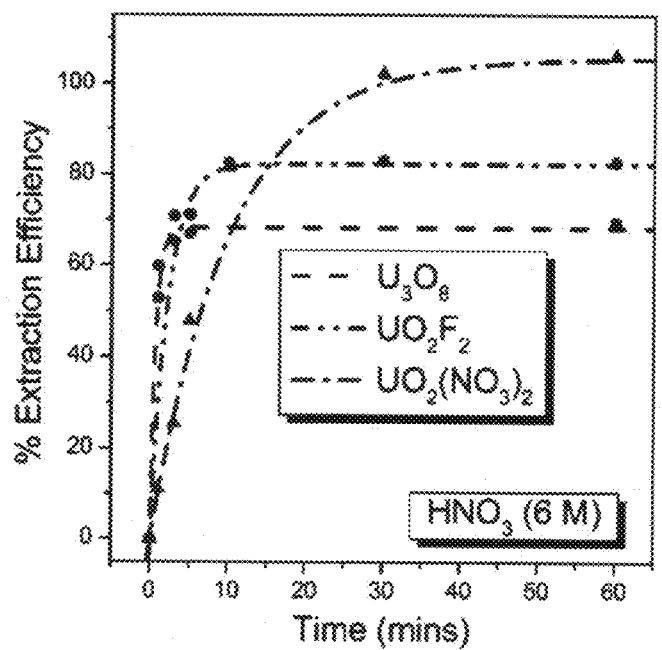

FIG. 26 is a comparative graph of percent (%) extraction efficiency versus time for three different uranium compounds: uranium oxide ($U_3O_8$), uranyl fluoride ($UO_2F_2$), and uranyl nitrate ($UO_2(NO_3)_2$)—each of these compounds being extracted from a respective PTFE-coated sampler with 6.0 molar (M) nitric acid aqueous solution. In top-to-bottom order of the inset trend line legend: the uniform dashed/hidden line style "- - -" represents a trend line plot for the response of $U_3O_8$, the phantom/cutting plane line style "- ·· -" represents a trend line plot for the response of $UO_2F_2$, and the chain/center line style "- ·- " represents a trend line plot for the response of $UO_2(NO_3)_2$.

Figure 27:
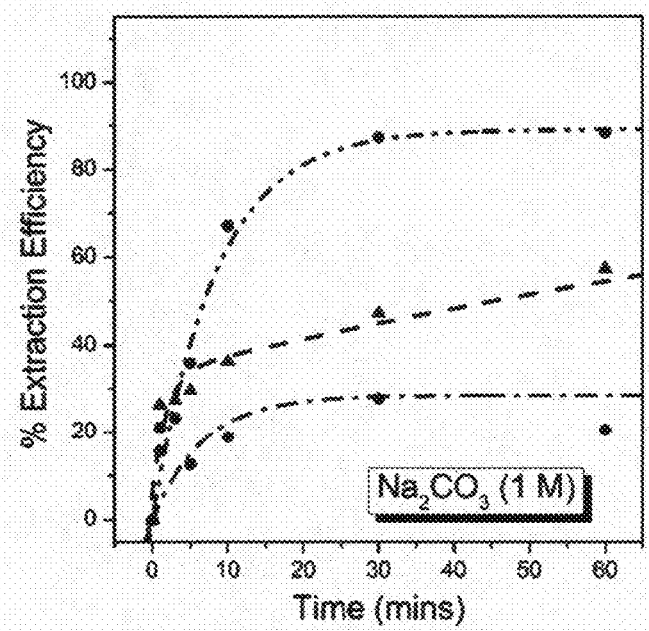

FIG. 27 is a comparative graph of percent (%) extraction efficiency versus time for the three different uranium compounds of FIG. 26—each of these compounds being extracted from a respective PTFE-coated sampler with a 1.0 M sodium carbonate aqueous solution. The same legend applies as described for FIG. 26.

Figure 28:
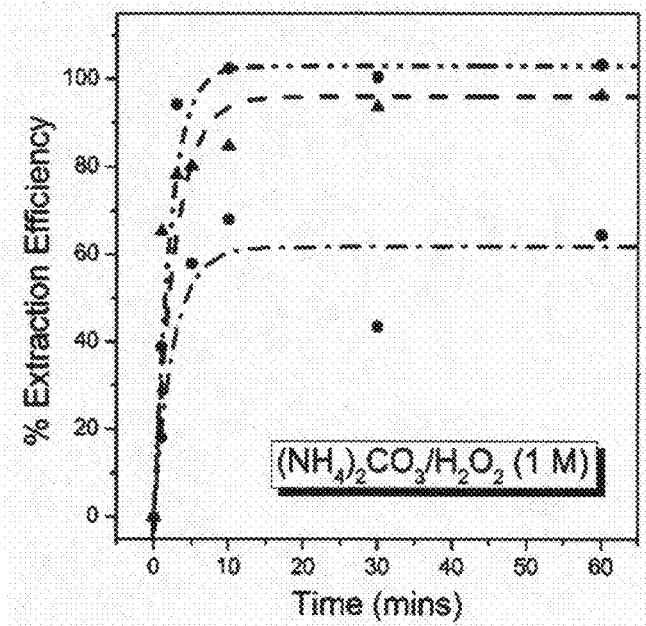

FIG. 28 is a comparative graph of percent (%) extraction efficiency versus time for the three different uranium compounds of FIG. 26—each of these compounds being extracted from a respective PTFE-coated sampler with a mixture of 1.0 M ammonium carbonate and 1.0 M hydrogen peroxide in aqueous solution. The same legend applies as described for FIG. 26.

DETAILED DESCRIPTION OF REPRESENTATIVE EMBODIMENTS

In the following description, numerous specific details are given to provide a thorough understanding of the embodiments. One skilled in the relevant art will recognize, however, that the invention(s) of the present application can be practiced without one or more of the specific details, or with other methods, processes, compositions, arrangements, configurations, kits, systems, devices, apparatus, components, materials, etc. In other instances, well-known structures, materials, or operations are not shown or described in detail to avoid obscuring aspects of the invention. Thus, for the purposes of promoting an understanding of the principles of each invention described or claimed herein, reference is made to representative embodiments illustrated in the drawing(s) and specific language is used to describe the same. Any changes, alterations, variations, modifications, reconfigurations, substitutions, implementations, differences, substitutions, and applications of the principles of the same as described herein are contemplated that would normally occur to one skilled in the art to which they relate and/or that would become apparent from the description and figures provided herewith—without departing from the scope of the invention as set forth in the claims listed hereafter. By way of nonlimiting example, in certain instances the description refers to exemplary explosive (like TNT), core composition (like S-glass), and/or polymer applied to the core (like PTFE); however, the inventions defined by the claims are intended to cover any alternatives expressed therein or covered thereby including any equivalents thereof. Accordingly, this description of representative embodiments should be seen as illustrative only and not limiting the scope of any invention described and/or claimed herein.

Among the embodiments of the present application are unique trace analyte samplers, sampler kits, sampler devices, related systems, and methods of designing, making and using samplers—including, but not limited to release, removal, and/or extraction of analyte(s) of interest from a sampler. One sampler form includes a fabric substrate with a selected thickness to which a polymer is applied to provide a selected degree of stiffness/rigidity. The sampler stiffness can be expressed in terms of flexural modulus, among other things, which can be controlled through the amount of polymer applied to the fabric substrate and heat treatment thereof. In some forms, a sampler core support structure is comprised of one or more of: polymeric thermoplastic, polymeric thermoset, glass, metal, metalloid, inorganic oxide, ceramic, and glass-ceramic. The core can have silane ligands bonded thereto for more reliable release of analyte(s) and/or to improve polymer application thereto. Alternatively or additionally, a sampler embodiment with a woven fiber core has a closed weave, thermally conductive particles added to the core; multiple polymer layers formed on the core, and/or at least one layer of the polymer applied is comprised of one or more of: polymeric organofluorine, polyamide, polyimide, PBI, PDMS, PFSA, and PPPO.

FIG. 1 depicts another embodiment of the present application in the form of analyte processing system 20. System 20 is of a type that may be used in an airport, train station, shipping port, or the like to perform security screening for contraband or undesirable substances. System 20 includes analyte trace detection instrumentation 30, test article 50, and analyte collection sampler 100. Sampler 100 is of a thin, planar configuration. Instrumentation 30 includes a form of thermal desorption Ion Mobility Spectroscopy/Spectrometer (IMS) detector 32, and the test article 50 is further designated as being of a suitcase 52 form. Test article 50 includes outer surface 54 that may be smooth or rough to either extent as might be expected for a standard suitcase 52. However, in other embodiments, a different type of test article 50 may include one or more different surface qualities.

IMS detector 32 includes: operator display 34 to display relevant information regarding its operation; operator input control 36 in the form of a keyboard, touchscreen, mouse-like pointers, voice-activation interface, touch keys, membrane switches, press buttons, sliders, toggle/rotary switches, dials, a combination of these, or the like; and integral printer 38 with a print-out sheet 39 generated thereby. In addition to display 34, print-outs 39 from printer 38 can be used to inform the operator of results of analysis performed with instrumentation 30; and instrumentation 30 may further be supplemented by an aural-output device to provide warnings, instructions, and the like. Print-out 39 further provides a written record of the testing performed with system 20. IMS detector 32 further includes sampler slot 40, in which sampler 100 can be inserted for the release and transfer of collected analyte(s) by thermal desorption into IMS detector 32 for analysis as further described hereinafter.

A different arrangement of operator input/output (I/O) may be provided such that there may be additional or alternative I/O devices with respect to display 34, printer 38, and control 36. By way of nonlimiting example, display 34 may be a touchscreen type without separate input control 36. IMS detector 32 embodiments are of any type suitable to sufficiency process samples, including, for example: suitable models of IMS-based equipment from SARFAN MORPHO, SMITHS DETECTION, or another supplier; and instrumentation combinations of IMS with other detector types, such as High-Performance Liquid Chromatography (HPLC), and the like. In still other embodiments, sampler 100 is utilized with non-IMS detection equipment with appropriate alterations (if any) to provide for proper analyte transfer/release and processing. Such alternatives to IMS include: Thermal Desorption Gas Chromatographs (TD-GCs) and other GC types; liquid chromatography (LC) instrumentation; X-Ray Fluorescence (XRF); Inductively Coupled Plasma Mass Spectrometry (ICP-MS); gamma, beta, and alpha spectrometers and counting devices; Mass Spectrometry (MS) instrumentation; and combinations of these various instruments including, e.g., Thermal Desorption Gas Chromatography Mass Spectrometers (TD-GCMS) and Headspace Analyzer Gas Chromatography Mass Spectrometers (HA-GCMS). Furthermore, instrumentation 30 may employ IMS or other equipment that receives sampler-released analyte(s) in a manner other than thermal desorption—such as, analyte(s) released by sampler rinsing and/or other application of one or more agents from which a detector sample is prepared. Any sample preparing rinse(s) and/or agent(s) can be of any type suitable for the sampler type, substance(s) being detected, and sample composition requirements of the instrumentation used to detect such substance(s). In one example, an aqueous solution is used to rinse the sampler and prepare the sample, and may be acidic or basic to a degree desired to facilitate sample preparation. In yet another form, a mixture of an oxidizer (like hydrogen peroxide) and one or both of: onium and carbonate (like ammonium carbonate) in aqueous solution is utilized. Alternatively or additionally, one or more organic solvents may be used to prepare the sample. To the extent a rinse, solution, and/or solvent is utilized, some form of agitation may be employed to facilitate analyte release/extraction such as stirring, shaking, scrubbing, or the like. A Barringer IONSCAN 400A IMS (SMITHS DETECTION) was utilized in the following experimental examples 1-10, and is among the embodiments of IMS detector 32.

Sampler 100 is shown in a wiping/swiping position as applied to surface 54 of suitcase 52 with an arrow indicating direction of the wipe/swipe motion to the right. The width W of sampler 100 along its longitude is indicated by double-headed arrow 102 and the length L of sampler 100 is indicated by double-headed arrow 104. FIG. 1 includes section line 6-6 through sampler 100, with a corresponding cross-sectional view of sampler 100 set forth in FIG. 6 to be discussed further hereinafter.

Figure 2:
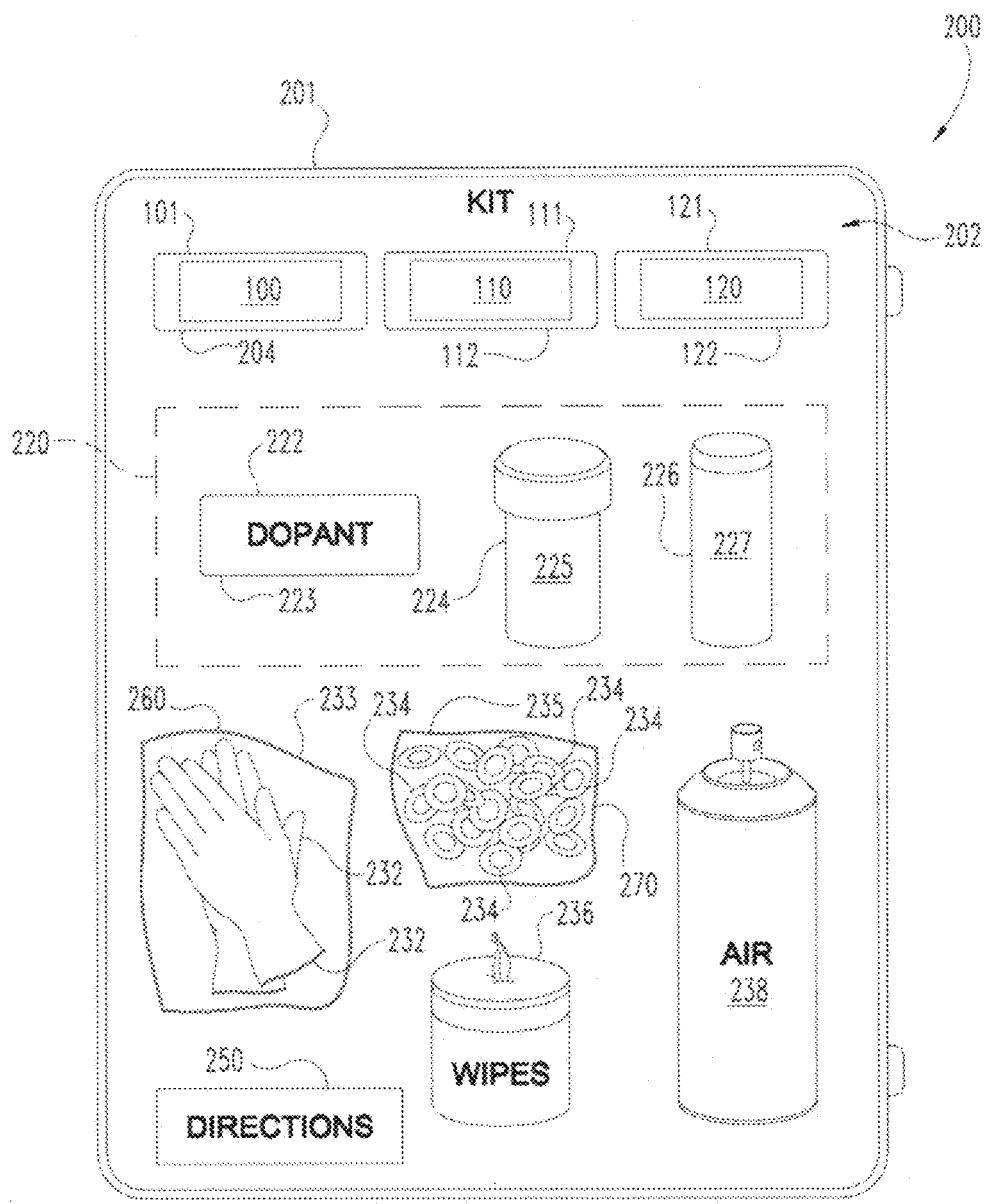
FIG. 2 depicts a partially diagrammatic view illustrating a sampler kit that can be used with the system of FIG. 1.

FIG. 2 illustrates kit 200 for use with system 20; where like reference numerals refer to like features previously described. Kit 200 includes consumable materials that may be desired to perform testing with detector 32. All the items 202 of kit 200 may be provided together as shown in the depicted embodiment, or alternatively provided as a subset of two or more items 202. Such multiple-item subsets also each constitute a type of "kit" as used herein. Kit 200 includes an outer container and/or packaging 201 that encloses various kit items 202. Various kit 200 instructions/directions may be provided on a surface of packaging 201 or on an inner surface, or separate sheet or card provided with kit 200 that may be self-contained and/or may refer to an online, computer network accessible website as an additional or alternative source for some or all of any remaining instruction, direction, and/or any update thereto.

Specifically, kit 200 includes multiple samplers 100 packaged together in container/package 101 that standing alone is also a form of kit. Container/package 101 includes related reference, instruction, and/or direction 204 regarding use, warnings, or the like printed on its surface. Samplers 100 may further include identifying marking, reference, instruction, and/or direction description directly thereon. Alternatively or additionally, some or the remainder of such information may be separately sourced from a sheet/card, packaging/container surface, website, or the like as previously described in connection with kit 200 and packaging 201. Package 111 includes multiple calibration strips 110 with approximately the same form factor as samplers 100. Package 111 includes related reference, marking, and/or directions 112 specific to calibrations strips 110 regarding use, warnings, or the like. Strips 110 include a predefined type/quantity of substance to calibrate detector 32. Package 121 also includes multiple verification strips 120 with approximately the same form factor as samplers 100. Package 121 includes related reference, marking, and directions 122 specific to verification strips 120 regarding use, warnings, or the like printed on its surface. Strips 120 include a predefined type/quantity of substance to verify proper calibration of detector 32 and can include identifying marking and direction description pertinent to the same. Samplers 100, strips 110, and/or strips 120 packaged in corresponding containers 101, 111, 121 comprise a subset of detector 32 interface consumables, and each constitutes a kit individually, as do two or more provided collectively. Strips 110, 120 and/or package/container 111, 121 may additionally or alternatively provide separate sourcing of some or the remainder of instruction/direction information as previously described in connection with kit 200, samplers 100 and corresponding package and/or container.

Kit 200 also includes a subset of IMS consumables 220 directed to replacement chemicals and hardware for detector 32. Without limitation, IMS consumables 220 include dopant 222 with directions 223 regarding identity, use, warnings, or the like. In other embodiments, multiple types of dopant may be included or obtained by kit or otherwise. IMS consumables 220 further include IMS membranes 224 with directions 225 regarding identity, use, warnings, or the like; and IMS filters 226 with directions 227 regarding identity, use, warnings, or the like. Alternatively or additionally, IMS consumables 220 may include specialized tools, O-rings, spare parts kits, a packet of sample collection envelopes, maintenance/log books, fuses, dryer material, printer paper, analyte sampler release agent(s), and/or printer ink—just to name a few examples. Kit 200 further includes operator gloves 232 contained in packaging 233. Packaging 233 includes related directions 260 regarding identity, use, warnings, or the like. Gloves 232 are worn by operators to reduce the chance of contamination when collecting and handling samplers 100, or strips 110, 120. Also included in kit 200 is a package 235 of finger cots 234 that may be used as an alternative to gloves 232. Package 235 includes related directions 270 regarding identity, use, warnings, or the like. Kit 200 also includes cleaning devices 236 in the form of a roll or other arrangement of multiple alcohol-soaked wipes to remove dirt, debris, and other detritus from equipment and desired/surfaces likely to contaminate the sampling process. In other embodiments, different cleaning items may be alternatively or additionally included, such as cleaning swabs, separately packaged wipes, cleaning cloths, and/or containers of cleaning solvent. Kit 200 also includes a can of pressurized air 238 to assist with keeping various surfaces clean. Another embodiment includes a powered air delivery device.

It should also be appreciated that gloves 232 or finger cots 234 (or a portion of either) may be configured to incorporate some or all of the materials of sampler 100 (as described hereinafter). Accordingly, in a further embodiment, it is envisioned that gloves 232 and/or finger cots 234 (or a portion of either) each constitute a form of sampler (including some or all of sampler 100 features), that can be wiped on the test article 50 to collect one or more analytes directly and then release the collected analyte(s) for transfer to detector 32—it being appreciated that detector 32 of system 20 likewise would be configured to accommodate glove 232 and/or finger cots 234 functioning as samplers. Alternatively or additionally, gloves 232 or cots 234 may include detachable/re-attachable sample-configured pieces (i.e. VELCO, reusable adhesives, or the like). The sampler 100 features incorporable with gloves 232 or cots 234 may include one or more of those previously or subsequently described herein. Like previously described alternatives, kit 200 may be changed to match the particular consumables, tools, and the like associated with the same.

Figure 3:
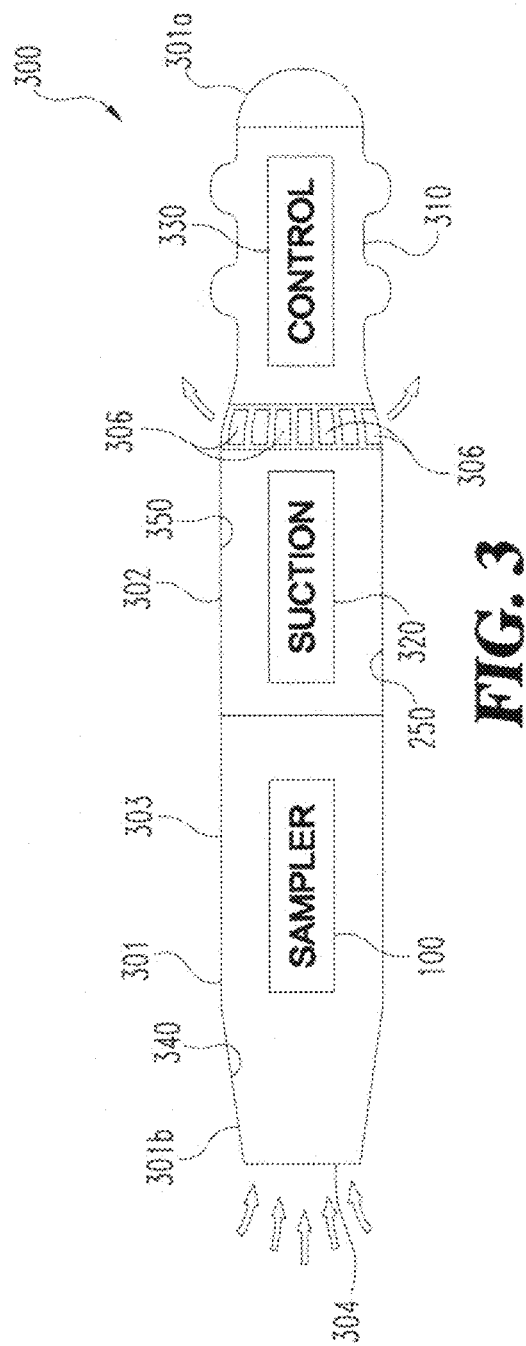
FIG. 3 depicts a partially diagrammatic view showing a handheld wand to receive and operate with a sampler of the type shown in FIG. 1 or FIG. 2.

FIG. 3 depicts mobile sampling wand 300; where like reference numerals refer to like features previously described. Wand 300 may be provided in a kit, as an accessory for detector 32, an option, or separately—to name just a few examples. Wand 300 includes body 301 that is largely hollow. Body 301 is defined by shell 302 that includes surface 303. Body 301 includes proximal end portion 301a opposite distal end portion 301b. Proximal end portion 301b includes operator handle 310, and distal end portion 301b defines vacuum intake opening 304. Within shell 302 is a suction-producing device 320. Device 320 can be powered by an electrochemical cell, a battery of such cells, or a fuel cell—to name a few examples. In one form, wand 300 includes a power cable of suitable length for mobile wand 300 operation—such cable receives electricity from a utility-sourced power outlet to power wand 300. Device 320 is operatively connected to operator control 330. Operator control 330 turns suction device 320 off and on, and optionally adjusts suction speed, reverses air flow direction, and the like.

Sampler 100 is mounted in sample chamber 340 defined by body 301 that is in fluid communication with opening 304, fluid pathways 350, and vents 306. During operation, the suction device 320 is turned on via control 330 to generate suction through opening 304 to move particles, volatiles, and/or other forms of analyte(s) of interest entrained in the resulting airflow for collection by sampler 100 in chamber 340. Airflow continues from opening 304/chamber 340 to discharge through wand vents 306, being directed through pathways 350 in fluid communication therewith. Positioning of sampler 100 and suction airflow through chamber 340 can influence the amount and type of analyte carriers collected with sampler 100. In some forms, sampler 100 is configured as an air filtration device for such purposes.

Analyte(s) collected with sampler 100 may be transferred to detector 32 by removing sampler 100 from wand 300 and inserting sampler 100 in slot 40 for analyte release. Alternatively or additionally, collected analyte(s) may be transferred by reversing the airflow through wand 300 so that pressurized air is directed through and/or over sampler 100 in chamber 240 and out of opening 304—carrying the collected analyte(s). For this embodiment opening 304 is connected/interfaced to detector 32 to receive the sample by adaptive housing, hosing, or a similar mechanism. For this reversed air flow operation, the speed of the air may be increased to assist with release from sampler 100. In one form, wand 300 includes a heating device (not shown) subject to control 330 to assist with the release of analyte(s) during reversed air flow.

Figure 4:
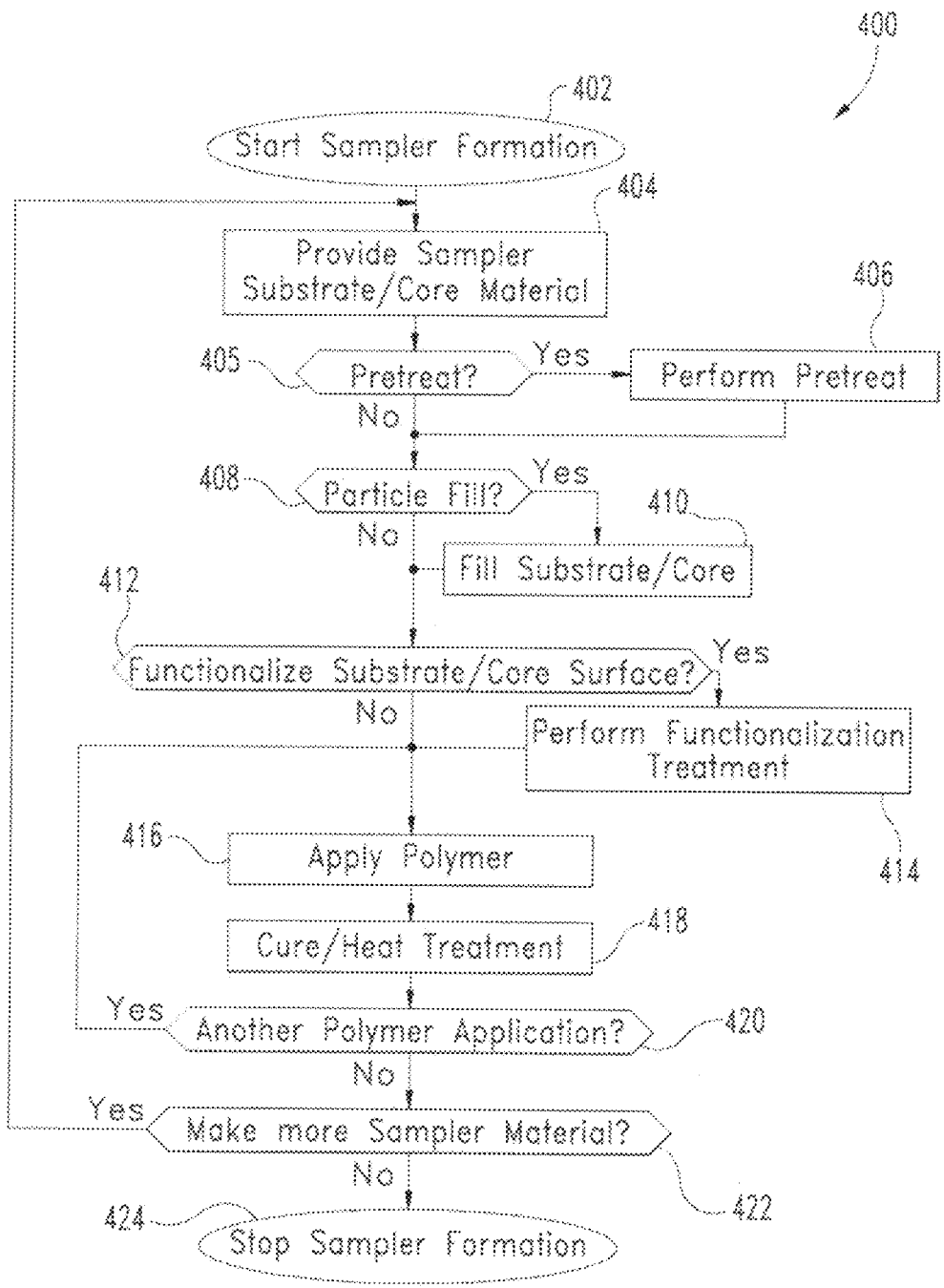
FIG. 4 is a flowchart representing one process for making a sampler according to the present application.

FIG. 4 is a flowchart describing one nonlimiting process 400 for making sampler 100 in various forms; where previously described reference numerals refer to like features. Process 400 begins with sampler 100 formation starting stage 402. From stage 402, process 400 continues with operation 404. In operation 404, a sampler core/substrate material is selected and provided. The sampler substrate may take the form of one or more pieces comprised of a synthetic and/or natural substance. Various factors may be of interest in selecting the sampler core/substrate structure and composition, including: sampler ease of use, relative cost, and material safety; any sampler constraints imposed by detection instrumentation requirements; sampler and core affinity for target analyte collection and retention, and ease of release/transfer of the same to detection instrumentation; existence of any core filling, functionalization, and/or polymer coating, and to the extent in existence, the composition and manner of application of the same; desired sampler and core surface homogeneity, smoothness, shape, or the like; sampler definition of any external openings, recesses, passages, or the like; sampler thermal conductivity, specific heat, thermal mass (or thermal capacitance) or the like; sampler gas permeability; and sampler wear resistance, durability, cleaning, and the like relating to sampler reuse suitability—to name just a few.

Certain embodiments include a fibrous sampler core structure of a nonfabric or fabric variety, while others include a nonfabric without fibers. Such nonfibrous cores may be comprised of one or more nonfibrous solid pieces or the like. In another form, the core is comprised of a fibrous portion and nonfibrous portion. In fibrous embodiments, the fibers may be in the form of filaments, strands, yarn, threading, cord, roves, nanotubes, pultrusions, tows or the like; and may be categorized as being a: nonfabric, nonwoven fabric, and/or woven fabric. Nonfabric fibrous configurations include conglomerations of fibers that may be randomly oriented in terms of direction or in an unbound unidirectional configuration, and any other fiber arrangement that does not qualify as a fabric. Nonwoven fabric types include: spunlaced or any other arrangement of fibers bound together through entanglement without weaving, Chopped Strand Mat (CSM), felts, knitting, braiding, plaiting, velour, leather, and/or by binding fibers together through application of pressure, thermal, chemical, adhesive, resin, organic polymer and/or solvent treatment (either with or without a reinforcement backing), or any combination of these.

In certain embodiments, it has been surprisingly discovered that sampler core/substrate fibers of a fabric form have certain benefits. Woven types of fabric include any type of fibers interlaced in accordance with a weave pattern. Such weave patterns include: plain weaves, satin weaves (including harness satin weaves and crow(s) foot weave), twill weaves, heddle weaves, herringbone weaves, houndstooth weaves, Dutch plain weaves, Dutch twilled weaves, reverse Dutch weaves, Basket weaves, Leno weaves, mock Leno weaves, gauze weaves, cross weaves, tablet weaves, DURAWEAVEs, hybrid weaves, weft-faced weaves, warp-faced weaves (backstrap weaves), oxford weaves, pinpoint weaves, poplin weaves, pile weaves, real weight weaves, combinations of these various weaves, and other known weaves.

Referring additionally to the schematic view of FIG. 5 and the corresponding partial views of 5A-5D, selected fabric weaves are depicted and further described without limitation; where like reference numerals previously described refer to like features. Several of these fabric weave types are commonly used with inorganic fibers, such as various glasses and metals. Any of the depicted weave types may be utilized as a woven form of fabric core for sampler 100; however, these weaves are not intended to exclude different weave types, embodiments with a nonwoven fabric sampler, and/or nonfabric fiber sampler core.

FIG. 5 schematically illustrates the partial views of FIGS. 5A-5D together and designates the contents as weave comparison 500—showing the orientation of the FIG. 5A-5D partial views relative to one another. Collectively, for each depicted weave of FIGS. 5A-5D, fibers 501 are interlaced to provide fabric 502 generically designated by reference numeral 502, which is also generically designated as substrate 503. In FIGS. 5A-5D, only a few of fibers 501 are specifically designated by reference numeral to preserve clarity. The collection, retention, and release of analyte(s) plus other aspects can vary with weave in terms of effective thickness, surface irregularity/roughness, fabric flexibility/stiffness, gas permeation, thermal desorption, solvent extraction, strength, composition, and durability. Further factors bearing on performance include: fiber thickness; filament configuration/size; number of filaments per strand; strand weight/count; number of strands (un)twisted and/or number of strand plies in a yarn, thread, or cord; and yarn/thread/cord texture/size—to name only a few examples.

FIG. 5A depicts four different weave patterns of comparison 500. Plain weave 520 in the upper right corner schematically depicts the warp and weft fibers 501 of a plain weave pattern 526 to generically provide fabric 502. Plain weave 520 is shown from two perspectives: Warp/weft representation 522 and swatch 523. Representation 522 corresponds to a cross-section taken along section line 525. Due to the symmetry of pattern 526, another representation is not shown to preserve clarity. Representation 522 is turned 90 degrees (to line-up with the thickness projecting perpendicular to the view plane) relative to the depiction of swatch 523 parallel to the view plane to enhance understanding of weave pattern 526 by showing an edge-on/thickness view of the arrangement of fibers 501 among other things. Typically, plain weave 520 is relatively tight—being a type of closed weave that readily allows adjacent fibers to come together in contact along at least a substantial portion of the fiber length—and likewise being inhospitable to the formation of any pattern-defined openings as is typical of an open weave.

FIG. 5A further schematically depicts three different types of harness satin weaves 505 of fibers 501 to provide corresponding substrates 503. In the upper left corner, 4 Harness Satin (HS) weave 510 schematically depicts the warp and weft of a 4 HS weave pattern 516 (also known as "crow(s) foot" weave). Weave pattern 516 is also represented schematically in FIG. 6 and designated as a type of fabric 502. 4 HS weave 510 is shown from three perspectives: swatch 513 parallel to the view plane, representation 512, and representation 514. The representations 512 and 514 correspond to the perpendicular weft/warp interlacing pattern 516 of fibers 501, and are turned 90 degrees relative to swatch 513 along the corresponding swatch edges as previously described for weave 520. Representations 512 and 514 enhance understanding of pattern 516 relative to swatch 513 by showing an edge-on/thickness view of pattern 516 and 4 HS weave 510 among other things. 4 HS weave 510 is typically a closed weave.

In the lower left corner of FIG. 5A, 8 HS weave 530 schematically depicts the warp and weft of an 8 HS weave pattern 536 of fibers 501 to provide fabric 502 of substrate 503. 8 HS weave 530 is shown from three perspectives: swatch 533 parallel to the view plane, representation 532, and representation 534. The representations 532 and 534 correspond to sections through weft/warp arrangement of pattern 536, and are turned 90 degrees relative to swatch 533. Each representation 532, 534 is arranged parallel to its section line/swatch edge and perpendicular to one another. Representations 532 and 534 enhance understanding of pattern 536 relative to swatch 533 by showing an edge-on/thickness view of the arrangement of fibers 501 among other things. Typically, 8 HS weave 530 is typically a closed weave.

In the lower right corner, 5 HS weave 540 schematically depicts the warp and weft of a 5 HS weave pattern 546 of fibers 501 to provide fabric 502. 5 HS weave 540 is shown from three perspectives: swatch 543 along the view plane, representation 542, and representation 544, which correspond to sections through the weft/warp arrangement of pattern 546, are turned 90 degrees relative to swatch 54, are aligned parallel to the respective sections and corresponding edges of swatch 543, and are perpendicular to each other. Representations 542 and 544 enhance understanding of pattern 546 relative to swatch 543 by showing an edge-on/thickness view of the warp/weft arrangement of fibers 501, among other things. Typically, 5 HS weave 540 is a closed weave.

FIG. 5B depicts three more weaves of comparison 500. The upper part of FIG. 5B schematically depicts 5 Heddle (HFD) weave 550 comprised of fibers 501 to provide fabric 502 of substrate 503. Weave 550 schematically depicts the warp and weft of HFD weave pattern 556. The HFD weave 550 is shown from three perspectives: swatch 553 in parallel to the view plane, representation 552, and representation 554. The representations 552 and 554 correspond to sections through the weft/warp arrangement of pattern 556, and are turned 90 degrees relative to swatch 553. Representations 552 and 554 are parallel to the respective sections/edges of swatch 553, and perpendicular to each other. Representations 552 and 554 enhance understanding of pattern 556 relative to swatch 553 by showing an edge-on/thickness view of the warp/weft arrangement, among other things.

In the middle part of FIG. 5B, herringbone weave 560 is depicted schematically—being comprised of fibers 501 to form fabric 502 of substrate 503. Weave 560 has the warp/weft arrangement of a herringbone weave pattern 566. Herringbone weave 560 is shown from three perspectives: swatch 563 parallel to the view plane, representation 562, and representation 564. The representations 562 and 564 correspond to sections through the weft/warp arrangement of fibers 501 at right angles, and are turned 90 degrees relative to swatch 563. Representations 562 and 564 are parallel to corresponding edges of swatch 563 and perpendicular to one another. Representations 562 and 564 enhance understanding of pattern 566 relative to swatch 563 by showing an edge-on/thickness view of the warp/weft arrangement among other things. Typically, herringbone weave 560 is of the closed weave type.

The lower part of FIG. 5B schematically depicts 3/3 twilled weave 570 which is one of a group of depicted twills 571 formed from fibers 501 each to provide a corresponding fabric 502 of substrate 503. Weave 570 schematically depicts the warp and weft of a 3/3 twilled weave pattern 576 from three perspectives: swatch 573 parallel to the view plane, representation 572, and representation 574. The representations 572 and 574 correspond to warp/weft sections through pattern 576, and are turned 90 degrees relative to swatch 573 perpendicular to the view plane. Representations 572 and 574 are aligned parallel with the corresponding edges/sections of swatch 573, and perpendicular to one another. Representations 572 and 574 lend understanding of pattern 576 relative to swatch 573 by showing an edge-on/thickness view of the warp/weft arrangement, among other things. The 3/3 twilled weave 570 is of a closed type.

FIG. 5C shows three perspective visualizations of different weaves. The perspective view of these weaves renders separate edge/sectional representations largely redundant. The upper part of FIG. 5C depicts another of the twills 571, namely 2/2 twilled weave 576a, which is formed from fibers 501 to provide fabric 502 of substrate 503. 2/2 twilled weave 576a includes swatch 576b, edge 576c, and edge 576d, that collectively show weave pattern 576e. Edges 576c and 576d provide an edge-on/thickness view of swatch 576b. It should be observed that pattern 576e is similar to pattern 576 (FIG. 5B, lower) except for the number of warp or weft elements floated at one time. The 2/2 twilled weave 576a is of a closed type. In the middle part of FIG. 5C, Dutch plain weave 577a is shown that is formed of fibers 501 to provide fabric 502 of substrate 503. Weave 577a includes swatch 577b, edge 577c, and edge 577d, that collectively show weave pattern 577e. Edges 577c and 577d correspond to the edge-on/thickness view of swatch 577b. Typically, weave 577a is a closed weave type. In the lower part of FIG. 5C, Dutch twilled weave 578a is illustrated, which is formed from fibers 501 to provide fabric 502 of substrate 503. Weave 578a includes swatch 578b, edge 578c, and edge 578d, that collectively show weave pattern 578e. Edges 578c and 578d correspond to edge-on/thickness views of swatch 578b. Typically, weave 578a is a closed type.

FIG. 5D displays three more weave types of comparison 500 each comprised of fibers 501 to provide fabric 502 and corresponding substrate 503. The upper part of FIG. 5D depicts Leno weave 580 (a form of gauze weave) shown from two perspectives: swatch 581 in a plan view and representation 582 turned 90 degrees and aligned parallel with the corresponding edge of swatch 581. Swatch 581 and representation 582 illustrate weft/warp constituents of pattern 580a. Representation 582 shows an edge-on/thickness view of the warp/weft arrangement of pattern 580a, among other things. Leno weave 580 is of the open weave type.

The middle part of FIG. 5D depicts Mock Leno weave 584 shown from three perspectives: swatch 585 with length/width parallel to the view plane, representation 586, and representation 588 perpendicular to representation 586. The representations 586 and 588 correspond to sections through the weft/warp arrangement of weave pattern 584a, are each turned 90 degrees relative to swatch 585, and are each aligned parallel to the respective section/corresponding edge of swatch 585. Sectional representations 586 and 588 enhance understanding of pattern 584a by showing an edge-on/thickness view of the warp/weft arrangement, among other things.

The lower part of FIG. 5D depicts basket (panama) weave 590 shown from three perspectives: swatch 591 parallel to the view plane, representation 592, and representation 594. The representations 592 and 594 correspond to sections/edges parallel to respective weft/warp aspects of pattern 590a, are turned 90 degrees relative to swatch 591, and are perpendicular relative to one another. Representations 592 and 594 enhance understanding of pattern 590a relative to swatch 591 by showing an edge-on/thickness view of the warp/weft arrangement among other things.

Referring back to FIG. 4, the selected structure of the sampler core/substrate in operation 404 is further described. For instance, certain embodiments include a fabric of a woven type. In specific refinements, the weave is one or more of: plain weave, satin weave, twilled weave, heddle weave, and herringbone weave. In further more specific forms, the sampler incorporates a closed weave fabric core. In even more specific forms, a closed weave fabric core includes one or both of a satin weave and a twilled weave. Still another even more particular form includes a closed harness satin weave. Yet a further particular form employs a closed weave of the 4 HS type.

Considering also FIG. 6, a partially diagrammatic cross-sectional view of sampler 100 is illustrated that corresponds to the section line 6-6 shown in FIG. 1. In this sectional view, FIG. 6 illustrates structural fabric core 606 of sampler 100; where like reference numerals refer to like features previously described. Core 606 includes two opposing functionalized sublayers 604 each covered by a corresponding polymer layer 602. Certain additional description of sublayers 604 and polymer layers 602 is deferred until corresponding operations/conditionals 408-420 of FIG. 4 are encountered in sequence hereinafter. Thickness T1 of sampler 100 corresponds to double-headed arrow 106 inclusive of core 606 and layers 602, and thickness T2 of sampler core 606 corresponds to double-headed arrow 108 inclusive of core 606 without layers 602. In some embodiments, the shape and volume of the sampler 100 inclusive of layers 602, and core 606 can impact thermal behavior, sampler flexibility/rigidity, viability of analyte collection (like sufficiency of collection surface area), and the like. Further, sampler dimensions may be constrained by other factors, such as instrumentation, durability and/or handling requirements. To provide a surface area suitable for analyte collection in such embodiments, the dominant surface area (L×W—the "major surface area") is along the side with the Length L and Width W dimensions, where T1 and T2 are much less than L or W (T1<<L, T1<<W, T2<<L, T2<<W). For these embodiments, decreasing thicknesses T1, T2 decreases thermal mass for a given composition and fiber 501 arrangement of core 606, such as its weave 516 for woven fabric 502 form of the core 606 (a specific type of substrate 503), which can enhance thermal desorption performance. However, a decrease in T1 generally presents a trade-off—decreasing the degree of polymer 602 coverage of core 606, and correspondingly reducing sampler 100 stiffness and/or increasing analyte affinity absent functionalization suitable to effective analyte release/transfer; while a decrease in T2 presents a trade-off in terms of mechanical sufficiency potentially impacting wear, durability, and stiffness. As a result, in one form, the core 606 has a thickness less than or equal to 0.5 mm (T2≤0.5 mm); in a more specific form, T2 is less than or equal to 0.3 mm (T2≤0.3 mm); in an even more specific form, T2 is less than or equal to 0.12 mm (T2≤0.12 mm); and in an even more particular form, T2 is less than or equal to 0.1 mm (T2≤0.1 mm). Given overall sampler thickness T1 remains larger than T2 with polymer applied to the core 606 (T1>T2), one respective pairing with the T2 inequalities provides T1 less than or equal to 1 mm (T1≤1 mm) in one form; in a more specific form, T1 is less than or equal to 0.8 mm (T1≤0.8 mm); in an even more specific form, T1 is less than or equal to 0.5 mm (T1≤0.5 mm); and in an even more particular form, T1 is less than or equal to 0.3 mm (T1≤0.3 mm).

Compositionally, natural fibrous materials include: wool, cashmere, alpaca, leather, cotton, silk, flax, hemp, tencel, jute, or the like; synthetic organic material includes: one or more synthetic organic thermoplastic or thermoset polymers, including polymeric nanotubes and nanofibers; inorganic material includes: glass, metal, metalloid, inorganic oxide, metal oxide coated fibers, ceramic, glass-ceramic, or a combination of these. Among the glass compositions, fibers may be composed of pure silica (e.g., ASTRO-QUARTZ, JPS Composites Materials, Anderson, S.C., USA), or predominantly silica with inorganic constituents to provide selected properties. For instance, such silica-based glass fibers may be selected from: HSG as previously defined herein, A-type glasses (e.g. alkali-lime glass with little or no boron oxide); E-type glasses (52%-56% silicon dioxide, 16%-25% Calcium Oxide, 12%-16% Aluminum Oxide, 5%-10% Boron Oxide, 0%-2% Sodium Oxide & Potassium Oxide, 0%-5% Magnesium Oxide, 0.05%-0.4% Iron Oxide, 0%-0.8% Titanium Oxide, and 0%-1.0% Fluorides); E-CR-type glasses (e.g., alumino-lime silicate with less than 1% wt alkali oxides with high acid resistance); C-type glasses (e.g., alkali-lime glass with high boron oxide content); D-glass (borosilicate glass with high dielectric constant); R-glass (alumino silicate glass with no MgO or CaO); S-type glasses (64%-66% Silicon Dioxide, 0%-0.3% Calcium Oxide, 24%-26% Aluminum Oxide, 0% Boron Oxide, 0%-0.3% Sodium Oxide & Potassium Oxide, 9%-11% Magnesium Oxide, 0%-0.3% Iron Oxide, 0% Titanium Oxide, and 0% Fluorides—e.g., alumino silicate glass without CaO but with high MgO), and combinations of these various glasses—it being understood that the parenthetical descriptions of different glass types are exemplary only and any other formulas considered by those of ordinary skill in the art to be one of these glass types at the time of filing of the present application are intended to be included.

Likely candidates for metal fibers include, but are not limited to, e.g., iron (Fe), aluminum (Al), copper (Cu), nickel (Ni), silver (Ag), and including metal alloys thereof. In a further refinement, in some embodiments metal fibers may be treated with acid or base to clean and activate the surface of the fibers prior to use or subsequent processing (such as operation 414). In certain embodiments, metal fibers may include a native oxide coating on the surface of the metal fibers. Fibers may be composed of or include, metal oxides, oxide-coated metals, or metals that include a metal oxide coating of the same or different metal provided that refractory properties of the metal oxide coating are compatible with the underlying metal. Inorganic oxides encompass both metal oxides and non-metal oxides for fibers, including, but not limited to: $Ag_2O$, $Al_2O_3$, $As_2O_3$, $As_4O_6$, $BaO$, $B_2O_3$, $BeO$, $Bi_2O_3$, $CO$, $CaO$, $CdO$, $CeO_2$, $CoO$, $CrO_3$, $Cr_2O_3$, $CuO$, $Cu_2O$, $Dy_2O_3$, $Er_2O_3$, $Eu_2O_3$, $FeO$, $Fe_2O_3$, $Ga_2O_3$, $GdO_3$, $GeO_2$, $Ho_2O_3$, $HfO_2$, $In_2O_3$, $IrO_2$, $K_2O$, $KNaO$, $La_2O_3$, $Li_2O$, $Lu_2O_3$, $MgO$, $MnO$, $MnO_2$, $Mn_2O_3$, $MoO_3$, $N_2O_5$, $Na_2O$, $Nb_2O_3$, $Nb_2O_5$, $Nd_2O_3$, $NiO$, $Ni_2O_3$, $PO_4$, $PbO$, $PdO$, $PmO_3$, $PrO_2$, $Pr_2O_3$, $PtO_2$, $Rb_2O$, $Re_2O_7$, $RhO_3$, $SO_3$, $SO_4$, $Sb_2O_3$, $Sb_2O_5$, $Sc_2O_3$, $SeO_2$, $SiO_2$, $Sm_2O_3$, $SnO_2$, $Ta_2O_5$, $Tb_2O_3$, $ThO_2$, $TiO_2$, $Tl_2O$, $Tm_2O_3$, $V_2O_5$, $WO_3$, $Y_2O_3$, $Yb_2O_3$, $ZnO$, $ZrO$, $ZrO_2$, and combinations of these various oxides. Other minor constituents commonly found in the subject material may also be found therein which are unlikely to influence the properties of the overall material including, e.g., alkali metal oxides, alkaline earth oxides, and impurities.

In certain embodiments, the sampler core, whether fibrous or otherwise, includes one or more of: glass, metal, metalloid, inorganic oxide, polymeric thermoplastic, polymeric thermoset, ceramic, glass-ceramic, and/or metal or glass coated with metal oxide as described further herein. In one specific embodiment of sampler 100, the core/substrate includes one or more of: glass, metal, metalloid, inorganic oxide, ceramic, and glass-ceramic. In a more specific embodiment of sampler 100, the core/substrate includes one or more of: HSG, metal, metalloid, metal oxide, ceramic, and glass-ceramic. In further more specific embodiment, the core is comprised of at least one of: HSG, metal, metalloid, and metal oxide. In an even more specific embodiment, the core is comprised of one or more of: HSG, metal, carbon, and metal oxide. In still a more specific embodiment, the core is comprised of HSG. In yet a more highly specific embodiment, the core is comprised of S-glass. In still other specific embodiments, the core is comprised of one or more glasses or metals coated with one or more compatible metal oxides. While S-glass is favored for some embodiments, it is surmised other materials, such as those of the progressively more specific groups/types listed above will perform similarly or even better in certain other embodiments.

Other considerations in the selection/performance of core composition are intrinsic thermal properties, which relate to the ability to release/transfer analyte(s) through thermal desorption when relevant, as when used with instrumentation 30, among other things. These properties include thermal conductivity and specific heat capacity. In certain embodiments, a fiber core has a thermal conductivity greater than about 0.2 W/m-K. In further embodiments, the thermal conductivity is greater than about 0.4 W/m-K. In still other embodiments, the thermal conductivity is greater than about 0.6 W/m-K. Alternatively or additionally, other embodiments have a specific heat of the fiber below about 1.3 J/g ° C. In further embodiments, the core fiber specific heat is in a range from about 1 J/g ° C. through about 1.3 J/g ° C.; yet in other embodiments, this specific heat is in a range from about 0.5 J/g ° C. through about 1.2 J/g ° C.; and still other embodiments have a fiber specific heat in a range from about 0.1 J/g ° C. through about 0.5 J/g ° C.

Per FIG. 6, sampler 100 includes an analyte sampling surface 612 on each opposing side of sampler 100, as defined by respective opposing polymer layers 602. Layer 602 is disposed on fiber core 606 to collect, retain, transfer, and release trace particles and/or other forms of targeted contraband or undesirable substance(s) for detection. In some embodiments, such detection may be performed with instrumentation 30 through thermal desorption or in a different manner. Polymer layer 602 may completely coat fiber core 606, or only partially cover/coat core 606. In one form, the major surface area (L×W) on opposing sides of sampler 100 are completely or partially configured with sampling surface 612. In other embodiments, just a single side is completely or partially configured with a sampling surface 612. In a further instance a glove 232 or finger cot 234 implementation of the sampler may only have a sampling surface on its outer side, and/or may be confined to a selected region or regions thereof.

For the depicted embodiment, core 606 shown in FIG. 6 is comprised of a fabric 502 with the 4 HS weave 516—both fabric 502 and weave 516 are further described in connection with FIG. 5A and accompanying text hereinbefore. Further, for the purposes of providing a fuller example in connection with the conditionals/operations of process 400, fibers 501/fabric 502 is made of S-glass. However, in other embodiments, the mechanical and/or compositional aspects of the core/substrate may vary—it being specific in this case just for the sake of example. The FIG. 6 representation is shown with level, horizontal surfaces in block form to preserve clarity of various features that may be readily obscured or confused otherwise. However, core 606 comprised of fabric 502/fibers 501 with 4 HS weave 516 would likely exhibit an undulating core surface 605 in a corresponding weave surface pattern—with greater complexity and unevenness (not shown). Correspondingly, polymer layer 602 would tend to be uneven, too, depending somewhat on relative thickness and degree of coverage (not shown).

In addition, some fiber surfaces (such as glasses) can be tailored with a specified surface chemistry that may be useful to facilitate better polymer layer 602 coverage and/or provide a surface more compatible with selected analyte(s), and/or collection, retention, release, and transfer to the extent fiber core 606 is uncovered by layer 602. The enhanced surface chemistry may provide better surface homogeneity and more suitable analyte affinity—directed to better analyte recovery when compared with less homogeneous surface chemistry of other arrangements. Correspondingly, enhanced surface chemistry can enhance polymer coverage and/or the collection, release, transfer, and detection (i.e., signal intensity) of released analyte(s) with it.

By way of nonlimiting example, an S-glass/4 HS weave 516 form of sampler 100 shall serve as the sampler core/substrate selected during operation 404 of process 400 (FIG. 4) for nonlimiting illustrative purposes. From operation 404, process 400 continues with conditional 405. Conditional 405 tests whether the selected core/substrate material would benefit from a pre-treatment. If the test of conditional 405 is affirmative (Yes), process 400 proceeds to operation 406. If this test is negative (No), process 400 proceeds to conditional 408, bypassing operation 406. For this example, an effective pretreatment procedure is available so process 400 continues with operation 406. Typically pretreatment in operation 406 removes contaminants, alters the material in some other fashion, or otherwise prepares the material for subsequent operations. Accordingly, pretreatment may involve application of a chemical, thermal, and/or mechanical procedure. For the stated example, high levels of nitrates are sometimes present in S-glass and potentially some other glass types, which is an unwanted contaminant. To remove this contaminant, a heat treatment is applied. It has been found exposure of the material to 500° C. for 4 hours or more is sufficient to reduce nitrates to an acceptable level.

Other procedures additionally or alternatively may be applicable to this example material; and to different materials as might be performed under operation 406 in other examples/embodiments. Under certain circumstances commercially available glass or silica fiber materials are coated with a variety of chemicals such as binders, oils, resins, and other compounds that facilitate uses in a variety of industrial applications. Removal of these compounds is performed to enhance installation of specific core/substrate surface chemistries at desired density in operation 414 to be further described hereinafter. For example, untreated glass and/or silica fibers can include many unavailable reactive surface sites because these surface sites are physically obstructed by a surface coating or undesirable contaminants, or are chemically unavailable because of a previous reaction between adjacent silanols (e.g., metal hydroxyl groups) that form, e.g., bridging oxo groups. Further pretreatment information is deferred until operation 414 is reached by process 400.

From operation 406, process 400 advances to conditional 408, which tests whether a fill procedure should be performed. If the test is negative (No), process 400 continues with conditional 412, bypassing operation 410. If the test is affirmative (Yes), process 400 advances to operation 410. In operation 410, a particulate material is applied to core 606/substrate 503 to enhance thermal and/or other desired properties as suited to the application. For the S-glass/4 HS weave example, operation 410 is performed to at least partially fill the core 606 with alumina ($Al_2O_3$) nanoparticles to increase thermal performance because $Al_2O_3$ has a thermal conductivity several times greater than S-glass. These nanoparticles are represented by small circles in sublayers 604 of core 606 with only a few being designated by reference numeral 620 to preserve clarity. In FIG. 6, nanoparticles 620 are shown closer to surface 605 in sublayers 604; however, they may become more deeply embedded and uniformly dispersed than shown. In one embodiment, the mean diameter of nanoparticles 620 is about 50 nanometers (nm); but, in other embodiments a differently sized nanoparticle, a larger particle, other than a nanoparticle, or nonparticle may be used. Additionally or alternatively, one or more carbon-based allotropes can be used as a nano-sized or other filling material that are selected for a desired level of thermal conductivity/performance; such allotropes including: carbon nanotubes, graphene, amorphous carbon, carbyne (linear acetylenic carbon), carbon nanofoam, fullerenes, glassy carbon, graphite, or the like. In FIG. 6, nanoparticles 620 also represent nano-sized carbon allotrope forms to the extent otherwise designated. In yet another embodiment, the fill material is one or more of particles of: metal oxide, metalloid, metal, ceramic, and glass-ceramic. In a further embodiment, the fill material is comprised of particles of: metal oxide, carbon, ceramic, and glass-ceramic. In a more specific embodiment, the fill material is comprised of nanoparticles of metal, metal oxide and/or carbon. In yet an even more specific embodiment, carbon nanoparticles of a nanotube and/or graphene allotrope provide the fill material. In other embodiments a different and/or multiple types of fill material may be used to coat, partially fill or generally completely fill the core/substrate. Typically, fill material is selected to improve an aspect of the core 606 for which improvement is desired, such as a thermal characteristic. In another form, particles of at least one of metal and metal oxide is used at least some of which may be nanoparticles. In another form, the particles are alumina and are of nanoparticle size. In other embodiments, operation 410 is not performed at all—such that no fill material is used, being bypassed by conditional 408.

Next, process 400 encounters conditional 412, which tests whether to functionalize surface 605 of core 606 to provide sub-layers 604. If the test is negative (No), procedure 400 continues with operation 416, bypassing operation 414. If the test is affirmative (Yes), process 400 moves to operation 414. In operation 414, surface sub-layers 604 of core 606 are formed to improve the desired collection and release of target analyte(s) with surface 605/sub-layer 604, improve subsequent application of polymer layer 602, and/or provide other desired features through installation of desired surface chemistry. In one form, functionalization may be performed according to the '910 patent, which provides exhaustive description thereof.

It has been discovered that a glass form of core 606 generally tends to bind with certain analytes to such an extent that release/transfer by thermal desorption can be hampered, resulting in a reduced detection signal. Moreover, glass surfaces tend to be polar which can affect the uniformity of polymer coverage in subsequent operations (such as polymer application in operation 416). Such nonuniformity also indirectly can impact analyte collection and/or release because polymer 602 covers surface 605 to a lesser/incomplete extent. Generally, polymer coating 602 may not be uniform over surface 605 of core 606 due to 4 HS weave shape or the like, so that functionalization facilitates a more robust, uniform analyte detection response. Fill particles (such as alumina nanoparticles 620), can also tightly bind to analyte(s) and/or may also benefit from functionalization.

In FIG. 6, generic "R" functional groups are labeled in sublayers 604, where each "R" is appended to core 606 by a line representative of bonding to core 606. The resulting interfacial sub-layer 604 is representative of organo-silanes provided according to the '910 patent or other chemistry resulting from a different procedure. The relative size of sub-layers 604 is not to scale in FIG. 6, and may in fact only have a thickness of no more than about a molecule or so in some applications. The '910 patent provides further details regarding various functionalization operations/options, and is generally compatible/adaptable with those of the present application. To accommodate functionalization, process 400 may include pre- and post-treatments per the '910 patent to perform/enhance the formation of sublayers 604 and further improve compatibility with subsequent stages. Some pretreatments may already have been described for operation 406 but are repeated here in connection with functionalization, namely: (a) to remove commercial coatings or surface contaminants (See '910 patent FIG. 2a and accompanying text), an exemplary pretreatment process to prepare for functionalization of the core surface 605 is further discussed, which may be used as an addition or alternative to that previously described for operation 406; where such functionalization preparation pretreatment can activate and increase density of reactive groups such as silanols on the surfaces of fibers 501 and/or correct unfavorable surface chemistry—by way of example, fibers 501 treated with, e.g., bases or acids can increase the density of silanols on the surfaces in the absence of added water—while in others, hydrotreating the surface with an aqueous medium can increase the density of silanols or reactive (—OH containing) groups on surface 605; (b) silanizing fibers 501 by chemically attaching silanes (e.g., phenyl silanes) on surfaces 605 of fibers 501, (c) conditioning (i.e., cleaning) surfaces 605 of the surface-functionalized or modified fiber 501 fabric 502 material, and/or (d) post-treating the surface-modified fabric 502 to remove unreacted agents (or oligomerized but unattached silanes) from fabric 502.

FIG. 2b of the '910 patent shows an exemplary condensation reaction for direct attachment of silane ligands or terminally functionalized silane ligands to activated anchor sites (e.g., silanols) on the surfaces of fabric fibers that may be performed in operation 414. Surfaces 605 including glass, metal oxide, and/or oxide coated glass or metal fibers are amenable to surface functionalization using a wide range of functional groups through Si—O—Si bonds [or metal (M)-O—Si bonds in the case of metal oxide and oxide-coated metal fibers] that form in concert with Anchor groups (Z) attached to a silicon (Si) atom at the terminal attaching end of a Linking group (Y). Another terminal end of the Linking group (Y) may include other terminal groups (X), e.g., as shown in chemical expression [1] of the '910 patent.

In some embodiments, the silanization procedure of operation 414 may involve chemically attaching silanes to reactive Si—OH groups on the surface 605 of fibers 501 in sublayers 604. For example, Si—OH reactive sites on the surface 605 of the fibers 501 may attach to selected silane ligands via an Anchor group (Z) positioned at the attaching end of the silane ligand. The reaction may form a Si—O—Si bond, e.g., via a condensation reaction. In some embodiments, silanes can attach directly to reactive Si—OH (Anchor) groups (Z) in the absence of a Linking group (Y). FIG. 3 and accompanying text of the '910 patent provides further information.

Silane ligands suitable for selective collection of target analyte(s) include, but are not limited to, e.g., phenyl silanes; organosilanes; alkoxysilanes; alkyl silanes; siloxanes; phenyl-trimethoxysilanes; silanols; combinations of these various silanes; and/or hydrocarbyl derivatives thereof. As described further in the '910 patent, functionalization/passivation of any residual reaction sites can yield further improvements in surface chemistry results and/or functionalization processing may be performed multiple times per the '910 patent. Phenyl silanes represent an exemplary surface chemistry for modification and functionalization of glass, silica, metal oxide, and/or oxide-coated glass or metal fibers 501 within the sampling fabric 502 of core 606 for collection of a wide variety of organics. Phenyl silanes provide a thermally robust and thermally stable surface chemistry at temperatures in excess of 400° C. In addition, phenyl silanes can provide a lipophilic surface with a general affinity for various organic materials, and additionally, greater chemical selectivity for TNT and other nitroaromatics, as detailed further in the '910 patent. With terminal groups attached to the silanes, various other terminal groups or ligands can be chemically attached to the terminal end of the silane ligands to provide enhanced affinity/selectivity. Once silanization is complete in operation 414, sampling surface 605 may be further treated to ensure that silanes are completely bound to the surface and to remove unwanted reactants and side products. This stabilization process prepares the functionalized surface for collection of target analytes. In other embodiments, a surface chemistry functionalization based on something other than silanization may be used. For such embodiments, operation 414 includes appropriate stabilization treatment, as applicable.

The schematic view of FIG. 7, depicts a portion of alternative sampler 800 in perspective. Various features of sampler 800 are not shown relative to scale to highlight certain aspects and does not include complete crosshatching to avoid obscuring certain features. Phenyl terminal functional group P of sampler 800 is a specific implementation of operation 414, with only some being specifically designated by the reference characters to preserve clarity. In other words, phenyl groups P are a specific form of the generic silanization terminal groups R shown in FIG. 6. Double polymer layering 602, 802 is applied over phenyl groups P. Outer/upper surface 802 defines sampling surface 802. Sampler 800 does not specify any particular weave unlike weave 516 of sampler 100.

Returning for FIGS. 4 and 6, from operation 414 process 400 advances to operation 416. In operation 416 polymer layer 602 is formed on core 606 that defines sampling surface 612. Polymer layer 602 may be applied to core 606 by various means, including without limitation: an aqueous or other liquid-based dispersion of polymer particles in the form of a painted or brushed-on coating, a spray, dipping in the liquid, or the like; a powder of polymer particles deposited on the core; molding a polymer film, sheet, or lamination onto the core, or such other application as known to those of ordinary skill in the art. The amount of polymer applied is typically in a range of about 2% wt through about 50% wt depending on various target properties of sampler 100 such as stiffness, analyte collection/release, the degree of core coverage by the polymer, sampler thickness/thermal mass, and the like—as discussed further hereinafter. Indeed, in some embodiments, only partial core coverage by the polymer may be desired.

As to composition, one preferred embodiment of the polymer layer 602, 802 is comprised of one or more of: polymeric organofluorine, polyamide, polyimide, PolyBenzlmidazole (PBI), PolyDiMethylSiloxane (PDMS), sulfonated tetrafluoroethylene (PFSA), and Poly(2,6-diPhenyl-p-Phenylene Oxide) (PPPO). PPPO is also known by the trademark TENAX TA, and a PPPO/graphitized carbon combination (also known by the trademark TENAX GR) is included in the group because PPPO is a constituent of both the above group listing and the graphitized carbon combination. Alternatively or additionally, in other forms the composition of the polymer applied to any of the previously described cores may be a member of any of the following successively more specific listings (a)-(e): (a) perfluorocarbon, perfluoroether, Ethylene-TetraFluoroEthylene copolymer (ETFE), Ethylene ChloroTriFluoroEthylene copolymer (ECTFE), poly(tetrafluoroethylene-hexafluoropropylene-vinylidene fluoride) (THV) copolymer, PolyVinylidene diFluoride (PVdF), Fluorinated Ethylene-propylene (FEP), PolyChloroTriFluoroEthylene (PCTFE), PolyVinyl Fluoride (PVF), PolyTRiFluoroEthylene (PTRFE), poly(vinylidene-tetrafluoroethylene) copolymer, poly(vinylidene-trifluroethylene) copolymer, PPBI, PDMS, and PPPO; (b) perfluorocarbon, perfluoroether, ETFE, FEP, THV copolymer, PVdF, and PPPO; (c) perfluorocarbon, PerFluoroAlkoxy (PFA), ETFE, PVdF, and FEP (where "pefluoroether" is inclusive of PFA); (d) PFA, ETFE, FEP, and PTFE; and (e) PTFE. While PTFE is favored for certain embodiments, it is surmised that analog polymers and others like PTFE will perform similarly. Also, to the extent thermal desorption is used with the sampler 100, 800 it is a preference that polymer 602, 802 have a thermal decomposition temperature above the temperature applied to perform thermal desorption with detection instrumentation 30.

Accordingly, one specific form of the sampler 100 applies PTFE to the exemplary S-glass/4 HS weave core. In one approach, PTFE is applied to S-glass fibers by depositing a coating on the core of an aqueous dispersion of PTFE polymer particles. This deposition may include brushing the dispersion on the core, dipping the core in the dispersion, or the like. In further embodiments, a different polymer may be applied and/or a different manner of application used. Additionally or alternatively, in other embodiments the core differs in composition and/or arrangement of core fibers. Such arrangement can differ among various embodiments as to type: non-fibrous nonfabric, nonwoven fabric, and/or woven fabric; and if the core includes a woven fabric, the weave type of such fabric can include or vary from the 4 HS type, and may have a closed or open weave for different embodiments.

Per FIG. 4, process 400 moves from operation 416 to operation 418. In operation 418, the polymer application is cured/heat-treated as needed for the core/polymer materials utilized to prepare sampler 100, 800 for use with detection instrumentation. In one embodiment, heat treatment is performed for the aqueous dispersion form of PTFE applied to an S-glass/4 HS woven fabric sampler core. It has been discovered that heat treatment in the range between the polymer melting point and the thermal decomposition temperature tends to yield a better detection response compared to heat treatment temperatures outside of this range, and further has been surprisingly found to be a factor in controlling sampler stiffness. In one form, operation 418 heats a glass core with a PTFE polymer core application to a temperature of about 400° C. for 30 minutes; where the PTFE melting point is about 327° C. and the thermal decomposition temperature is about 448° C. In an alternative form, the applied temperature is about 425° C. for 30 minutes. In a further embodiment, the heat treatment temperature is between about 390° C. and about 435° C. and applied for at least 30 minutes. In other embodiments, a different cure/heat treatment may be applied after polymer application that may further include control of applied pressure/vacuum. In still other embodiments, a different core and/or polymer application is used with an appropriate heat treatment, if any.

In addition to heat treatment of operation 418, another factor impacting sampler stiffness and signal response is the relative amount of polymer applied to the core 606. After curing in operation 418, the calcined amount of the polymer applied is broadly in the range from about 2% wt through about 50% wt. In one form, the calcined polymer amount after curing is less than or equal to about 40% wt. For a further form, the calcined polymer amount after curing is less than or equal to about 20% wt. In still another form, the calcined polymer amount after curing is in a range from about 20% wt through about 40% wt. Still a different form has a calcined polymer amount in a range of about 24% wt through about 36% wt.

With the addition of polymer layer 602 for sampler 100 (and potentially layer 802 of sampler 800), thickness T1 of sampler 100 (or sampler 800) is established, which can have a bearing on thermal behavior and accordingly the release of analyte(s) through thermal desorption with instrumentation 30—much like thickness T2 of core 606. One preferred embodiment based on a nominal core thickness T2 of about 0.3 mm has an overall sampler thickness T1 of less than or equal to about 0.8 mm depending on polymer amount applied. In another embodiment, the T2 thickness is less than or equal to about 0.5 mm. In still another embodiment, sampler thickness T2 is less than or equal to about 0.12 mm.

From operation 418, process 400 continues with conditional 420. Conditional 420 tests whether to apply a further coat of polymer. Such polymer may be the same or different from that applied previously. If the test is negative (No), process 400 continues with conditional 422. If the test is affirmative (Yes), process 400 loops back to operation 416 to apply further polymer of the same type or a different type. It should be understood, that with multiple applications of polymer(s), operation 418 may be performed for each layer separately or may be deferred until some or all of the polymer/polymers is/are applied depending on the nature of the polymer(s), the application regime in operation 416, and curing technique(s) in operation 418.

After looping back to operation 416 for further polymer application, in one multilayer polymer embodiment, at least two or more thin PTFE applications occur. Such duplicative applications may be individually thinner than would the application of just one thicker polymer layer. In another embodiment, a two-layer polymer has an inner layer of PTFE and an outer layer of PPPO. In still another two-layer polymer embodiment, an outer layer of TENAX GR (PPPO/ graphitized carbon combination) is applied on an inner layer of PTFE. In FIG. 7, as previously indicated sampler 800 includes two distinct polymer layers 602 and 802 that may be of the same or different compositions depending on amount and relative coverage. The outer polymer layer 802 defines sampling surface 812 that operates in a manner analogous to sampling surface 612, which is shown covered by polymer layer 802 in FIG. 7. Polymer layer 602 serves as an inner, base layer relative to outer layer 802. In accordance with process 400, additional polymer applications may take place as practically limited by performance requirements or the like; while in other embodiments, no more than the first polymer layer 602 application takes place.

Flexure of the sampler or conversely "stiffness" may be empirically evaluated by determining flexural modulus of the sampler as defined herein. The flexural modulus is similar in some respects to the more familiar Young's modulus, both are often similar in value for a given material with common units of measure (units of pressure) but each is determined differently. Flexural modulus is commonly used with synthetic organic polymers and composites thereof. In certain embodiments, a sampler has a flexural modulus greater than or equal to about 0.75 GigaPascal (GPa). In still further embodiments, the flexural modulus of the sampler is greater than or equal to about 1.0 GPa. In different embodiments, the flexural modulus of the sampler is less than or equal to about 2.0 GPa. In still other embodiments, the flexural modulus of the sampler is less than or equal to about 3.0 GPa. In still further embodiments, the flexural modulus is less than or equal to about 4.0 GPa. For some preferred embodiments, the sampler flexural modulus is in a range of about 0.75 GPa through about 10 GPa. In some more preferred embodiments, the sampler flexural modulus is in a range from about 1 GPa through about 8 GPa. In some even more preferred embodiments, the flexural modulus is in a range from about 2 GPa through about 6 GPa.

When conditional 420 is negative, whether following just one polymer application or multiple polymer applications, conditional 422 is encountered. Conditional 422 tests whether more sampler material is to be made. If the answer to this test is affirmative, process 400 loops back to operation 404 to perform the previously described conditionals and operations to the extent applicable—eventually returning to conditional 422 to test for continuation again. If the answer to the test of conditional 422 is negative (No), then process 400 halts. The sampler material resulting from process 400 is shaped as desired using stamping, etching, trimming, cutting, or another procedure to provide sampler 100 with the desired shape. In some embodiments, sampler 100 has a sampling surface with a shape/perimeter selected from: a circle, an oval, an ellipsis, a rectangle, a square, a triangle, a regular polygon, an irregular polygon, a polyline, or combinations thereof. In certain embodiments, shaping may take place before provision in operation 404 or elsewhere during process 400 before conditional 422 is encountered. To the extent desired, sampler 100 may be cleaned and dressed after process 400 and optionally packaged prior to use. In still other embodiments, the sampling surface takes the form of a finger cot 234, glove 232, or a portion thereof; or the sampler may be selectively attachable to the finger cot 234 or glove 232 (See kit 200 of FIG. 2).

FIG. 8 is a flowchart describing process 700 directed to the use of sampler 100 or 800; where previously described reference numerals refer to like features. Process 700 begins in stage 702 to start sampler 100, 800 application. From stage 702, process 700 advances to conditional 704 to test if the application is for trace analyte detection or another application. If the test is negative (No), process 700 bypasses several stages to next encounter conditional 716 as described further hereinafter. If the test is affirmative (Yes) for conditional 704, operation 706 is encountered in which the test article 50 is identified or otherwise predefined or known in advance, and sampler 100, 800 is applied to collect analyte(s) from surface 54 of test article 50 in accordance with any of the approaches described in connection with FIGS. 1-3—that is using sampler 100, 800 to collect one or more target analytes by swiping, wiping, suction, with a wand, or the like, and/or through an analyte-entrained airflow—as could be employed with pass-through portals (See the '513 patent) to name a few examples. Test article 50 may be in any of a number of different forms, such as cargo/freight, associated packaging, shipping canisters or containers, tanks, crates, boxes, luggage, barrels, packing cases, child car seats, strollers, wheelchairs, purses, briefcases, travel cases, books and other documents, backpacks, electronic equipment (like laptops, tablets, headphones/ear buds, Personal Digital Assistants (PDA), and/or cellular phones), clothing/apparel/accoutrements, skin surfaces, vehicles, countertops, floors, walls, ceilings, and/or other surfaces as may occur to an operator.

Once analyte collection is completed with sampler 100, 800; transfer of the collected analyte(s) to appropriate trace detection instrumentation 30 is next performed in operation 708. In operation 708, such transfer typically involves a controlled release of the analyte(s) from sampler 100, 800. Such release may be performed chemically using appropriate agents/solutions and or agitation (such as stirring, churning, rocking, shaking, swaying, teetering, quavering, rolling, wobbling, oscillating, vibration, mixing, scrubbing, scouring, or other physical disturbance) with subsequent transfer to instrumentation 30, or through thermal desorption to release analyte(s) for processing by detector 32 while sampler 100, 800 is at least partially inserted in slot 40—to name a few examples. Further, application of more than one liquid may be used to clean/extract analyte(s) from sampler 100, 800; utilization of an acid (such nitric acid), a base (such as sodium hydroxide), water, or one or more organic solvents; and/or a mixture of a oxidizer (like a peroxide such as hydrogen peroxide) with a source of one or both of onium and carbonate. In some embodiments, the surface of the swipe sampler fabric retains the analyte(s) until thermally released into instrumentation 30 at a release temperature greater than the collection temperature that may involve certain detection instrumentation gas flow(s) of controlled flow rate(s), composition(s), and temperature(s). In certain embodiments, the release includes thermally desorbing the analyte(s) at a temperature between about 100° C. and about 500° C. In preferred embodiments, the analyte release temperature is less than any thermal decomposition temperature associated with sampler 100, 800. For instance a thermal desorption temperature equal to or less than 450° C. has been found suitable for PTFE-coated S-glass samplers to provide just one nonlimiting example. Once transferred, in operation 708 analyte(s) are evaluated by instrumentation 30 to determine if one or more target analytes are present, the results may be provided via display 34 and/or printer 38 for the configuration previously described in connection with FIG. 1. The '910 patent further describes analyte sampler removal techniques in connection with TABLE 6.

From operation 708, process 700 continues with operation 710. In operation 710, sampler 100, 800 is prepared for re-use. The analyte release/transfer to instrumentation 30 may self-clean/prepare sampler 100, 800 for reuse. In the case of thermal desorption, the desorption temperature may be sufficient to self-clean/prepare sampler 100, 800 for reuse, or may be capable to subjecting sampler 100, 800 to an elevated temperature/time period sufficient to prepare for reuse. In other embodiments, the release of analyte(s) includes mechanically and/or chemically cleaning the surface of the sampler 100, 800 to prepare for reuse or collection of other analyte(s) from a selected surface. In still other embodiments, a completely separate treatment is performed to place sampler 100, 800 in condition for reuse under operation 710. From operation 710, process 700 advances to conditional 714, which tests whether to perform another trace detection, and may include reuse of sampler 100 after preparation in operation 710. If the test is affirmative (Yes), process 700 loops back to repeat operations 706, 708, 710, and conditional 714. If the test is negative (No), process 700 falls through to conditional 716, which is also reached directly from a negative result of the test of conditional 704.

Conditional 716 tests whether sampler 100 is of a type suitable for detection of an actinide series member, such as uranium, and whether to test for the same. It should be appreciated that samplers suitable for use in earlier operations to detect non-nuclear analyte(s) may or may not be preferred for nuclear material detection. If the test result is negative (No), process 700 moves forward to conditional 720, and if the test result is affirmative (Yes), process 700 moves to operation 718. A principal technique employed by the International Atomic Energy Authority (IAEA) for the enforcement of the Non-Proliferation of Nuclear Weapons Treaty (NPT) involves the use of environmental sampling to detect nuclear signatures that might reveal improper activities at otherwise declared facilities. Nuclear processing activities can leave trace signatures on surroundings that may be sampled by collecting dust. Uranium is often found in the form of $U_3O_8$ or $UO_2$, which are crystalline compounds with relatively low solubility in water. Because $U_3O_8$ is one of the most stable forms of uranium, it is commonly found in nature. $UO_2$, on the other hand, is typically the uranium chemical form of choice in the final stages of nuclear fuel fabrication. Uranium Ore Concentrate (UOC) or "yellow cake," as it is commonly known, is characteristically a commercial product of a uranium mill, usually containing a high concentration (at least 90%) of uranium oxide $U_3O_8$. Uranyl fluoride ($UO_2F_2$) is a decomposition product that forms from the reaction of moisture and uranium hexafluoride ($UF_6$). Another compound sometimes found in such samples is uranyl nitrate ($UO_2(NO_3)_2$), which is prepared from uranium salts treated with nitric acid. Uranyl nitrate is a compound sometimes encountered in the reprocessing of spent fuel. In addition, still another uranium compound that might be encountered is uranyl orthophosphate ($UO_2(HPO_4)*4H_2O$) that is also known by the abbreviation "HUP." Standard sampling procedures normally smear highly clean pieces of cotton fabric across surfaces of interest to collect a dust sample that is later subjected to in-depth analysis. Among the drawbacks of the existing scheme is the need for complete chemical digestion of the cotton/dust sample matrix, which is often time consuming/labor intensive, limiting laboratory throughput, elevating costs, and adding to background contamination from the sampling fabric, which ultimately limit test sensitivity.

In contrast, it has been surprisingly discovered that certain polymer-coated cores or substrates provide high collection efficiency of industrial dust, including uranium compound particles of particular interest for nuclear inspection protocols. In addition to nuclear safeguard applications, this technique has application to the safety and security monitoring of nuclear power reactors and related facilities. Accordingly, in operation 718, testing with sampler 100 is performed for the trace detection of uranium. During operation 718, the collected surface-bound particles can be readily removed (extracted) by liquid from the polymer-coating, which may be performed more quickly and with less labor than pre-existing schemes relying on cotton fabric collectors. Extraction may or may not involve digestion of some or all of the PTFE-coated sampler because release of certain uranium compound(s) from PTFE can be accomplished without complete digestion depending on the applicable conditions—such as the extraction liquid composition, length of exposure to the extraction liquid, and the particular uranium compound(s) being sought for release. It is surmised that PTFE analogues/homologues and other similar polymers other than PTFE will perform suitably or even better than PTFE for certain core compositions, analytes, coating combinations, sampler applications, or the like.

In regard to the extraction liquid composition, it has been discovered that at least to some extent, the degree of extraction depends on the uranium compound(s) being sought for removal, the relative amount of such compound(s) captured with the sampler, and the strength of one or more active agents of the extraction liquid. For certain preferred embodiments, the extraction liquid includes an organic solvent. Certain embodiments include an acid in the extraction liquid; some more specific embodiments include the acid as a mineral acid type in aqueous solution; and even more specific embodiments include the acid as nitric acid ($HNO_3$) in aqueous solution. While yet other embodiments of the extraction liquid include a base, some specific embodiments include the base as an alkaline agent in aqueous solution, and even more specific embodiments of the extraction liquid include sodium carbonate ($Na_2CO_3$) as the base in aqueous solution. Still other embodiments of the extraction liquid include a mixture of an oxidizer and one or both of onium and carbonate, while in still more specific embodiments the mixture includes an oxidizer in the form of a peroxide and includes one or more of onium and carbonate, and an even more specific embodiment includes the oxidizer in the form of a hydrogen peroxide, and ammonium carbonate. See Experimental Examples Eleven and Twelve for more details regarding uranium detection and related analysis.

It has further been surprisingly discovered that the background uranium present in the sampler can be reduced with certain applications of a PTFE coating. It is surmised that PTFE analogues/homologues and other similar polymers other than PTFE will perform suitably or even better than PTFE for certain core compositions, analytes, coating combinations, sampler applications, or the like. One embodiment for preparing the sampler includes depositing PTFE nanoparticles from a colloidal suspension on a glass fiber core by dipping in or painting on the suspension liquid. Another embodiment for preparing the sampler includes placing the PTFE-coated sampler in a liquid agent to reduce uranium content of the PTFE and/or reduce impurities. Yet another embodiment for preparing the sampler includes applying an acid form of the liquid agent in aqueous solution to the PTFE-coated sampler to reduce background uranium content of the PTFE and/or reduce impurities. An even more specific embodiment for preparing the sampler to reduce uranium content of the PTFE and/or reduce impurities includes applying an oxidizer and one or both of onium and carbonate; and a still more specific embodiment includes peroxide in this oxidizer; and yet an even more specific embodiment includes hydrogen peroxide in the oxidizer and ammonium carbonate. In still other embodiments for the sampler apparatus, the uranium background is less than or equal to 10 ng/g (10 nanograms (ng) of uranium per sampler gram (g)). In more specific embodiments, the uranium background of the sampler is less than or equal to 1.0 ng/g. In even more specific embodiments, the uranium background of the sampler is less than or equal to 0.1 ng/g. In still even more specific embodiments, the uranium background of the sampler is less than or equal to 0.010 ng/g. See Experimental Example Thirteen for more details regarding background uranium reduction and related analysis.

From operation 718, process 700 continues with conditional 720. Conditional 720 tests whether to apply a sampler to test for heavy metals in certain industrial settings. If the test result is negative (No), process 700 falls through to conditional 724. If the test result is affirmative (Yes), process 700 advances to operation 722. In operation 722, a PTFE-coated core sampler or similar arrangement will be swiped on selective surfaces to pick up dust in an industrial setting such as a mine or metal processing plant, where metal-based content will potentially be collected. Next, under operation 722, digestion and complimentary chemical testing will be performed to determine the degree to which a worker will be exposed to certain heavy metals. From operation 722, process 700 moves to conditional 724. Conditional 724 tests if sampler application(s) should be continued. If the test result is affirmative (Yes), process 700 returns to conditional 704 to repeat it and potentially any of operations/conditionals in the range from 706-722 as appropriate. If the test result is negative (No), process 700 halts in stage 726, stopping further sampler applications. There are many different potential contraband or undesirable substances (previously defined) that may be a target analyte for sampler 100. Alternatively, any contraband or undesirable substance not listed therein may be a target of sampler 100 and instrumentation 30. Alternatively or additionally, in further embodiments any non-contraband substance and/or a desired substance may be a target for detection with sampler 100 and instrumentation 30. In yet other embodiments, the substance targeted for detection may be one or more of contraband, non-contraband, undesirable, desirable, or a still different substance of interest.

Samplers (such as sampler 100) have been described in terms of several different innovative mechanical, structural, thermal, and/or compositional/material features, elements, characteristics, properties, and parameters; however, dimensioning, relative or absolute—especially three-dimensional (3-D) qualities has not been a major focus—given that sampler 100 has largely been portrayed as a flat-type with L and W much larger than thickness (L, W>>T1, T2) thus far. Previously, sampler shape has been depicted as being a planar pad, swipe, or strip type such as that shown in FIGS. 1-3. Indeed, as shown in these figures, the samplers appear as two-dimensional planar rectangles with little or effectively no third dimension; however, as a solid object it should be generally understood a working sampler implementation also has a third dimension, although it may be somewhat negligible compared to its other dimensions. Among the embodiments of such planar samplers is one with qualitative stiffness/bending resistance in a range from that of polymer-coated 20 lb. weight print paper through polymer-coated cardstock, or that of a polymer-coated fabric; and to have comparable elastic resilience to "spring-back" or otherwise return to its original planar for—or at least substantially. However, different dimensional, stiffness, and/or elasticity properties are provided in other sampler embodiments, and it should be appreciated that the various sampler embodiments are not limited to the depictions and accompanying exemplary descriptions provided herein in connection with FIGS. 1-3 or otherwise.

Widely used lineal dimension descriptors include length, width, depth, breadth, height, and thickness, but are sometimes used ambiguously, can vary in preferred use from one field to the next, and may be especially context sensitive. To promote a common understanding, three lineal/axial dimensions that are orthogonal to one another (rectangular) are designated for the purpose of describing three-dimensional (3-D) aspects of samplers: length (L) as the largest dimension, height (H) as the smallest dimension, and width (W) as the intermediate dimension. Height H was selected in lieu of thickness to avoid confusion with previously described thicknesses T1 and T2—understanding they all correspond to the smallest dimension. It should be understood that L and W may be approximately equal to each other (L≈W), W and H may be approximately equal to each other (W≈H), and L, W, and H may be approximately equal to each other (L≈W≈H)—thus the general case is described by the inequality expression: L≥W≥H. Indeed, in the case of an ideal right cylindrical embodiment, two of the three dimensions would be equal to each other. Accordingly, as used herein, L, W, and H are oriented in such a manner that as each axis extends along the object being measured the inequality expression L≥W≥H is obeyed. Under this measurement procedure, the absolute longest dimension need not be designated by L as long as L along the object is longer than W, W along the object is longer than H along the object, and L, W, and H are orthogonal. This corresponds to the usual way a rectangular parallelepiped (rectangular solid) would be measured along its outer edges rather than using the absolute longest length, which is the diagonal. For many planar samplers corresponding to the type represented in FIGS. 1-3, the height dimension H may be considerably less than a tenth (1/10th) of the width dimension W—such that width W varies from height H by one order of magnitude or more. Under certain circumstances/applications, samplers so dimensioned (H<<W by at least an order of magnitude) can be considered approximately two-dimensional, similar to those illustrated in FIGS. 1-3.

It has also been discovered a generally nonplanar form of sampler may be desirable under certain circumstances that has height H generally closer to width W than for the planar type, and either or both of height H and width W are comparable to length L. This dimensioning corresponds to a three-dimensional (3-D) sampler type that is more perspectival than generally flat, planar samplers with H<<W. Initially referring to FIG. 24, one type of three-dimensional substance sampler 1000 (alternatively designated collector 1002) is illustrated in the form of substance collection framework 1010. Length L of framework 1010 is represented by the vertical juxtaposed line segment (axis) designated by reference numeral 1012 and the width W of framework 1010 is represented by the horizontal juxtaposed line segment (axis) designated by reference numeral 1014, which are perpendicular to each other and parallel to or coplanar with the view plane of FIG. 24. The height H extends along an axis perpendicular to the view plane of FIG. 24 and is represented by the concentrically arranged circle and cross hairs designated by reference numeral 1006. In one form, L, W, and H of three-dimensional sampler 1000 are all dimensionally within the same order of magnitude. In one embodiment of sampler 1000, H is one-eighth (⅛) or more of W and W is at least five-eighths (⅝) of L. In a more preferred embodiment of sampler 1000, H is three-fourths (¾) or more of W and/or W is at least three-fourths (¾) of L. In an even more specific embodiment of sampler 1000, H is one-half (½) or more of W and W is at least seven-eighths (⅞) of L. In another even more favored embodiment of sampler 1000, none of L, W, and H are more than 1.5 greater than another. In still a more favored embodiment of sampler 1000, none of L, W, and H are more than 1.25 greater than another.

In addition to the dimensional features, various mechanical, structural, thermal, and compositional/material features of sampler 1000 shall be described in connection with FIGS. 24 & 25. However, beforehand FIGS. 22 & 23 are described to better elucidate the complex three-dimensional pattern of framework 1010 shown in FIGS. 24 & 25. By way of introduction, FIG. 22 provides a description of the fundamental mechanical/structural constituent 1005 that corresponds to a geometrically pattern repeated in a coincident fashion to build honeycomb 1030 of FIG. 23. The edges and adjoining vertices of this honeycomb corresponds to the framework 1010 of FIG. 24. In FIG. 23, solid coincident blocks 1034, each are diagrammatically representative of the shape outlined by mechanical/structural constituent 1005, fit together to provide a solid geometry honeycomb 1030 structure used to better explain and visualize the role of its features in the subject sampler 1000 of FIGS. 24 and 25. From the description of the FIG. 23 honeycomb 1030, it transitions to the more complex cage/reticular/lattice-like embodiment of collection framework 1010 of FIG. 24 and further assists in explaining various attendant embodiments. From there, the cross-sectioned framework portion 1080 of FIG. 25 is described to further explain and visualize sampler 1000. FIGS. 24 & 25 conclude by describing various sampler 1000 representative applications and alternative embodiments thereof.

With this summary of FIGS. 22-25 in mind, FIG. 22 is considered next in greater detail. Turning then to FIG. 22, a diagrammatic perspective view of a convex polyhedron in the form of a dodecahedral, truncated octahedron 1008 represented by schematic wireframe structural pattern 1013 is illustrated, with mechanical/structural constituent 1005 corresponding to the illustrated shape; where like reference numerals refer to like features previously described. Truncated octahedron 1008 defines thirty-six (36) edges 1013*a* joined together by twenty-four (24) vertices 1013*b* (a truncated octahedron is equivalently a bitruncated cube). Structural constituent 1005 is provided in the form of a schematically illustrated truncated octahedron framework 1015. Framework 1015 is based on wireframe pattern 1013, which corresponds to edges 1013*a* and vertices 1013*b* of the truncated octahedron 1008. In pattern 1013, the arrangement of edges 1013*a* and vertices 1013*b* define twelve (12) open faces 1017 that correspondingly have twelve (12) facial openings/apertures 1018 that open external to framework 1015 and constituent 1005. Six (6) open faces 1017 are approximately regular, geometrically coincident hexagons 1020, and the remaining six (6) open faces 1017 are approximate, geometrically coincident rectangles 1022 (approximately squares). Furthermore, framework 1015 internally defines a like-shaped chamber 1019. Chamber 1019 intersects the twelve (12) open faces 1017 and corresponding facial openings 1018. Only a few of edges 1013*a*, vertices 1013*b*, faces 1017, openings 1018, hexagons 1020, and rectangles 1022 are designated by reference numerals to preserve clarity.

Correspondingly, truncated octahedron framework 1015 is comprised of link/bar members 1024 each corresponding to a different edge 1013*a*. Bar members 1024 are each elongate, and generally straight with one bar end 1026 positioned opposite another bar end 1026. Three bar ends 1026 come together at a corresponding node/vertex 1013*b* to form a nodal joint 1028. The three joined bar members 1024 extend away from joint 1028 in correspondence to the respective edges 1013*a*. Collectively, thirty-six (36) bar members 1024 and twenty-four (24) joints 1028 define framework 1015, which is also a form of truncated octahedral cage 1021. Bar members 1024 and joints 1028 may be integral to one another, consisting of a single piece of material. Such construction can be performed by mechanical or laser machining, etching, or the like of a unitary piece of material, such as a metal, ceramic, or metalloid. Alternatively, bar members 1024 may be fastened together with mechanical fasteners, by welding, brazing or soldering, by chemical medium/media such as adhesive(s), a 3-D printing technique, or the like. In still other embodiments, a combination of these approaches may be utilized. Only a few of bar members 1024, bar ends 1026, and joints 1028 are designated by reference numeral to preserve clarity. It should further be noted that members 1024 may be coated with a polymer such as that previously described in connection with sampler 100.

Additionally referring to FIG. 23, a diagrammatic, perspective view of a 3-D bitruncated cubic honeycomb 1030 is illustrated that is comprised of geometrically coincident truncated octahedra 1008; where like reference numerals refer to like features previously described. Honeycomb 1030 is also called a truncated octahedrille and is more generally a form of tessellation 1032. Honeycomb 1030 is of a solid geometric form to function as a visualization aide to conceptually bridge understanding from constituent 1005/framework 1015 (FIG. 22) and truncated octahedron 1008 (FIGS. 22 & 23), to framework 1010 (FIGS. 24 & 25). Accordingly, solid truncated octahedral "blocks" 1034 are geometrically solid polyhedrons shown with appropriate shading to illustrate the nature/shape of the honeycomb 1030. It should be appreciated that the shaping and sizing of blocks 1034 renders them approximately coincident relative to one another. As a result, blocks 1034 approximately, if not exactly, occupy the same space if overlapping one another. Blocks 1034 fit together congruently, arranged and shaped in a complementary orientation such that edges 1013*a* and vertices 1013*b* of octahedra 1008 abutting one another can be merged or united because of the respective coincidence. It should be appreciated that not all constituent structures 1005, truncated octahedra 1008, edges 1013*a*, vertices 1013*b*, and truncated octahedral blocks 1034, are designated by reference numerals in FIG. 23 to preserve clarity.

Referring collectively to FIGS. 22-24, substance collection framework 1010 of sampler 1000 is further described; where like reference numerals refer to like features previously described. Truncated octahedral framework 1010 is a form of tessellation 1032 similar to honeycomb 1030. Analogous to the arrangement of honeycomb 1030, framework 1010 may be conceptualized as the merger/union or congruent interconnection of pairs of coinciding bar members 1024 and pairs of coinciding joints 1028 that come together as adjacent truncated octahedral frameworks 1015 are fit together. In other words, in effect, a single bar member 1024 and joint 1028 is substituted for each of the respective coincident pairs. The general coincidence of frameworks 1015 from one to the next facilitates such conceptualization, which is analogous to the truncated octahedral blocks 1034 of bitruncated cubic honeycomb 1030. Framework 1010 corresponds to a form of wireframe 1011 outlining a bitruncated cubic honeycomb shape. Also, the arrangement of bar members 1024 and joints 1028 of framework 1010 collectively define a form of cage 1044. In further description, framework 1010 is generally a form of openwork 1052, defines a reticular/reticulated structure 1054, and is a type of lattice 1056.

As to internal interspatial and external spatial aspects of framework 1010, the alignment of open faces 1017 of hexagons 1020 and rectangles 1022 form recesses in the form of internal passages 1040 that intersect one another in several different directions to form a passage network 1042. Passage network 1042 defines chamber 1046 bounded by the outermost bar members 1024 and outermost joints 1028. Chamber 1046 is comprised of adjacent truncated octahedral-shaped chambers 1019 each corresponding to a different truncated octahedral framework 1015 (see also FIG. 22). Internal to framework 1010, interspatial intersections between adjacent chambers 1019 result through open faces 1017/facial openings 1018 that are defined by corresponding bar members 1024 and vertex joints 1028. Furthermore, outermost facial openings 1018 correspond to external apertures 1048 that open externally—such that chamber 1046 opens/intersects external space through apertures 1048. Only a few of edges 1013*a*, vertices 1013*b*, truncated octahedral frameworks 1015, open faces 1017, facial openings 1018, chambers 1019, hexagons 1020, rectangles 1022, bar members 1024, joints 1028, passages 1040, and apertures 1048 are designated by reference numerals to preserve clarity.

Referring additionally to FIG. 25, the construction/formation of framework 1010 is next considered. In the illustrated embodiment, framework 1010 is comprised of a like-shaped support structure core 1062 coated with a polymer 1070. Accordingly, in some embodiments, it is desirable to form support structure core 1062 before any polymer 1070 is applied so the manufacturing techniques are generally described in terms of support structure core 1062 rather than framework 1010 given the possible absence of polymer 1070 coating. Nonetheless, in some other embodiments, support structure core 1062 may be partially or completely coated by polymer 1070 before or during manufacture. Generally, except where applicable description is provided in terms of support structure core 1062 rather than framework 1010, based on the general understanding that the timing of polymer 1070 coating could greatly vary depending on the selected manufacturing procedure—understanding for some polymer 1070 cannot be applied until after core 1062 is at least partially formed as further described hereinafter. Further compositional details are deferred until FIG. 25 is addressed in detail hereinafter.

While the concept of applying multiple frameworks 1015 to visualize the internal structure of framework 1010 (and correspondingly support structure core 1062) may be informative; it should be understood that framework 1010 may or may not actually be made from multiple frameworks 1015 depending on the selected manufacturing procedure; however, framework 1010, framework 1015, and support structure core 1062 all still appropriately use the same bar members 1024 and joints 1028 in view of the framework 1015 relationship to framework 1010 and support structure core 1062. In some embodiments not amenable to application of multiple frameworks 1015, support structure core 1062 is formed from a single, unitary piece of material—with portions of support structure core 1062 corresponding to bar members 1024 and vertices 1028 being integrally shaped. In such embodiments, laser and/or mechanical machining, etching, possibly casting or extruding in whole or in part, or the like may be used to make support structure core 1062. In a further embodiment, a standard "3-D printing" technique is utilized, such as those shaping a series of layers that are stacked and joined together to provide the desired article. In other embodiments, one or more of these techniques are utilized to make support structure core 1062 from relatively few parts (such as two halves, four quarter parts, or the like) that may be connected together using other suitable mechanical, thermal, and/or chemical joining techniques, some of which are described further below.

In yet other embodiments, support structure core 1062 may be partially or completely assembled by mechanical fasteners, by welding, brazing, or soldering, by chemical agency, such as bonding parts together with adhesive(s), or the like. In certain forms of such embodiments, framework 1010 is comprised of multiple frameworks 1015 joined together. For such forms, as two frameworks 1015 are fit together, each pair of coincident bar members 1024 and joints 1028 may be complementarily shaped and/or sized to approximate merger/union of each pair into a single bar member 1024 and a single joint 1028. Coincident joints 1028 complementally unite/merge in correspondence with the effective substitution of each pair of bar members 1024 by a single bar member 1024. In one variation of such forms, single bar members 1024 and vortex joints 1028 are substituted for each corresponding coincident pair. Further embodiments combine some or all of these techniques to provide support structure core 1062 and/or may be partially or completely coated by polymer 1070 before or during manufacture where appropriate.

In FIG. 25, a diagrammatic, planar cross-sectional view of the three-dimensional sampler 1000 is depicted; where like reference numerals refer to like features. The cross-section is taken along a plane approximately parallel to the view plane of FIG. 24 and illustrates sectioned portions 1050 with cross-hatching. The sectioned sampler 1000 further illustrates framework 1010 in part, more specifically designated as cross-sectioned framework portion 1080. While briefly introduced already, compositional configuration 1060 of framework portion 1080 is more specifically described attendant to the depiction in the vicinity of the sectioned portions 1050. This depiction contrasts support structure core 1062 composition (cross-hatched) from adjacent portions to which polymer 1070 have been applied. Generally, it should be understood that framework 1010 may be rigid, semi-rigid, or somewhat flexible. In addition, in some embodiments, thermal performance compatible with thermal desorption of a collected sample and/or thermal cleaning of sampler 1000 would be desirable, while in other embodiments different thermal performance is desired. Accordingly, the composition of support structure core 1062 in one form is comprised of one or more of: glass, polymeric thermoplastic, polymeric thermoset, glass, metal, metalloid, inorganic oxide, ceramic, and glass-ceramic. In one specific embodiment, the composition of support structure core 1062 includes metal, metalloid, metal oxide, ceramic, or glass-ceramic. Still a more specific embodiment is comprised of metal, carbon, metal oxide, ceramic, or glass-ceramic. In another preferred embodiment, the composition of support structure core 1062 includes carbon. In a more favored variation of this embodiment, the carbon composition is anisotropic in terms of strength and/or thermal performance. In yet a further favored embodiment, the support structure core 1062 includes one or more carbon allotropes as previously described. In still another preferred embodiment, the composition of support structure core 1062 includes ceramic material. Only a few of sectioned portions 1050 are designated by reference numerals to preserve clarity.

Compositional configuration 1060 further comprises polymer 1070 applied to the support structure core 1062 to at least partially coat or cover all surfaces thereof. In one preferred embodiment, polymer 1070 provides an approximately complete covering of support structure core 1062. Internally, the polymer at least partially lines internal passages, chambers, and the like. In an even more favored form, internal surfaces of core 1062 are generally completely lined. Polymer composition may be the same as any of the embodiments previously described in connection with sampler 100.

In application, a selected surface is swiped, skimmed, rubbed, or otherwise contacted with 3-D sampler 1000 in a manner like that described for sampler 100. Likewise, sampler 1000 may be directed to any of the various sampling targets previously described in connection with sampler 100. Internal passages 1040 of network 1042/chamber 1046 that are externally open through intersection with apertures 1048 operate during the sampling activity to intake various substance(s) of interest (if present in trace amount(s)) and temporarily trap the same within chamber 1046 or on interstitial bar members 1024 internal to sampler 1000 either physically, mechanically, and/or chemically. Such mechanisms may correspond to those described previously in connection with sampler 100 where the influential parameters are of like type. Instrumentation 30 or other detection equipment like that previously listed is adapted to receive 3-D sampler 1000 directly for thermal desorption processing and/or receives the sample by rinsing and/or treatment of sampler 1000 with one or more agents to release/prepare the sample. Once prepared, the sample is processed in the previously described manner, as applicable. In one embodiment, sampler 1000 is of particular applicability with the collection of uranium, plutonium, and heavy metals that typically are released from sampler 1000 through liquid treatment/rinsing/processing/preparation with appropriate agents as described previously and further described in connection with Experimental Examples 11-13. In a further embodiment particularly directed to radioisotope nuclear material sampling, (like uranium and plutonium), radioactive decay detection equipment appropriate to the expected decay type(s)/substance isotopes may be used (alpha particle, beta particle, and/or gamma ray detectors).

Many further embodiments of the present application are envisioned. For example, a method of the present application comprises: providing a sampler including an inorganic fiber core and a polymer applied thereon with background uranium of less than or equal to 10 ng/g; selecting a surface with dust thereon; collecting at least a portion of the dust with the sampler; chemically processing the sampler to analyze the dust for uranium content. In one refinement, the inorganic fiber core is comprised of at least one of glass, metal, metalloid, inorganic oxide, ceramic, and glass-ceramic and the polymer includes PTFE with background uranium of less than or equal to 1 ng/g. In another refinement, the core material is comprised of one or more of: HSG, metal, metalloid, metal oxide, ceramic, glass-ceramic and the polymer is comprised of PTFE with background uranium of less than or equal to 0.1 ng/g. In a further refinement, the core is comprised of one or more of: HSG, metal, carbon, and metal oxide and the polymer is comprised of PTFE with a background uranium level of less than or equal to 0.01 ng/g. In an alternative refinement, the inorganic fiber core is made of carbon and/or S-glass and the polymer is made of PTFE with a background uranium level of less than or equal to 0.01 ng/g.

In another example, a method, comprising: providing a sampler including an inorganic fiber core and a polymer applied thereon; selecting a surface with dust potentially containing one or more heavy metals (previously defined); collecting at least a portion of the dust with the sampler; chemically processing the sampler to analyze the dust for heavy metal content. In one refinement, the inorganic fiber core is comprised of at least one of glass, metal, metalloid, ceramic, glass-ceramic, and inorganic oxide, and the polymer includes at least one of: polymeric organofluorine, polyamide, polyimide, PDMS, PBI, PFSA, and PPPO. In another refinement, the core material is comprised of one or more of: HSG, metal, metalloid, metal oxide, ceramic, glass-ceramic and the polymer is comprised of one or more of: perfluorocarbon, perfluoroether, ETFE, FEP, THV, PVdF, and PPPO. In a further refinement, the core is comprised of one or more of: HSG, metal, carbon, and metal oxide; and the polymer is comprised of PTFE. In an alternative refinement, the inorganic fiber core is made of carbon and/or S-glass and the polymer is made of PTFE.

Another example is directed to an analyte sampler to collect and release one or more contraband or undesirable substances, the sampler includes: a woven fabric of S-glass fibers, the fabric having a closed weave of satin and/or twilled weave type; a polymer applied to the fabric, the polymer being comprised of polytetrafluoroethylene; and the sampler having a thickness less than or equal to 0.3 mm and a flexural modulus equal to or less than 3 GPa.

A further example is directed to a detection system comprising: a sampler including a fabric core with a polymer applied thereto, the fabric core being comprised of S-glass; and a thermal desorption IMS detector structured to receive the sampler. In a further refinement, the sampler has at least one of: a flexural modulus of greater than or equal to 1 GPa, the fabric core with a thickness of about 0.3 mm or less, and a calcined polymer content in a range of about 20% wt through about 40% wt.

A different example is directed to a method of detecting a contraband or undesirable substance, comprising: collecting the contraband or undesirable substance on a sampler, the sampler including a fabric with a first polymer layer applied thereto and a second polymer layer applied on the first layer, the fabric being comprised of one or more of: HSG, metal, metalloid, inorganic oxide, ceramic, and glass-ceramic, the first polymer layer and the second polymer layer each being comprised of one or more of: polymeric organofluorine, polyamide, polyimide, PBI, PDMS, PFSA, and PPPO; transferring the contraband or undesirable substance from the sampler to detection instrumentation; and detecting the contraband or undesirable substance with the instrumentation. In one refinement, the inorganic fiber core is comprised of at least one of HSG, metal, metalloid, metal oxide, ceramic, and glass-ceramic. In another refinement, the core material is comprised of one or more of: HSG, metal, carbon, metal oxide, ceramic, glass-ceramic and the polymer is comprised of one or more of: perfluorocarbon, perfluoroether, ETFE, FEP, THV, PVdF, and PPPO. In a further refinement, the core is comprised of one or more of: HSG, metal, carbon, and metal oxide; and the polymer is comprised of PTFE. In an alternative refinement, the inorganic fiber core is made of carbon and/or S-glass and the polymer is made of PTFE.

A further example is directed to a method of making a sampler, comprising: providing a fabric core; applying at least a partial particle fill to the fabric core to alter thermal conductivity of the sampler, the particle fill being comprised of one or more types of inorganic metallic material; applying polymer to the fabric core; heating the fabric core and the polymer after application to the fabric core to provide the sampler. One refinement includes heating the fabric core before the applying of the polymer. Another refinement includes functionalizing the core/substrate before polymer application. Still a further refinement includes the polymer comprising a first polymer layer and further applying a second polymer layer on the first polymer layer that may be the same composition or a different composition. In one refinement, the particle fill material is comprised of one or more nanoparticles of: metal, metalloid, and metal oxide, and the polymer includes at least one of: polymeric organofluorine, polyamide, polyimide, PDMS, PBI, PFSA, and PPPO. In another refinement, the particle fill material are nanoparticles comprised of one or more of: carbon and metal oxide; and the polymer is comprised of one or more of: perfluorocarbon, perfluoroether, ETFE, FEP, THV polymer, PVdF, and PPPO. In an alternative refinement, the particle fill comprises nanoparticles including one or more of: alumina, nanotubes of carbon, and/or graphene; and the polymer is made of PTFE.

Yet another example is directed to a method of making an sampler for one or more contraband or undesired substances, comprising: providing an inorganic fabric core defining a surface; performing a silane functionalization of the surface to provide an affinity to the one or more analytes and improved polymer application to the core; applying a first polymer to the fabric core; heating the fabric core and the polymer after application to the fabric core to provide the sampler. One refinement includes heating the fabric core before the applying of the polymer. Still a further refinement includes applying a second polymer layer on the first polymer layer. Alternatively or additionally, another refinement includes applying at least a partial particle fill to the fabric core to alter thermal conductivity of the sampler before the performing of the silane functionalization, the particle fill being comprised of one or more of: metal, carbon, and a metal oxide.

In yet a further embodiment, a device, comprises: a sampler to collect and release one or more contraband or undesirable substances, the sampler including: a woven fabric of S-glass fibers, the fabric having a 4 HS weave; and a polymer applied to the fabric, the polymer being comprised of polytetrafluoroethylene. Various refinements of this device are as follows: wherein the sampler fabric has a thickness less than 0.3 mm and a flexural modulus of at least 3 GPa; which includes means for thermally cleaning the sample and thermally releasing the one or more contraband or undesirable substances from the sampler; and/or which includes means for analyzing the one or more contraband or undesirable substances released to detect the same.

Next, various alternative embodiments of a 3-D sampler of the type described in connection with FIGS. 22-25 are considered. In one such alternative, coincident cube-shaped constituents are provided by structural bar linkages extending in three different approximately orthogonal directions and intersecting one another to define adjoining nodes of four linkages, and corresponding to the shape of a cubic honeycomb and further define external passage openings in different directions (approximately orthogonal to one another); where the core is at least partially coated by one or more polymer types previously described. In certain further alternative embodiments, a 3-D sampler collection framework includes a cage-type structural core comprised of: ceramic, metal, metal oxide, glass, glass-ceramic and/or metalloid, which has structural linkage members and nodal joints corresponding to the edges and vertices of a convex polyhedron that defines several passages opening externally, and with one or more polymers of any of the types previously described applied thereto, at least partially coating the same. In at least some of these alternative embodiments, the convex polyhedron is one or more of: a geometric convex uniform honeycomb, a convex space-filling polyhedron, and an archimedean solid.

Still further alternative embodiments of a 3-D sampler collection framework includes a cage-type structural core comprised of: ceramic, metal, glass, glass-ceramic, metal oxide, and/or metalloid; at least a portion of which corresponds to approximately a parallelepiped, dodecahedral, icosahedral, cuboctahedral, icoidodechedral, spherical, ellipsoidal, cylindrical, conical, or truncated-cone shape made of adjoined structural linkage members representative of corresponding edges and vertices and that define several passages externally opening in different directions; where the core is at least partially coated by one or more polymer types previously described.

In yet another alternative embodiment, a structural core comprised of one or more of: metal, ceramic, glass, metal oxide, glass-ceramic, and/or metalloid includes a number of passages that are formed by approximately helical coils joined together; where each coil externally opens to collect and trap a substance that is a sampling target and to which a previously described polymer may be applied to provide at least a partial coating.

Still certain other alternative 3-D sampler embodiments differ from those previously described by lacking any generally discernable solid geometry classification, and may include a random or pseudorandom arrangement of structural members; where such members defined a 3-D openwork, cage, lattice, reticular, and/or other backbone structure providing: recesses that define external openings thereto and/or may recede inward sufficiently to provide a passage into the structure that may intersect another passage or chamber, or may extend therethrough; and/or passages defining external openings. Such recesses/passages with external openings receive and trap substance(s) targeted for sampling and may be at least partly coated by one or more polymers previously described.

Further alternative embodiments are directed to a 3-D sampler provided in the form of a pad including a structural core comprised of one or more of: glass, metal, ceramic, metalloid, and glass-ceramic, that defines a number of passageways each externally opening along at least one face of the pad; where the core is coated by a polymer previously described. Other alternative embodiments include one or more of the treatments, options, enhancements, and/or processes previously described in connection FIGS. 1-21, including, but not limited to: (a) surface activation by silanization or other functionalization procedure; (b) specifically processing to provide a surface phenol functional group; (c) at least partly filling with particles (such as nanoparticles) of a metal oxide (including without limitation alumina), a metal, one or more allotropes of carbon, and/or a different element or compound; (d) providing two or more applications of polymer—such applications each being the same or different compositions; (e) providing a polymer thickness in accordance with any of the previously disclosed ranges or other limits; (f) applying polymer in any of the alternative % wt listings previously described; and/or any others as previously described with any of FIGS. 1-21 herein.

In another embodiment, a method to detect as substance, includes: collecting the substance with a sampler including a structural core, the structural core being comprised of one or more of: ceramic, metal, and metalloid; a polymer applied to at least partially coat the core, the polymer being comprised of one or more of: polymeric organofluorine, polyamide, polyimide, PBI, PDMS, PFSA, and PPPO; the sampler defining several recesses therein that externally open to receive the substance; transferring the substance from the sampler to detection instrumentation; and detecting the substance with the instrumentation. In one refinement, at least some of the recesses may be defined by external openings with passages receding into the core.

Still another embodiment is directed to a system, comprising: means for collecting a substance, the collecting means including a structural core, the structural core being comprised of one or more of: glass, polymeric thermoplastic, polymeric thermoset, ceramic, metal, metal oxide, metalloid, and glass-ceramic; means for at least partially coating the structural core; the structural core including means for defining several recesses and/or passages extending into the structural core that externally open to receive the substance; means for transferring the substance from the collecting means to detection instrumentation, the detection instrumentation including means for analyzing the substance.

Yet another embodiment is directed to a method to detect a substance including uranium, comprising: collecting the substance with a sampler at least partially coated with a polymer; performing liquid extraction of the substance from the sampler after the collecting of the substance with the sampler; and detecting the uranium in the substance from the liquid extraction. In one form, the polymer includes PTFE. In another form, the polymer comprises any of those previously described in connection with polymer application to a core.

A further embodiment is directed to an apparatus to detect a substance including uranium, comprising: means for collecting the substance, the collecting means being at least partially coated with a polymer including PTFE; means for performing liquid extraction of the substance from the collecting means; and means for detecting the uranium in the substance from the liquid extraction. In another form, the polymer comprises any of those previously described in connection with polymer application to a core.

EXPERIMENTAL EXAMPLES

The following experimental examples are exemplary only, being empirical in character, and should not in any way limit the inventions defined by the claims set forth herein.

Example One

This first experiment was performed with a sampler prepared in accordance with process 400 at Pacific Northwest National Laboratory (PNNL), a facility managed by the Assignee of the present application. This PNNL sampler was made from S-glass/4 HS woven fabric with PTFE polymer applied thereto. The fabric thickness was less than or equal to about 0.3 mm and PTFE application was less than or equal to 35% by weight. The PTFE coating was created by painting a colloidal slurry of suspended particles on the core fabric surface followed by evaporation of the solvent. The slurry was prepared using DUPONT TEFLON PTFE TE-3859 aqueous dispersion. It contained negatively charged, 0.05 to 0.5 micrometer ($\mu$m) PTFE resin particles suspended in water, and about 6% (by weight of PTFE) of a nonionic wetting agent and stabilizer.

The PNNL sampler was compared to sampling swipes sourced from: (a) SARFRAN MORPHO (MORPHO) and (b) DSA DETECTION (DSA). The DSA and MORPHO sampling swipes used for the comparison were commercially available materials. Data was taken with a BARRINGER IONSCAN 400A ion mobility spectrometer (SMITHS DETECTION) via thermal desorption. This instrument was operated in negative ion mode at a thermal desorption temperature of 180° C. and a collection time of 10 s. The drift and inlet temperatures were set at 114° C. and 240° C., respectively. The sample gas was set at 239 mL/min and the drift gas at 351 mL/min, as per standard instrument settings.

FIG. 9 is a comparative graph illustrating magnitude versus time responses of samplers from the three different sources to a 10 nanogram (ng) sample of TNT (hand spiked) as detected with the indicated IMS detector. Describing the data plots in top to bottom order of the inset legend: (1) the "X" data point plot represents the response of the PNNL sampler embodiment of the present application—it has the highest peak and quickest peak response, (2) the "hollow triangle" (Δ) data point plot represents the response of the MORPHO brand of sampler that is intermediate in terms of peak magnitude and speed, and (3) the "filled diamond" (♦) data point plot represents the response of the DSA brand of sampler with the slowest and lowest peak response. The relatively higher response of the PNNL sampler illustrates its superior performance under like conditions. It is theorized that the use of a relatively thin S-glass for the fabric core and/or a relatively modest amount of PTFE polymer resulted in higher thermal conductivity, higher gas permeability, and reduced thermal mass to provide a better TNT signal response of the PNNL sampler.

Example Two

This second experiment compared the responses of differently prepared PNNL samplers to a TNT 10 ng sample, as reflected in Table I that follows:

TABLE I

| Sampler Material | Average of IMS signal of 10 ng TNT |
|---|---|
| Core thick E-glass | 351 |
| Core thick S-glass | 555 |
| Core thin E-glass | 588 |
| Core thin S-glass-phenyl | 911 |
| Core thin S-glass-phenyl-PTFE | 781 |

For Table I, data was taken with a BARRINGER IONSCAN 400A ion mobility spectrometer (SMITHS DETECTION) using conditions/parameters like those for Example One. The different sampler configurations correspond to the entries in the left hand column of Table I. The maximum TNT signal from the sampling material was averaged and reported in the right hand column of Table I. The first three entries of Table II resulted from samples taken with three different core/substrate material configurations without application of a polymer thereto, which in like order (top to bottom) are: thick E-glass core, thick S-glass core, and thin E-glass core. The fourth entry of Table I is for a sampler prepared from thin S-glass and functionalized per operation 414 of process 400 to provide phenyl terminal groupings (See FIG. 7), but still lacking any polymer application. The fifth and final entry of Table I is prepared in the same manner as the fourth sample, but also has PTFE polymer applied in accordance with operation 416 of process 400. It has been discovered through such experimentation that the application of a polymer like PTFE may controllably increase stiffness of the sampler as a function of the amount applied and other operations/treatments, such as heat applied to cure the PTFE.

Table I relates to properties and parameters useful for the development of suitable samplers with varying stiffness, including: the composition of the substrate/core (in this case E-glass or S-glass), substrate/core thickness (whether "thick" or "thin"), surface chemistry (functionalization), and polymer application. For a given core type and thickness, the sampler stiffness can be controlled with the amount of polymer applied and/or heat treatment used to cure the polymer. A certain degree of stiffness/flexure is desired in some embodiments to provide for more suitable handling, detector equipment interfacing, and longevity, among other things. It should be appreciated that the fabric core sampler material of S-glass fibers provides higher IMS signals as compared to E-glass fibers even without functionalization (like that of operation 414) or polymer application (like that of operation 416), which is theorized to be due to its better thermal properties. Indeed, the thinner sampler core appears to significantly improve the IMS signal, which may be because of improvement in mass transport of the analyte out of the sampling material during a thermal desorption analyte release/transfer. The phenyl silane surface functionalization of thin S-glass (fourth entry of Table I) indicates performance improvement relative to TNT release. Per the fifth/final entry of Table I, the PTFE polymer application to the core and functionalized thin S-glass core combination provides the stiffness and other properties desired for some robust applications; however, indicates a trade-off in terms of a slightly reduced IMS signals. This reduction is most likely due to the change of mass transfer and/or surface chemistry alteration because of the PTFE application.

Example Three

Experimental Example Three relates to the varying performance of different PTFE-coated core/substrates used for trace analyte detection (See FIG. 10). It should be appreciated that a thermal desorption sampler used with IMS, gas chromatography, or the like preferably has good thermal conductivity and low specific heat capacity to facilitate rapid desorption heating. A comparison of these properties for various candidate core/substrate materials at 25° C. was determined as provided in Table II as follows:

TABLE II

| Core Material | Thermal Conductivity (W/m-K) | Specific heat capacity (J/g-° C.) |
|---|---|---|
| E-glass Fiber[A, B] | 1.28-1.32 | 0.78-0.82, 0.803 |
| S-glass Fiber[A, B] | 1.44-1.46 | 0.72-0.75, 0.736 |
| Stainless Steel[C, D] | 16.2, 10-30 | 0.5, 0.2-0.62 |
| Carbon Fiber[E, F] | 21-180, 10 | 0.795 |
| $Al_2O_3$[G-J] | 28-35 | 0.45-0.955, 0.78 |
| Polyamide[K] | 0.23-0.29 | 1.26-1.7 |
| PTFE[K] | 0.25 | 1.0 |
| PVDF[L] | 0.19 | 1.2-1.6 |
| PDMS[M] | 0.25 | 1.46 |
| Cotton/muslin[N] | 0.071 | 1.335 |
| Cellulose[N] | 0.242 | 1.338 |
| Polytetrafluoroethylene[C] | 0.25 | 1.00 |
| Silica[O] | 1.30 | 0.937 |
| Nichrome V[C] | 14.0 | 0.480 |
| Titanium[C] | 17.0 | 0.528 |
| Nickel[C] | 60.7 | 0.460 |
| Platinum[C] | 69.1 | 0.134 |
| Iron[C] | 76.2 | 0.440 |
| Tungsten[C] | 163 | 0.134 |

TABLE II-continued

| Core Material | Thermal Conductivity (W/m-K) | Specific heat capacity (J/g-° C.) |
|---|---|---|
| Aluminum[C] | 210 | 0.900 |
| Gold[C] | 301 | 0.128 (25° C.) |
| Copper[C] | 385 | 0.385 |
| Silver[C] | 419 | 0.234 |

[A]JPS Composite Materials databook. http://jpsglass.com/
[B]Lubin, G. Handbook of fiberglass and advanced plastics composites, Robert E. Krieger Pub. Co.: Huntington, N.Y, 1969.
[C]MatWeb Material Property Data. http://www.matweb.com/index.aspx
[D]http://www.lenntech.com/stainless-steel-3161.htm
[E]http://www.christinedemerchant.com/carbon_characteristics_heat_conductivity.html
[F]http://www.aerosol.co.il/files/article/1315850055u55QN.pdf
[G]Lu, X. and Xu, G. Thermally conductive polymer composites for electronic packaging, Journal of Applied Polymer science, 1998, 65, 2733-2738.
[H]http://www.engineeringtoolbox.com/thermal-conductivity-d 429.html
[I]http://aries.ucsd.edu/LIB/PROPS/PANOS/al2o3.html
[J]http://www.azom.com/properties.aspx?ArticleID=52
[K]Martienssen, W. and Warliment, H (Eds). Springer Handbook of Condensed Matter and Material data, Spinger Berlin Heidelberg.: Germany, 2005.
[L]http://fluorotherm.com/Properties-PVDF.asp
[M]http://www.mit.edu/~6.777/matprops/pdms.htm
[N]Curtis, L.J., Miller, D.J., Transport Model with Radiative Heat Transfer for Rapid Cellulose Pyrolysis. Ind. Eng. Chem. Res., 1988, 27, 1783-1788
[O]http://www.tekna.com/powder/spherical-powder/silica.html From Table II, it was observed that metal (like stainless steel, row three of Table II), carbon (row four of Table II), and metal oxide (like alumina, row five of Table II) have thermal conductivity (column two of Table II) and specific heat (column three of Table II) parameters better than glass fibers (such as E-glass and S-glass, respectively rows one and two of Table II), making them attractive as sampler materials from a thermal desorption perspective; however, other considerations can limit application. For instance, carbon, stainless steel, and other metal meshes/fabrics tend to be expensive compared to glass fiber fabrics, and surface functionalization of proved more difficult. Metal oxides have similar limitations. Furthermore, these materials can scratch certain test article surfaces. Also, carbon surfaces can promote rapid oxidation of TNT through TNT methyl groups, and may chemically interact with other analytes in an unacceptable manner. Nonetheless, it has been found that a carbon core fully covered with PTFE exhibits excellent release of TNT for thermal desorption purposes. Nonetheless, all these metals, metal oxides, carbon, and the like can find application in certain embodiments—especially depending on target analyte(s) and particular treatments applied thereto. In FIG. 10, results for other PTFE-coated core materials are graphically presented as comparative plots of magnitude versus time responses of samplers to a TNT 10 ng sample using thermal desorption IMS with setup/conditions comparable to Experimental Example One. For Example Three, 6-10% wt PTFE coating was applied to each core and all samples were heated at 400° C. in a furnace for 30 minutes prior to testing.

Describing the data plots in top to bottom order of the inset legend: (1) the "filled diamond" (♦) data point plot represents a PTFE-coated stainless steel core response—it has the highest peak; (2) the "filled circle" (●) data point plot represents a PTFE-coated thin S-glass core response—it has the second highest peak; (3) the "filled square" (■) data point plot represents a PTFE-coated thick S-glass core response—it has the third highest peak; and (4) the "filled triangle" (▲) data point plot represents a PTFE-coated thick E-glass core response—it has the lowest peak. Per FIG. 10, PTFE-coated stainless steel had better TNT release performance than PTFE-coated glass fibers of the E- or S-type—theorized to be due to stainless steel's higher thermal conductivity and lower specific heat compared to glass fibers per Table II.

Both Examples Two and Three demonstrated that a thin core material releases the analyte faster—providing a higher and sharper peak compared to a thick core/substrate material with the same surface chemistry. From this empirical information, it is theorized that a thinner sampler reduces the thermal mass, and further improves thermal desorption release while decreasing desorption time at which the maximum signal can be achieved. As indicated in Table II, S-glass fiber has intrinsically better thermal properties (higher thermal conductivity and lower specific heat) than E-glass fiber, which results in faster thermal desorption of the analytes. As can be observed by the area under the response plots, S-glass fiber releases a larger fraction of the spiked analyte compared to E-glass fiber in Example Three.

Example Four

Referring to FIG. 11, the influence of fabric weave and yarn pattern for glass fiber was demonstrated. FIG. 11 presents a graph that compared magnitude versus time responses of two samplers with different cores to a TNT 10 ng sample when tested by IMS under experimental setup/conditions comparable to those described for Experimental Example One. Describing the data plots in top to bottom order of the inset legend: (1) the "X" data point plot represents the response of a 4 HS weave pattern comprised of thin E-glass fibers with 225 yarn pattern—it has the highest peak, and (2) the "hollow triangle" (Δ) data point plot represents the response of an 8 HS weave pattern comprised of thin S-glass fibers with 450 yarn pattern—it peaks at a slightly lower value. Both plots peak at comparable times. There are inset computer-generated images of the 4 HS and 8 HS weaves with like labeling. Both the E-glass fiber 4 HS weave/225 yarn pattern fabric sampler and S-glass fiber 8 HS weave/450 yarn pattern fabric sampler had approximately the same fabric thickness of 0.1 mm with similar (~25%) PTFE weight coating, and both were treated at 340-375° C. in a furnace for 2 minutes.

FIG. 11 indicated how the core weave pattern can impact particle pickup and analyte recovery. As shown therein, the 4 HS weave with 225 yarn strand weight/count (typically in strand yards per 0.01 pound=yards/0.01 lb.) on thin E-glass fiber fabric is significantly more efficient at releasing TNT from the sampling surface than the 8 HS weave with 450 yarn strand weight/count on thin S-glass fiber fabric despite better thermal conductivity and lower specific heat of the S-glass fiber fabric. Because the E-glass fiber results are better, it indicates the impact weave pattern can have on analyte recovery. It is theorized that the enhanced desorption of the E-glass fabric results from the higher gas permeability of the 4 HS weave/225 yarn strand weight/count compared to the 8 HS weave/450 yarn strand weight/count of the S-glass fabric. From this experiment, it is theorized that higher gas permeability results in better analyte mass transport of the thin material. Data was taken on the same day and with the same instrument. Suitable weave/yarn pattern varies with the application and detection system used. Typically, different detection systems also may have different responses to released analytes. The weave and yarn pattern also significantly impacted the collection of materials from the surface. It is hypothesized that S-glass material should be a higher grade weave material for superior performance. Moreover, for installation of surface chemistry silanes per the '910 patent, S-glass may be a better substrate as it generally contains a higher density of surface silanol sites for ligand loading than E-glass.

Overall, Tables I & II, and FIGS. 10 & 11 show that thickness, type, and weave/yarn of glass fiber make significant contributions to the thermal desorption releasing ability of TNT from corresponding samplers. Glass fiber and many other inorganic materials have thermal properties acceptable for use as a sampling medium for thermal desorption analysis. Generally, for glass fibers a combination of inorganic oxide compounds form active surfaces for collection of analyte(s). Sometimes, these active surfaces bind more strongly than desired to target analytes, hampering release. Thus, coating and/or lamination of glass fibers with a suitable material, such as PTFE, can provide an attractive alternative. Polymer composition and other characteristics can be varied to serve different purposes, such as to: cover overly active glass fiber surface sites, provide a desired degree of sampler stiffness/rigidity, increase target analyte collection ability, and enhance thermal desorption of target analyte(s).

Example Five

Various polymer coatings on thin S-glass were studied and compared for TNT release capability as set forth in Table III as follows:

TABLE III

| Polymer Coating | Thermal decomposition (° C.) | Average IMS signal of 10 ng TNT |
| --- | --- | --- |
| PTFE | 448 | 503 |
| PDMS | 250 | 121 |
| PVdF | 355 | 5 |
| PBI | 540 | 0 |
| TENAX TA | 502 | 352 |
| TENAX TA after PTFE coating | 448 | 438 |
| TENAX GR | 502 | 302 |
| TENAX GR after PTFE coating | 448 | 496 |

In Table III, all polymers were coated on thin S-glass with a 3% wt-6% wt concentration range, except for PTFE and PDMS, where 20% wt was used. After coating, the samplers were then thermally treated at temperatures of 120-150° C., except for the PTFE coating, which was treated at 360° C. Thermal decomposition information of Table III was obtained via Thermal Gravimetric Analysis (TGA) data. The maximum TNT signal from the sampling material was averaged and reported. IMS setup/conditions comparable to those for Experimental Example One were utilized.

The thin S-glass fiber fabric qualitatively acquired increased stiffness/rigidity after being coated with these polymers, as did other polymers, except in the case of PDMS. The PTFE polymer provided the highest signal for TNT thermal desorption release when compared to the other polymers (Table III). Surprisingly, there was no occurrence of TNT signal from PBI, which is known to have high thermal stability—suggesting that some polymer compositions demonstrate better adsorption ability than desorption for TNT. TENAX TA (PPPO) and TENAX GR (PPPO/graphite) demonstrate TNT desorption behavior of more interest than several of the other polymers. The release of TNT was pronounced when TENAX was coated after PTFE coating to provide a double coating layer of different polymer compositions (PPPO or PPPO/graphite on PTFE) of the type illustrated in FIG. 7. While these mixed polymers tend to be more responsive than some other polymer applications, these mixed polymers did not provide a better TNT release signal than the PTFE coating alone in this experiment. Both TENAX TA and TENAX GR polymers were obtained from dissolved beads of the same. The beads were dissolved in dichoromethane for a few days or until the beads were mostly dissolved.

Example Six

For Experimental Example Six, PTFE-coated thin fiber S-glass was chosen for further study and development because it provided the highest signal of TNT thermal desorption release in conjunction with high thermal stability (high thermal decomposition temperature in Table III). PTFE is relatively chemically inert, thermally stable, and highly hydrophobic, and the surface properties and structures of PTFE change as a function of cure temperature. At room temperature, PTFE stock is typically a white, fine powder; but its physical morphology/structure becomes the extended chain type by curing it at a temperature above its melting point and also becomes more transparent/translucent. Simultaneously, cure temperature can influence sampler stiffness/rigidity (or conversely flexure) as quantified by flexural modulus determinations, and sampler surface property changes. The proper heat treatment of PTFE applied to glass fiber fabric can significantly contribute to the stability, stiffness, and surface properties of the corresponding sampler with a glass fiber core having PTFE applied thereto.

FIG. 12 indicates a PTFE coating treatment temperature in the range from the PTFE melting point to the PTFE thermal decomposition temperature that can provide desired sampler stability, stiffness, and surface properties. FIG. 12 presents a comparative graph illustrating magnitude versus time response for each of four different samplers to a TNT 10 ng sample when tested with IMS with setup conditions comparable to those for Example One. Each of these different samplers were subjected to a different heat treatment as reflected by the FIG. 12 inset legend. In a top to bottom order of this inset legend: (1) the "hollow triangle" (Δ) data point plot represents the response to approximately a 450° C. heat treatment, which has the second highest peak; (2) the "X" data point plot represents the response to approximately a 400° C. heat treatment, which is the highest peak; (3) the "filled triangle" (▲) data point plot represents the response to approximately a 325° C. heat treatment, which is the third highest peak; and (4) the symbol "*" (an "X" with a vertical line intersecting its cross-point) provides a data point plot representative of the response to approximately a 150° C. heat treatment, which has the lowest peak. Peak timing is comparable for all the plots. Each sampler was comprised of a 10% wt PTFE coating on thin fiber S-glass fabric, and did not have phenyl surface or other functionalization. All samplers were placed in a furnace at the indicated temperature for 30 minutes.

As reflected in FIG. 12, PTFE coatings on thin S-glass fiber fabrics were heat-treated at different temperatures including, below its melting point (150° C. and 325° C.), above its melting point (400° C.), and near its thermal decomposition temperature point (450° C.). Higher stiffness or rigidity was obtained with increased heat treatment temperature, which can be mechanically/quantitatively represented by increasing flexural modulus of the sampler. The PTFE-coated sampler heat-treated at 400° C. demonstrated a higher and sharper peak of TNT thermal desorption release than the other samplers heat-treated at 450° C., 325° C., and 150° C.

Based on Experimental Example Six, the PTFE-coated sampler surface properties and structure seem to change with different heat treatments and correspondingly impact TNT thermal desorption release performance. Scanning Electron Microscope (SEM) and contact angle measurements of PTFE-coated samples were conducted for a better understanding. Contact angles can be used to measure the wettability of surfaces. The measurement indicated the degree of wetting when liquid is deposited on a surface. A low value, <90 degrees, indicates a wettable surface, and is observed when liquid spreads well on the surface. This value range also demonstrates the hydrophilicity of the surface. A contact angle of 0 degree means that complete wetting has occurred. A higher value, >90 degrees, indicates poor wetting, and is observed when liquid beads on the surface. Accordingly, hydrophobic surfaces measure between 90 and 180 degree contact angles. FIGS. 13-20 provide a sequence of computer-generated SEM images of PTFE-coated surfaces on both fabric and a silicon (Si) wafer heated at 150° C., 325° C., 400° C., and 450° C., respectively. The PTFE coating was created by painting a colloidal slurry of suspended PTFE particles on the sampler surface followed by evaporation of the solvent. The slurry was prepared using DUPONT TEFLON PTFE TE-3859 aqueous dispersion. This dispersion contains negatively charged, 0.05 to 0.5 µm PTFE resin particles suspended in water, which also contains approximately 6% (by weight of PTFE) of a nonionic wetting agent and stabilizer.

FIGS. 13 and 14 are computer-generated SEM images of the thin S-glass sampler fabric and Si wafer, respectively, with the coating dried at 150° C. which removes the solvent/water of the applied aqueous dispersion. FIG. 13 corresponds to a contact angle in the range of 0-10 degrees and FIG. 14 corresponds to a contact angle in the range of 50-90 degrees. FIGS. 15 and 16 are computer-generated SEM images of the sampler fabric and Si wafer, respectively, with the coating calcined at 325° C. and baked to remove the nonionic wetting agent (typically at 290° C.). FIG. 15 corresponds to a contact angle in the range of 45-65 degrees and FIG. 16 corresponds to a contact angle in the range of 70-95 degrees. From the SEM images, a granular form of PTFE is observed with sintering and voids in PTFE structure for the 325° C. heat treatment. Based on the contact angle values, samplers prepared at this temperature are in the range indicating hydrophilic surfaces.

FIGS. 17 and 18 are computer-generated SEM images of the sampler fabric and Si wafer, respectively, with the coating calcined at 400° C. which is above the crystalline melting point of the PTFE resin particles (the PTFE melting point is approximately 327° C.). FIG. 17 corresponds to a contact angle in a range of 95-105 degrees and FIG. 18 corresponds to a contact angle in a range of 90-100 degrees. The PTFE particles/granular forms change from white to mostly transparent material with this treatment temperature. The computer-generated SEM images reveal a completely different, transformed morphology, in which the extended chain structure/folded chain structure can be seen. Besides the crystalline morphology change, bridges formed between the fibers of glass can be observed for the 400° C. treated PTFE-coated sampler. Based on empirical data, t is believed that this heat treatment may improve the thermal conductivity of the glass fiber fabric core and PTFE combination due to changes in crystallinity of the PTFE and reduction in voids through better contact of the PTFE with the glass fibers of the sampler fabric. The contact angle demonstrates that the surface of a sampler prepared at this temperature is hydrophobic, which is generally found for detection sampler operation, as previously described.

FIGS. 19 and 20 are computer-generated SEM images of PTFE coating calcined at 450° C., which is approximately the decomposition temperature of PTFE (See Table III). For FIG. 19, a contact angle in a range of 80-95 degrees was determined and for FIG. 20 a contact angle in a range of 90-105 degrees was determined. The material demonstrated a similar morphology and contact angle as the PTFE-coated Si wafer obtained at 400° C., but with longer polymer chains. However, on the PTFE coated fiber S-glass fabric, a poorer coating and lower contact angle is observed, which may be due to the PTFE starting to decompose based on empirical observations. Shrinking of PTFE film can be observed, which results in a greater tendency for direct interaction between the glass fiber surface and analyte(s) as compared to the 400° C. heat treatment.

Accordingly, heat treatment at 150° C. and 325° C., which are both below the PTFE melting point, appear to still allow the spiked TNT analyte to directly contact and interact with the active surface of the glass fiber fabric because the PTFE morphology was relatively unaltered. As a consequence, a lower TNT desorption signal results. A similar outcome is observed for the PTFE-coated sampler subjected to the 450° C. heat treatment. While 450° C. was above the PTFE melting point, it is approximately the same as the empirically-determined PTFE thermal decomposition temperature (448° C. per Table III). The highest signal of TNT thermal desorption is obtained from the PTFE-coated sampler with the 400° C. heat treatment. This heat treatment resulted in a hydrophobic surface with a more uniform coating appearance, which is believed to reduce direct contact/interaction between the TNT analyte and the glass fiber surface.

Example Seven

Applying a thin, incomplete polymer coating with intermittent coverage of the glass fibers enables gas or liquid phase analyte(s) to preferentially bind to the fiber surface regions where the polymer coating is missing or exceedingly thin to a greater degree than where the polymer coating is thicker/more complete. Furthermore, when a thin coating is applied to a glass fabric, the corresponding weave structures reduce the degree of coverage such that the thin coating may be unable to completely cover the active core sites of the fabric, resulting in relatively stronger binding between analyte(s) and the fabric surface. Consequently, less efficient detection of the target analyte(s) result (i.e., no thermal desorption release or decomposition of TNT). Better detection can result if a thicker, more complete polymer coating is applied and/or by silane functionalization of the fabric surface prior to the polymer coating. In contrast, a coating that is too thick undesirably slows analyte release (reduces instrument signal) due to the reduction of thermal conductivity of the sampler. As a result, concentration or thickness of the polymer coating involves trade-offs for each application or detection system type. Moreover, it has been unexpectedly discovered that in certain cases it is more favorable to make multiple thin coatings on the fiber core/substrate for improved uniformity as opposed to a single thick coating deposition (See FIG. 7). In some embodiments, multiple coatings of the same type of polymer are applied to the fiber substrate/core, which may be a fiber fabric or a nonfabric fiber conglomeration; while in other applications, multiple coatings of different compositions/types of polymer are applied to the fiber substrate/core, which also may be a fiber fabric or a nonfabric fiber type.

Experimental Example Seven explored the performance of fiber substrates/cores with different PTFE deposition concentrations for each of three different heat treatment (cure) temperatures. As shown in Table IV below, PTFE in solution concentration by % wt (% wt loadings) were achieved in a couple of different ways: (1) multiple coating layers (dippings) (see second column of Table IV), and (2) use of different solution concentrations (see third column of Table IV):

TABLE IV

| PTFE in solution Concentration (% wt.) | Coating layer | PTFE Concentration in coating (% wt.) | IMS signal of 10 ng TNT | | |
|---|---|---|---|---|---|
| | | | Heat treatment at 325° C. | Heat treatment at 400° C. | Heat treatment at 425° C. |
| 0 | 0 | 0 | 150 | 150 | 120 |
| 7.5 | 1 | 4 | 196 | 198 | 216 |
| 15 | 1 | 12 | 183 | 334 | 372 |
| 22.5 | 1 | 16 | 316 | 439 | 406 |
| 30 | 1 | 20 | 329 | 497 | 534 |
| 22.5 | 2 | 24 | 348 | 580 | 558 |
| 30 | 2 | 30-35 | 436 | 597 | 635 |
| 30 | 3 | 41-45 | 306 | 563 | 546 |

All entries in Table IV employed a thin S-glass fabric core each treated at the indicated temperatures of about 325° C., 400° C., or 425° C. for about 30 minutes. The maximum TNT signal from the sampling material was averaged and reported; using IMS experimental setup/conditions comparable to those for Experimental Example One. It should be appreciated that uncovered core structures can result in irreversible binding of some analytes, as well as the potential for reactive degradation/loss of analytes, which can apply to certain organic species as well as metal species, such as uranyl nitrate and uranyl fluorides.

From Table IV, it was empirically demonstrated that the concentration of polymer coating materials impacted analyte capture and mass transfer in the materials. While thicker coatings typically resulted in better surface passivation, reduced thermal mass flow and reduced thermal conductivity were companion traits. For rapid thermal desorption release, faster thermal mass flow, and to satisfy requirements of trace analyte detection instrumentation; there frequently are trade-offs favoring a somewhat thinner coating to provide better utility for surface sampling applications. In the case of PTFE, the concentration of PTFE not only affects the film thickness, but also tends to impact the physical properties/morphology of the sampler surface.

In Example Seven, as reflected in the Table IV entries, glass fiber samplers were coated with selected coating masses (given as % wt of entire swipe) and then heated to different temperatures of about 325° C., 400° C., and 425° C., respectively, for approximately 30 minutes each. Higher rigidity/stiffness/flexural modulus and hydrophobicity resulted from increased PTFE concentration. The samplers prepared at different temperatures demonstrate a similar response tendency along with increasing PTFE concentration (Table IV). The IMS signals of TNT release were more pronounced with increased concentrations of PTFE up to about 35% wt for the indicated experimental setup. The higher surface hydrophobicity generally resisted polar solvents and analytes entering and diffusing into/through PTFE, which resulted in less chance of TNT contacting undesired active sites on the core surface underneath the PTFE. After solvent evaporation, TNT typically stays on the hydrophobic surface of PTFE, therefore, a higher TNT thermal desorption release signal is obtained.

Samplers prepared at approximately 325° C. demonstrated a lower signal and less rigidity/stiffness—having little or no PTFE melting. On the other hand, higher signals and higher rigidity/stiffness, were obtained from both higher temperature samples at approximately 400° C. and 425° C. These high temperatures exceed the melting temperature of PTFE of about 330° C. but remained below the thermal decomposition temperature of about 448° C., which facilitates transformation of the PTFE particles to extended chain morphology (See also, FIGS. 13-20 and accompanying text). These results tend to indicate that sampler rigidity/stiffness increases with polymer melting—such melting appearing to bind core fabric fibers together. Even with relatively thicker PTFE sampler coatings, a thin S-glass fabric sampler core still provided better TNT release when compared with commercial swipes.

Example Eight

Many core materials with desirable physical/thermal properties have active surfaces which bind analyte(s) without dependable release, reducing the corresponding detection signal. Frequently such materials have polar surfaces, which tend to disrupt uniform polymer coverage. Installation/functionalization of surface chemistries on core materials can act as an interfacial layer that provides better polymer coating and better performance of the samplers. In addition, functionalization of the substrate/core surface promotes uniform spread of the polymer and passivates the fiber surface that may be exposed through imperfect polymer coverage or accidental removal of the polymer layer (i.e. scraped off). High density organo-silane layers can serve as or facilitate formation of a functionalized surface layer as detailed in the '910 patent. An interfacial layer provided by phenyl silanes like depicted in the partial perspective view of FIG. 7, are among those that are thermally stable and compatible with TNT collection/release.

The comparative plots of the graph presented in FIG. 21 illustrate the effect of surface chemistry on thin fiber S-glass for 10 ng TNT detection using IMS with experimental conditions and setup comparable to that for Experiment One. More specifically, the comparative graph of FIG. 21 depicts the 10 ng TNT response of each of three different forms of PTFE-coated samplers with an S-type fiberglass core, two with and one without phenyl surface treatment of the core. The graph presents magnitude versus time of the three sampler responses. Following the top to bottom order of the inset legend: (1) the "X" data point plot represents the response of a phenyl-PTFE sampler configuration heat treated at approximately 150° C.—it has the highest peak, (2) the "hollow triangle" (Δ) data point plot represents the response of a phenyl-PTFE sampler configuration heat treated at approximately 400° C.—it has an intermediate peak, and (3) the "hollow diamond" (◇) data point plot represents the response of a PTFE sampler configuration without functionalization, and heat treatment at approximately 400° C.—it has the lowest peak. All three plots peak at comparable times. For all three samplers, a coating of 10-15% wt PTFE was utilized with heat treatment, each for thirty (30) minutes, at the two temperatures, 150° C. and 400° C.

Example Nine

As per the previous descriptions, surface functionalization applied to the core material of an appropriate type has been surprisingly found to prevent strong binding interactions of the core with the analytes (i.e., TNT) that may potentially interfere desired performance (such as effective thermal desorption). Surface functionalization has been found to impact performance of samplers as demonstrated by prior experimentation (See FIG. 21). A phenyl silane core surface functionalization prior to coating a polymer such as PTFE can demonstrate a significantly higher release signal than an unfunctionalized surfaces to which PTFE is applied. This difference may result because the phenyl groups can prevent the binding of TNT to undesired trapping/active sites of the core. The effect of surface functionalization on a thin fiber S-glass fabric sampler is further demonstrated by Experiment Nine data organized in Table V as follows:

TABLE V

| Surface Functionalization | Curing temperature (° C.) | IMS signal of 10 ng TNT |
|---|---|---|
| None | 325 | 269 |
| None | 400 | 497 |
| Phenyl | 325 | 596 |
| Phenyl | 400 | 598 |

For Table V, the samplers with and without phenyl functionalization were coated with ~30 wt % PTFE solution and then cured at 325° C. or 400° C. to result in ~20 wt % of PTFE after curing. Phenyl installation was achieved by phenyl silane functionalization; refluxing the sampler with 10% by volume phenyl silane in toluene for 18 hours, and preconditioning in a vacuum oven at 180° C. overnight. The maximum TNT signal from sampling material was averaged and reported; using IMS experimental setup/conditions comparable to Example One.

In Table V, both cure temperatures appear to provide high release signals for TNT. Although, for the thin coating of 10-15% wt PTFE reflected in FIG. 21, a slightly slower release can be seen from the more rigid phenyl functionalized sampling material treated at 400° C. The morphology of PTFE changes from granular form to extended chain morphology at this temperature (FIGS. 13-20), which affects the polymer properties, most likely impacts mass transfer and interactions on the surface. For thicker coating (>20% wt PTFE, Table IV), slightly lower release signals for TNT were obtained as compared to the thinner coating. This result is believed to be because of reduced mass transfer and thermal conductivity. FIG. 7 provides a conceptual perspective image of a polymer coated on phenyl functionalized glass core. The phenyl silane (shown as a tethered 6 sided rings P in FIG. 7) provides a surface passivation layer to prevent analyte loss. The interfacial phenyl silane layer provides compatibility with the polymer layer and improves both adhesion and uniform distribution of the polymer coating.

Example Ten

Many polymers are solvent-resistant and thermally stable; however, they often have thermal heat properties (i.e. low thermal conductivity and high specific heat as shown in Table II), which is believed to slow release of analytes from the surface when using thermal desorption techniques common to IMS and other detection instrumentation. It has been surprisingly discovered that for the samplers with PTFE coating, thermal conductivity could be enhanced by adding selected thermally conductive materials, such as $Al_2O_3$ (alumina) nanoparticles into the substrate/core. The $Al_2O_3$ nanoparticle has a thermal conductivity around 30 W/m-K, ~100× better than PTFE and 6× better than fiber S-glass. Other possible micro of nanoparticles to add include metals, other metal oxides, certain carbon allotropes, ceramics, and glass-ceramics. More specifically, Cu, Al, Fe, and Ag are exemplary metals. Other metal oxides include $CeO_2$, and $TiO_2$.

Accordingly, $Al_2O_3$ nanoparticles were added to a thin S-glass fabric core to test whether faster heating and better analyte release were promoted. The results of this experimentation were captured in Table VI as follows:

TABLE VI

| $Al_2O_3$ Addition to core (% wt) | Surface functionalization of $Al_2O_3$ particles | PTFE Concentration (% wt) | Thermal Treatment Conditions (° C.) | IMS signal From 10 ng TNT |
|---|---|---|---|---|
| 0.01 | None | 0 | 360 | 197 |
| 0.05 | None | 0 | 360 | 127 |
| 10.0 | None | 0 | 360 | 0 |
| 0.01 | Phenyl | 0 | 180 | 548 |
| 0.05 | Phenyl | 0 | 180 | 415 |
| 10.0 | None | 20 | 325 | 227 |
| 10.0 | None | 20 | 400 | 576 |
| 10.0 | Phenyl | 20 | 400 | 687 |

$Al_2O_3$ nanoparticles, particle size of about 50 nanometers (nm), were coated on thin S-glass fiber, and then heat treated at 360° C. for 2 hours. Then, the $Al_2O_3$/S-glass core were functionalized with phenyl silane, and/or coated with 20% wt PTFE, and calcined at 325° C. or 400° C., respectively, as reflected in Table VI.

Because the $Al_2O_3$ nanoparticles have a high surface area and chemical activity, strong retention of analytes can occur, reducing the signal from the detection instrumentation. As can be seen in Table VI, the higher the concentration of $Al_2O_3$ used, the lower the release signal of TNT obtained. Therefore, before $Al_2O_3$ nanoparticles are used for their enhanced thermal properties; they should be chemically passivated to avoid analyte binding, which can be accomplished by silanization or thin polymer coating. It is also posited that incorporation of the particles should not block mass transfer and air permeability through the sampler during desorption and detection. Therefore, $Al_2O_3$-thin S-glass was then functionalized with phenyl silane or coated with 20% wt PTFE. As can be seen in Table VI, the post-functionalizations significantly improve the performance of the samplers. It provides a much higher release signal for TNT than those that are not functionalized. The $Al_2O_3$-thin S-glass coating with 20% wt PTFE and treated at 400° C. also show the enhanced desorption of TNT. Accordingly, both post-phenyl functionalization and coating with 20% wt PTFE of $Al_2O_3$-filled thin S-glass provides the highest signal of TNT release. Furthermore, Table VI also shows the consistent effect/improvement with high cure temperature demonstrated in connection with the experimentation of FIG. 21, which is believed to influence the release of TNT from the unfunctionalized $Al_2O_3$-fill samplers. Correspondingly, the curing temperature of 400° C. provides a consistently high release signal for TNT because of the extended chain morphology previously described. As a consequence, one favored embodiment of a sampler material includes a phenyl coated S-glass fiber fabric core with phenyl-coated alumina particles and a thin PTFE coating.

The surface functionalization of the PNNL sampler has chemical selectivity for TNT and other nitroaromatics to provide better chemical uniformity. Selectivity and affinity further improve analytical performance. Thermal conductivity can be further enhanced by adding small amounts of highly thermal conductive materials, such as $Al_2O_3$ nanoparticles, into the core substrate. It has thermal conductivity around 30 W/m-K. Performance of rigid samplers for 10 ng TNT (hand spike) detection using IMS in negative mode. Data was taken in a Barringer IONSCAN 400A ion mobility spectrometer (Smiths Detection). The instrument was operated in negative ion mode at a desorber temperature of 180° C. and a collection time of 10 s. The drift and inlet temperatures for the IMS were set at 114° C. and 240° C., respectively. The sample gas was set at 239 mL/min and the drift gas at 351 mL/min, as per standard IMS instrument settings.

Example Eleven

The verification of compliance with various nuclear material restrictions applicable to certain nation-states and/or monitoring of nuclear processes for safety or other reasons typically involved collection of a substance with a sampler and liquid extraction of the substance from the sampler to provide a substance sample in solution. From this solution, the sample may be further prepared and/or submitted for evaluation by detection instrumentation suitable to identify/quantify uranium content and/or other nuclear material of interest. Such instrumentation includes, but is not limited to Inductively Coupled Plasma Mass Spectroscopy (ICP-MS). As reflected in Table VII, this experimental example tests a PTFE-coated/glass core sampler as applied to nuclear material per operation 718 of FIG. 8 and accompanying text. The relative chemical inertness of PTFE is attractive as a sampler coating because it generally accommodates a wider selection of chemicals and procedures for liquid extraction and analysis of nuclear materials than less chemically inert coatings, and has further advantages as established in Experimental Example Twelve hereafter.

Table VII shows extraction percentage of selected uranium compounds obtained with a PTFE-coated sampler for each of several different extraction agents—most of these agents were applied at two or more different molar (M) concentrations of the same active constituent. Namely, three different nitric acid ($HNO_3$) concentrations were tested (0.0001M, 0.01M, and 6M aqueous solutions), two different sodium carbonate ($Na_2CO_3$) concentrations were tested (0.1M and 1.0M aqueous solutions), and two different concentrations of an equal molar mixture of ammonium carbonate and hydrogen peroxide (($NH_4$)$_2CO_3/H_2O_2$) were tested (1.0M/1.0M and 2.0M/2.0M aqueous solutions). For Experimental Example Eleven, four different chemical forms of uranium were tested to provide a more representative scenario of the different types of samples encountered during field collection. Uranium oxide, $U_3O_8$ or $UO_2$ was tested, which are crystalline compounds with relatively low solubility in water. Uranium Ore Concentrate (UOC) was also tested, which is characteristically a uranium mill product containing a high concentration (at least 90%) of uranium oxide $U_3O_8$. Also tested was Uranyl fluoride ($UO_2F_2$), which is a decomposition product that forms from the reaction of moisture and uranium hexafluoride ($UF_6$). The final compound tested was uranyl nitrate ($UO_2(NO_3)_2$), which is sometimes encountered in the reprocessing of spent fuel.

Different uranium compounds each can have a different solubility with respect to the same solution. A relatively weak acid solution (0.01 M $HNO_3$) provided suitable extraction and solubility of $UO_2F_2$ and $UO_2(NO_3)_2$, while a stronger solution (i.e. ($NH_4$)$_2CO_3/H_2O_2$ (2 M)) more suitably provided for complete extraction of $U_3O_8$ and UOC. The $U_3O_8$ form of uranium (including typical yellow cake) exhibited the greatest chemical stability (and associated resistance to extraction) even with a 6M nitric acid concentration. Based on these empirical observations, it is fair to surmise that with extended extraction times, a higher acid concentration, and/or a different agent that 100% extraction of $U_3O_8$/yellow cake could be approached, as exemplified by the test results for the $U_3O_8$/yellow cake extracts provided with the ($NH_4$)$_2CO_3/H_2O_2$ (2 M) mixture. Average extraction percentage was calculated from triplicate samples. The PTFE-coated samplers were in contact with extraction solutions for approximately 18 hours. Relatively fast kinetics were observed for anthropogenic compounds (i.e., $UO_2F_2$, $UO_2(NO_3)_2$). In fact, rapid kinetic dissolution rates of uranyl nitrate and uranyl fluoride from PTFE-coated glass core removed about 80-100% within 60 minutes under certain conditions. PTFE-coated sampler testing was performed with a DSA brand, commercially available swipe—the test results were captured in Table VII as follows:

TABLE VII

| Extraction Solution | % Average Extraction Efficiency | | | |
|---|---|---|---|---|
| | $U_3O_8$ | UOC | $UO_2F_2$ | $UO_2(NO_3)_2$ |
| Deionized Water | 3 | 38 | 24 | 49 |
| $HNO_3$ (0.0001M) | 3 | 17 | 38 | 44 |
| $HNO_3$ (0.01M) | 49 | 65 | 97 | 100 |
| $HNO_3$ (6.0M) | 70 | 73 | 100 | 100 |
| $Na_2CO_3$ (0.1M) | 49 | 18 | 95 | 90 |
| $Na_2CO_3$ (1.0M) | 58 | 79 | 100 | 100 |
| ($NH_4$)$_2CO_3/H_2O_2$ (1M) | 100 | 72 | 94 | 100 |
| ($NH_4$)$_2CO_3/H_2O_2$ (2M) | 98 | 100 | 100 | 96 |

Example Twelve

Uranium/uranium compound sample preparation traditionally has involved acquisition with a cotton fabric swipe. Sample extraction from a cotton swipe has proven rather labor-intensive, extending a day or more in some cases. In this experimental example, a range of different uranium extraction agents were tested comparatively with both a TEXWIPE 304 cotton swipe and a PTFE-coated glass core sampler of the type used in Experimental Example Eleven, which demonstrated various differences leading to the unexpected, surprise discovery of several advantages of the PTFE-coated sampler. The TEXWIPE 304 swipe is a double-sided twill-pattern cotton wiper purportedly woven in a cross section of 118×60 threads per square inch with long staple cotton yarn under clean room conditions, and reportedly has cellulose fibers with a relatively low level of naturally occurring uranium. Extraction and analysis of deposited uranium compound particles on PTFE samplers were achieved in hours, or up to a day for hard mineral compounds. In contrast, pre-existing cotton swipe schemes take many more chemical steps and more time (with corresponding labor cost increases) to analyze uranium particles with standard protocols.

Table VIII presents basic extraction efficiency results that shows better recovery of analyte from the PTFE-coated sampler than the TEXWIPE 304 cotton swipe for most tested conditions. These test results confirmed prior understanding that the TEXWIPE 304 composition has poor efficiency with respect to some of the listed extraction solutions, but the performance of a PTFE-coated sampler was largely unknown before this experimentation. In addition to the four different chemical forms of uranium submitted to extraction in Experimental Example Eleven, Experimental Example Twelve also tested extraction efficiency for uranyl orthophosphate, $(UO_2(HPO_4)*4H_2O)$, which is also known by the abbreviation "HUP."

Per Table VIII, the applied extraction agents were weak and strong nitric acid (0.01 and 6 M aqueous solutions), sodium carbonate (1 M aqueous solution), and acetone (laboratory grade purity). The highest concentration of $HNO_3$ acid used (6.0 M) displayed the greatest extraction percentage; however, the increased performance of 6.0 M nitric acid relative to 0.01 M $HNO_3$ for the extraction of different chemical forms of uranium from the TEXWIPE 304 was generally marginal for all but $U_3O_8$. $U_3O_8$ extraction removal from both swipe materials exhibited the lowest efficiency, which corresponds to the relatively strong kinetic and thermodynamic stability and slower dissolution kinetics of this compound—resulting in a relatively high extraction resistance—even when subjected to 6.0 M nitric acid. Like Experimental Example Eleven, it is reasonable to conclude that with extended extraction times and stronger acid(s), 100% extraction could be obtained. Correspondingly, a PTFE-coated sampler may enable recovery of uranium analytes of interest (e.g., by acidic leaching) without requiring total digestion of the sampler material under certain circumstances.

Acetone is a polar high-volatility organic solvent. In part, the selection of acetone as an extraction agent was because of its relatively high volatility under standard temperature and pressure conditions, so that it provided concentrated uranium-bearing solids after its quick and relatively easy evaporation. The resulting solid uranium extract was a form more suitable for certain subsequent analytical techniques; however, it should be appreciated dissolution is still required typically to perform ICP-MS. While the data in Table VIII indicates that uranium extraction with acetone from the PTFE-coated sampler is slightly more effective than the cotton TEXWIPE 304 swipe, the extraction efficiency for acetone relative to the other extraction agents was consistently less:

TABLE VIII

| | | % Extraction[c, d] | | | |
|---|---|---|---|---|---|
| Swipe Material | U Compound[a, e] | 0.01M $HNO_3$ | 6.0M $HNO_3$ | 1.0M $Na_2CO_3$ | Acetone |
| TEXWIPE 304 | $U_3O_8$ | 47 | 58 | 58 | 44 |
| | UOC | 64 | 70 | 70 | 43 |
| | $UO_2F_2$ | 86 | 100 | 100 | 50 |
| | $UO_2(HPO_4)*4H_2O$ | 100 | 100 | 100 | 57 |
| | $UO_2(NO_3)_2$[b] | 84 | 100 | 100 | 37 |
| PTFE-Coated Fiberglass | $U_3O_8$ | 49 | 70 | 58 | 43 |
| | UOC | 65 | 73 | 100 | 48 |
| | $UO_2F_2$ | 97 | 100 | 100 | 48 |
| | $UO_2(HPO_4)*4H_2O$ | 100 | 100 | 100 | 63 |
| | $UO_2(NO_3)_2$[b] | 100 | 100 | 100 | 64 |

[a]The uranium was spiked onto the swipe materials from a Dimethyl Sulfoxide (DMSO) suspension and allowed to air dry.
[b]Uranium in 2% $HNO_3$ instead of DMSO.
[c]The concentrations and extraction of uranium were determined via ICP-MS detection of $^{238}U$.
[d]The extraction was performed by placing the spiked swipes in 5 mL of extractant and continually shaken for approximately 18 hours at room temperature.
[e]$U_3O_8$ is a stable, common form of uranium oxide commonly found in nature; UOC is a commercial, uranium mill product high in $U_3O_8$; $UO_2F_2$ is a hydrolysis product of $UF_6$ that is water soluble and decomposes to $U_3O_8$ at 300° C.; $UO_2(HPO_4)*4H_2O$ is a naturally occurring uranium complex corresponding to strong uranium immobilization properties of different phosphate minerals; and $UO_2(NO_3)_2$ is prepared from uranium salts treated with nitric acid.

The progressive dissolution of $UO_2NO_3$, $UO_2F_2$ and $U_3O_8$ into nitric, sodium carbonate, and ammonium carbonate/peroxide solutions over time is graphically shown in FIGS. 26-28, respectively. Aliquots were taken periodically from each sample vial, which contained spiked swatches of swipe material submerged in extraction solution. Growth functions were applied to each data set to generate non-linear curve fits that depict the trend of uranyl release in each extraction solution. It should be appreciated that uranyl fluoride and uranyl nitrate are rapidly removed from PTFE-coated samplers. Between 80 and 100% extraction of uranyl fluoride and uranyl nitrate was achievable in less than 10 minutes using an aqueous solution including a mixture of $(NH_4)_2CO_3$ and $H_2O_2$ in equal molar amounts to provide a rinsing agent. This result correlates to the data collected for the same dissolution study done with TEXWIPE 304 sampling material.

Example Thirteen

A gas-phase chemical reaction synthesized PTFE for submission to uranium background content testing. From such a source, it has been discovered that PTFE can have some of the lowest metal (e.g., uranium) backgrounds relative to commercial sampling materials. Experimentally, background levels of uranium for different PTFE-coated samplers was found highly dependent on the sampler source. A pretreatment acid wash of the PTFE-sampler materials was found to reduce background levels substantially, with some as low as 0.05 nanogram (ng) of uranium per sampler. Preparation of PTFE-coated glass fabric samplers for this experimentation proceeded under clean laboratory conditions with assiduous contamination control—and included deposition of highly pure PTFE nanoparticles from colloidal suspension on the glass fabric followed by calcination to form a hydrophobic microcrystalline surface layer. These samplers were found to have the lowest uranium background of any PTFE-coated sampler material tested.

Empirical investigation further included rinsing a batch of TEXWIPE 304 swipes five (5) successive time with ultrapure nitric acid (6.0 M) to leach uranium therefrom. After each rinse, ICP-MS instrumentation provided measurements of the remaining background uranium. These measurements of the TEXWIPE 304 swipe material with each successive acid rinse were: 0.55, 0.036, 0.028, <0.010, <0.010 nanogram per gram (ng/g) of sampler material, respectively. Table IX summarizes these test results, comparing them to two different PTFE-coated sampling materials also submitted to successive rinsing with concentrated nitric acid (6.0 M) five (5) times and corresponding background uranium measurement. Background uranium of TEXWIPE 304 swipes was found to be marginal after just a few acid treatments, and was found negligible in samples of pure PTFE even after just one rinse. By contrast, commercially-sourced PTFE-coated fiberglass fabric sampler materials displayed much higher uranium background levels, which, at least in part, is theorized to result from formation by sintering PTFE powder to the fabric. In contrast, the laboratory preparation of in-house PTFE-coated fiberglass fabric samplers (parenthetically designated by "PNNL" in the Table IX study results) included dip-coating lower-mass fiberglass in a colloidal suspension of PTFE micro/nanoparticles and then thermally curing in a furnace. Per Table IX, contamination-controlled PTFE preparation and handling conditions achieved a lower uranium background, as follows:

TABLE IX

| Swipe Materials | Acid Leached Uranium* (ng/g material) | |
| --- | --- | --- |
| | $1^{st}$ rinse | $5^{th}$ rinse |
| TEXWIPE 304 | 0.55 (+/−0.3) | <0.010 |
| Pure PTFE | <0.010 | <0.010 |
| PTFE-coated Fiberglass (PNNL) | 1.8 (+/−0.2) | <0.010 |
| Commercial PTFE-coated Fiberglass | 271-405 | 140-150 |

*During cleaning process, all measurements in triplicate

In a further aspect of the Experimental Example Thirteen investigation, it also was discovered that solutions of ammonium carbonate/hydrogen peroxide, explored for sampler extraction and rinsing, removed impurities from PTFE-coated sampler material. The combination of ammonium carbonate and a strong oxidizing agent (such as hydrogen peroxide) in solution, removed surface impurities that tend to cause sampler discoloration. For instance, commercially-sourced PTFE-coated fiberglass fabric samplers were submerged in such a solution for about twelve (12) hours, turning the surface color from a beige/tan to white.

Any experiment, theory, thesis, hypothesis, mechanism, proof, example, belief, speculation, conjecture, guesswork, or finding stated herein is meant to further enhance understanding of the present application without limiting the construction or scope of any claim that follows or invention otherwise described herein—except to the extent expressly recited in such claim or invention. For any particular reference to "embodiment" or the like, any aspect(s) described in connection with such reference are included therein, but are not included in nor excluded from any other embodiment absent reasonable description to the contrary. For multiple references to "embodiment" or the like, some or all of such references refer to the same embodiment or to two or more different embodiments depending on corresponding modifier(s) or qualifier(s), surrounding context, and/or related description of any aspect(s) thereof—understanding two embodiments differ only if there is some substantive distinction, including but not limited to any substantive aspect described for one but not included in the other. Any use of the words: important, critical, crucial, significant, essential, salient, specific, specifically, imperative, substantial, extraordinary, especially, favor, favored, favorably, favorable, desire, desired, desirable, desirably, particular, particularly, prefer, preferable, preferably, preference, and preferred indicates that the described aspects being modified thereby may be desirable (but not necessarily the only or most desirable), and further may indicate different degrees of desirability among different described aspects; however, the claims that follow are not intended to require such aspects or different degrees associated therewith except to the extent expressly recited, but the absence of such recitation does not imply or suggest that such aspects are required to be absent from the claim either. For any method or process claim that recites multiple acts, conditionals, elements, gerunds, stages, steps, operations, phases, procedures, or other claimed features; no particular order or sequence of performance of such features is thereby intended unless expressly indicated to the contrary as further explained hereinafter. There is no intention that method claim scope (including order/sequence) be qualified, restricted, confined, limited, or otherwise influenced because: (a) the method/process claim as written merely recites one feature before or after another; (b) an indefinite article accompanies a method claim feature when first introduced and a definite article thereafter (or equivalent for method claim gerunds) absent compelling claim construction reasons in addition; or (c) the claim includes alphabetical, cardinal number, or roman numeral labeling to improve readability, organization, or other purposes without any express indication such labeling intends to impose a particular order. In contrast, to the extent there is an intention to limit a method/process claim to a particular order or sequence of performance: (a) ordinal numbers (1st, 2nd, 3rd, and so on) or corresponding words (first, second, third, and so on) shall be expressly used to specify the intended order/sequence; and/or (b) when an earlier listed feature is referenced by a later listed feature and a relationship between them is of such a type that imposes a relative order because construing otherwise would be irrational and/or any compelling applicable claim construction principle(s) support an order of the earlier feature before the later feature. However, to the extent claim construction imposes that one feature be performed before another, the mere ordering of those two features is not intended to serve as a rationale or otherwise impose an order on any other features listed before, after, or between them. Moreover, no claim is intended to be construed as including a means or step for performing a specified function unless expressly introduced in the claim by the language "means for" or "step for," respectively. As used herein, "portion" means a part of the whole, broadly including both the state of being separate from the whole and the state of being integrated/integral/contiguous with the whole, unless expressly stated to the contrary. Representative embodiments in the foregoing description and other information in the present application possibly may appear under one or more different headings/subheadings. Such headings/subheadings go to the form of the application only, which while perhaps aiding the reader, are not intended to limit scope or meaning of any embodiments, inventions, or description set forth herein, including any claims that follow. Only representative embodiments have been described, such that: acts, additions, advantages, alterations, apparatus, aspects, benefits, changes, components, compositions, constituents, deletions, devices, embodiments, equivalents, features, forms, implementations, materials, methods, modifications, objects, operations, options, phases, processes, refinements, steps, stages, structures, substitutions, systems, techniques, and variations that come within the spirit, scope, and/or meaning of any inventions defined herein, including any of the following claims, are desired to be protected.

What is claimed is:

1. An instrumental analysis sampling method, the method comprising:
   collecting a substance within external openings of a three-dimensional collection framework above a support structure comprising at least partially polymer coated glass, wherein the framework corresponds to a number of interconnected coincident polyhedra to form a three-dimensional tessellation; and
   transferring the substance from the external openings to an analytical instrument.

2. The method of claim 1, in which length, width, and height of the framework differ from each other by a factor of no more than about 1.25.

3. The method of claim 1, wherein a height of the framework is greater than or equal to about ¾ of the width of the framework.

4. The method of claim 1, in which the collection framework includes links joined at nodes corresponding, respectively, to edges and vertices of the polyhedra with at least six external faces, each of the faces defining an external aperture intersecting a passage through the collection framework.

5. The method of claim 1, in which the collection framework is shaped to correspond to a bitruncated cubic honeycomb form of the polyhedra, the collection framework defining a number of coincidentally interconnected, adjacent truncated octahedral shapes of the honeycomb.

6. The method of claim 1, in which the collecting of the substance includes swiping the sampler along a surface of interest to accumulate the substance in the form of a contraband or undesired substance in the passages through the external openings, and the transferring of the substance includes performing liquid extraction.

7. The method of claim 6, wherein:
   the polymer comprises one or more of: PTFE, FEP, ETFE, and/or PFA;
   the framework length, width, and height are no more than 1.5 greater than another; and
   the framework defines a lattice.

8. The method of claim 6, wherein the polymer comprises PTFE; and the contraband or undesired substance includes at least one of: uranium, plutonium, and a heavy metal.

9. The method of claim 1, wherein the framework defines a cage having a network of intersecting passages therethrough.

10. The method of claim 1 wherein the three-dimensional collection framework is defined by a swab configured to swipe a surface to be sampled.

* * * * *

UNITED STATES PATENT AND TRADEMARK OFFICE
CERTIFICATE OF CORRECTION

PATENT NO. : 10,254,248 B2
APPLICATION NO. : 14/692460
DATED : April 9, 2019
INVENTOR(S) : Raymond S. Addleman et al.

Page 1 of 1

It is certified that error appears in the above-identified patent and that said Letters Patent is hereby corrected as shown below:

On the Title Page

Item [56], Replace "4,003,257 A 1/1977 Flecther et al." with --4,003,257 A 1/1977 Fletcher et al.--

In the Specification

Column 53, Line 61 - Replace "t is believed" with --it is believed--

Signed and Sealed this
Tenth Day of December, 2019

Andrei Iancu
*Director of the United States Patent and Trademark Office*